(12) United States Patent
Mukherjea et al.

(10) Patent No.: US 12,162,935 B2
(45) Date of Patent: Dec. 10, 2024

(54) REGIMENS, COMPOSITIONS AND METHODS WITH CAPSAICIN AND TNF-ALPHA INHIBITOR

(71) Applicant: Board of Trustees of Southern Illinois University, Carbondale, IL (US)

(72) Inventors: Debashree Mukherjea, Springfield, IL (US); Vickram Ramkumar, Springfield, IL (US); Leonard Rybak, St. Louis, MO (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 975 days.

(21) Appl. No.: 17/169,950

(22) Filed: Feb. 8, 2021

(65) Prior Publication Data

US 2021/0253689 A1 Aug. 19, 2021

Related U.S. Application Data

(63) Continuation-in-part of application No. PCT/US2019/045751, filed on Aug. 8, 2019.

(60) Provisional application No. 62/715,878, filed on Aug. 8, 2018.

(51) Int. Cl.
*C07K 16/24* (2006.01)
*A61K 31/165* (2006.01)
*A61K 39/00* (2006.01)
*A61P 27/16* (2006.01)

(52) U.S. Cl.
CPC .......... *C07K 16/241* (2013.01); *A61K 31/165* (2013.01); *A61P 27/16* (2018.01); *A61K 2039/505* (2013.01)

(58) Field of Classification Search
CPC .............. C07K 16/241; C07K 2319/30; C07K 2319/32; A61K 31/165; A61K 2039/505; A61K 45/06; A61K 38/00; A61P 27/16; A61P 35/00
See application file for complete search history.

(56) References Cited

U.S. PATENT DOCUMENTS

2001/0004456 A1* 6/2001 Tobinick ................ A61K 38/20
424/85.1

OTHER PUBLICATIONS

Breglio AM et al. Cisplatin is retained in the cochlea indefinitely following chemotherapy. Nature Communications 2017, 8, 1654 1-9 (Year: 2017).*
Liberman MC et al. Cochlear synaptopathy in acquired sensorineural hearing loss: Manifestations and mechanisms. Hear Res 2017, 349, 138-147 (Year: 2017).*
Bhatta P. Protective effect of capsaicin against cisplatin ototoxicity (ProQuest LLC 2015) (Year: 2015).*
Kaur T Targeting cochlear inflammation for the treatment of cisplatin ototoxicity. (ProQuest LLC 2012) (Year: 2012).*
Sandstrom S et al. Auditory Rangers (https://www.siumed.edu/mc/auditory-rangers, Summer 2016). (Year: 2016).*

* cited by examiner

*Primary Examiner* — Karen A. Canella
*Assistant Examiner* — John J Skoko, III
(74) *Attorney, Agent, or Firm* — Husch Blackwell LLP

(57) ABSTRACT

Compositions and treatment regimen that includes the compositions, suitable for preventing, treating and restoring hearing acuity in a subject are provided. The treatment regimen includes an amount of capsaicin and an amount of a TNF-α inhibitor (such as etanercept) that are delivered relatively simultaneously to a subject. Methods of providing a pretreatment to a subject suitable for preventing hearing loss are also provided. The capsaicin and TNFα inhibitor may be provided in different delivery forms to the subject. Methods of providing a treatment for hearing loss with a TNFα inhibitor alone, such as entanercept, or with capsaicin alone, are also provided.

20 Claims, 33 Drawing Sheets

Specification includes a Sequence Listing.

| TRPV1 | OHC | SG | SVA |
|---|---|---|---|
| Cisplatin | 223±10%* | 162±7%* | 251±12%* |
| TT-Capsaicin + Cisplatin | 110±7%** | 130±9%** | 80±5%** |
| Capsaicin | 112±8% | 100±5% | 108±7% |
| NOX3 | OHC | SG | SVA |
| Cisplatin | 185±10%* | 320±10%* | 260±12%* |
| TT-Capsaicin + Cisplatin | 110±4%** | 112±10%** | 120±7%** |
| Capsaicin | 97±5% | 100±7% | 100±6% |
| INOS | OHC | SG | SVA |
| Cisplatin | 248±15%* | 240±12%* | 220±10%* |
| TT-Capsaicin + Cisplatin | 127±10%** | 125±10%** | 118±8%** |
| Capsaicin | 95±3% | 100±2% | 105±5% |

| p-STAT3/p-STAT1 ratio | OHC | SG | SVA |
|---|---|---|---|
| Oral PBS | 130±12% | 117.15±10% | 81.63±5% |
| Cisplatin | 64.1±4%* | 72.9±5%* | 62.91±5% |
| Oral-Capsaicin + Cisplatin | 189.4±12%** | 114.5±8%** | 115.62±8%** |
| Oral Capsaicin | 297.4±15%*ƒ** | 168.8±11%*ƒ** | 130.4±9%*ƒ** |

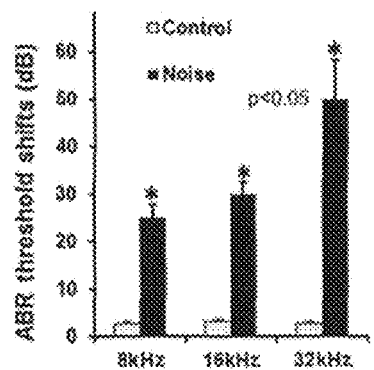
FIG. 14A
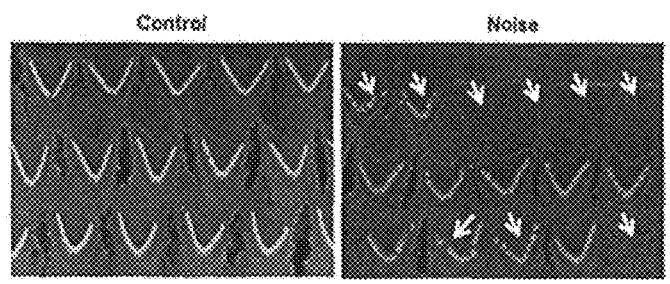
FIG. 14B
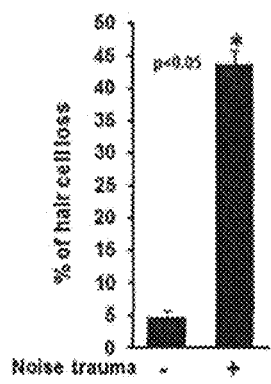 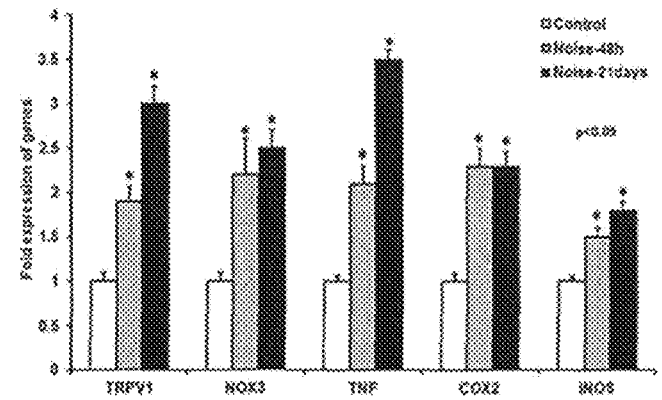
FIG. 14C　　　　FIG. 14D FIG. 23A
FIG. 23B
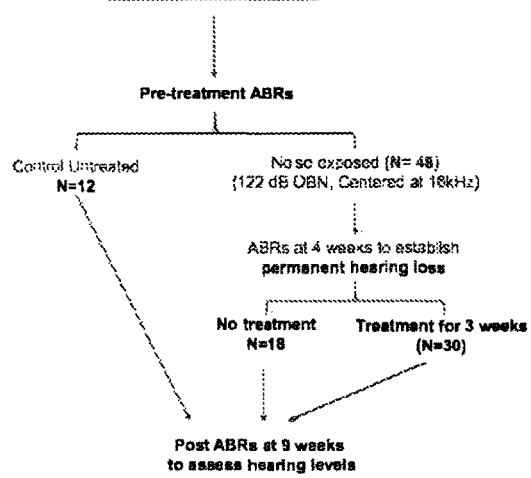
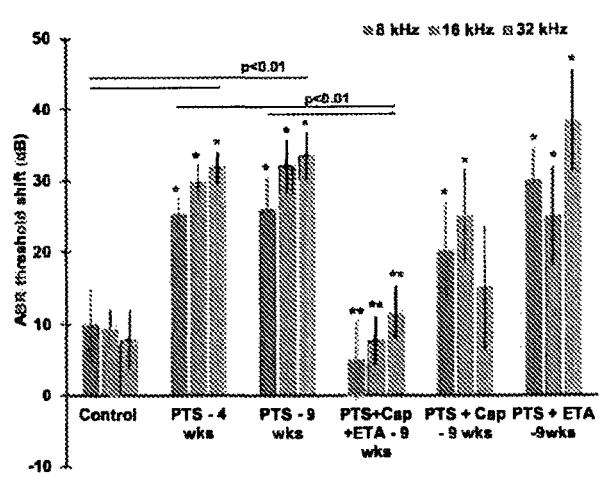
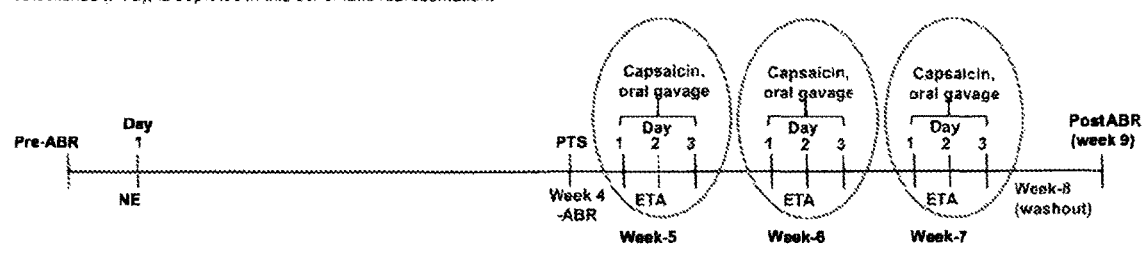
FIG. 23C

REGIMENS, COMPOSITIONS AND METHODS WITH CAPSAICIN AND TNF-ALPHA INHIBITOR

RELATED APPLICATIONS

The present application is a continuation-in-part of International Application No. PCT/US2019/045751. International Application No. PCT/US2019/045751 claims priority to U.S. provisional patent application 62/715,878, filed Aug. 8, 2018, the contents of which are specifically incorporated herein by reference.

SUBMISSION OF SEQUENCE LISTING

The contents of the electronic submission of the text file Sequence Listing, which is named 500977_169_Sequence_Listing.txt, which was created May 3, 2021, and is 8 KB in size, is incorporated herein by reference in its entirety.

BACKGROUND OF THE INVENTION

Cisplatin is a chemotherapeutic agent and widely used for treating solid tumors. However, cisplatin therapy produces serious side effects such as nephrotoxicity, neurotoxicity, and severe ototoxicity. Cisplatin-induced ototoxicity is bilateral and irreversible, and thus particularly serious in the pediatric population, especially during early development to about three years of age. Cisplatin is frequently used to treat cancers like neuroblastoma and CNS neuroblastoma tumors, but the resulting ototoxicity hampers speech, cognition and social development. Thus, a great need exists for treatments that will ameliorate cisplatin-induced ototoxicity and other side effects.

Hearing loss also results from ageing and exposure to noise, Exposure to high levels of noise is the most common cause. Hearing is a critical sense in many occupations, and especially for those in the military. Hearing injuries can threaten safety and fitness for duty, impeding communication, reducing situational awareness, hindering threat detection, and ultimately degrading mission effectiveness, as well as permanently reducing quality of life.

Hearing loss remains the second most prevalent disability among veterans with the number of veterans receiving compensation for hearing steadily increasing (24.9% (1.1 million) in 2016). An urgent unmet need for viable treatment options and preventative measures to reduce noise-induced hearing loss (NIHL) continues to exist. No known FDA approved drugs for prevention or rescue of hearing loss, such as NIHL, have been reported.

A critical medical continues to exist for preventing hearing loss, as well as techniques for restoring hearing loss.

SUMMARY OF THE INVENTION

The above and other unmet needs in the art are provided according to the present invention.

In one aspect, compositions and regimens comprising the compositions are provided. In some embodiments, the compositions include a TRPV1 agonist, such as capsaicinoid, for example, capsaicin. The capsaicin containing composition is further described as including relatively low amounts and/or concentrations of capsaicin. The low concentrations of capsaicin may be further described a sub-optimal concentration of capsaicin. In another embodiment, a composition comprising a TNFα-inhibitor, for example, etanercept, is provided. The TNFα inhibitor containing composition is further described as including a relatively low amount and/or concentration of the TNFα-inhibitor, for example, etanercept. The low concentration of the TNFα-inhibitor may be further described as a dosage concentration of the TNFα-inhibitor.

In another aspect, physiologically protective compositions and methods of using the physiologically protective compositions are provided. Embodiments of the physiologically protective compositions, and the treatment regimens that use them, comprise a pharmacologically active ingredient or combination of such active ingredients, these active ingredients comprising a TNFα-inhibitor (for example, etanercept), a TRPV1 agonist (for example, a capsaicinoid such as capsaicin), or a combination thereof. These pharmacologically active ingredients may be administered to a subject individually or together.

The active ingredients of the compositions may be formulated so as to be suitable for administration to a subject via any variety of different administration routes (intravenous (i.v.), oral. subcutaneously, oral, aerosol, trans tympanic, etc.

The treatment regimens described herein provide for an improvement in decibel hearing sensitivity level in a subject having a reduced hearing capacity associated with ageing, toxic chemical agent exposure (such as a chemotherapeutic agent), damaging noise level, or any combination of these.

As part of the treatment regimens described herein, a dosage amount of an active ingredient may be further described as a relatively low dose of the active ingredient. In the above described embodiments, for example, a dosage amount of a TNF-α inhibitor and/or TRPV1-agonist (such as capsaicin) may be described as an amount of the active ingredient that alone does not result in a measurable change in one or more physiological parameters associated with hearing in a subject. For example, a physiological parameter associated with hearing sensitivity in a subject is a change in the decibel (dB) level at which a subject is able to hear a sound.

As described in the present regimens and methods, an improvement in hearing sensitivity, described herein as an improved ability to hear a sound at a lower decibel (dB) level, is provided to a treated subject. Upon administration of a composition comprising a suboptimal amount of a TNFα inhibitor (such as etanercept) and a composition comprising a suboptimal amount of a TRPV1-agonist (such as capsaicin), an improvement in hearing sensitivity is evidenced in the treated subject by a decrease in the decibel level at which the treated subject is able to hear, compared to the subject's decibel hearing level before treatment, or compared to a decibel level at which a subject or group of subjects (on average) having a similar pre-treatment hearing sensitivity level not having received the regimen and/or combination of compositions. An improvement in hearing sensitivity is defined as a decrease in decibel (dB) level hearing sensitivity in a subject of about 10%, about 15%, about 20% or greater, compared to a decibel hearing sensitivity level of the subject prior to treatment, or compared to a subject or group of subjects having a similarly impaired hearing sensitivity level that did not receive the regimen and/or compositions.

In some embodiments, the treatment regimen and/or methods comprise a series of steps. These steps may comprise: providing a subject with a dosage amount of a TRPV agonist (for example, a CB2 agonist, capsaicin), providing the subject with a sub-optimal amount of a TNF-α inhibitor, and decreasing the decibel (dB) sensitivity level of hearing in the treated subject. The treatment steps may be provided in any order or may be provided simultaneously to a subject.

Other embodiments of the invention are directed to physiologically restorative and/or oto-regenerative compositions and therapeutic regimens. In some embodiments, these restorative and/or regenerative compositions comprise a pharmacologically active agent or combination of such agents, that include a TNFα-inhibitor, capsaicin, or a combination thereof. These pharmacologically active agents may be administered individually via different administration routes (intravenously (i.v.) subcutaneously (subq,), orally, retro-auricular (behind the ear), trans tympanic, etc.), depending on the particular modality desired and best suited for a subject. As part of the treatment regimens described herein, for example, a subject having a reduced and/or impaired physiological condition (immunological, inflammatory disease related, hearing, etc.), especially a condition, illness or accident, that results in an impairment in the subject's hearing sensitivity level, may be administered a relatively low dose of a TNF-α inhibitor, and a relatively low dose of a TRPV1 agonist (for example, capsaicin). In this manner, and in some aspects of the treatment regimen, the administration of capsaicin and a TNF-α inhibitor (e.g., etanercept, an anti-TNF-α monoclonal antibody such as adalimubab, golimubab, infixamab, or combinations thereof) may be provided simultaneously or at approximately the same time to the subject. The physiologically restorative and/or regenerative composition and treatment regimens may be used to enhance or improve the hearing ability and/or hearing level in a hearing compromised subject. Preferably, the restorative and/or regenerative regimens, and the compositions and treatment methods associated therewith, will be provided to a hearing compromised or impaired subject shortly after a hearing compromising event has occurred to the subject. By way of example, such a hearing compromising event may include noise or exposure to an ototoxic agent.

Specific methods for preventing hearing loss are also disclosed. In this manner, hearing damage may be presented in a subject by treating the subject according to the methods disclosed herein. In some embodiments, the method comprises treating a subject with a TNF-α inhibitor (for example, etanercept, an anti-TNF-α monoclonal antibody such as adalimubab, golimubab, infixamab, or combinations thereof) and a TRPV1 agonist (for example, capsaicin) before a subject is anticipated to be exposed to a hearing compromising event. For example, such may be provided to a subject prior to being deployed into a situation where loud noise is likely to occur. Such situations may include a military or war-time situation.

Methods are also provided for restoring hearing loss through repairing damage to cochlear hair structures, auditory nerve, spiral ganglion neuron and/or synapses. The methods comprise administering an oto-restorative composition comprising a dosage amount of a TNF-α inhibitor (for example, etanercept, an anti-TNF-α monoclonal antibody such as adalimubab, golimubab, infixamab, or combinations thereof), administering a dosage amount of a TRPV1 agonist (for example capsaicin), simultaneously or sequentially, and restoring hearing in the treated subject. According to some embodiments, hearing sensitivity levels are restored to a hearing sensitivity decibel level that is at least 10%, 15%, 20% or even more, less than a decibel hearing sensitivity level in the subject prior to treatment, or compared to a hearing sensitivity level of a group of subjects having experienced a similar auditory compromising event or condition, such as noise level, pathology associated with a loss in hearing acuity, disease treatment regimen (for example, chemotherapy (e.g., cisplatin treatment) or toxic agent exposure (environmental, occupational (e.g., factory worker, military personnel, chemical factory, etc.), high ambient noise environment).

Additional aspects and embodiments of the present invention are described in more detail below.

BRIEF DESCRIPTION OF THE SEQUENCE LISTING

SEQ ID NOs 1 and 2 show the Rodent-Bax primer set used in Example 1.
SEQ ID NOs 3 and 4 show the Rodent-Bc12 primer set used in Example 1.
SEQ ID NOs 5 and 6 show the Rodent-iNOS primer set used in Example 1.
SEQ ID NOs 7 and 8 show the Rodent-GAPDH primer set used in Example 1.
SEQ ID NOs 9 and 10 show the Rodent NOX3 primer set used in Example 1.
SEQ ID NOs 11 and 12 show the Rodent-CB2 primer set used in Example 1.
SEQ ID NOs 13 and 14 show the Rodent TRPV1 primer set used in Example 1.
SEQ ID NOs 15 and 16 show the Rodent-GAPDH primer set used in Example 8.
SEQ ID NOs 17 and 18 show the Rodent TRPV1 primer set used in Example 8.
SEQ ID NOs 19 and 20 show the Rodent NOX3 primer set used in Example 8.
SEQ ID NOs 21 and 22 show the Rodent-TNF-α primer set used in Example 8.
SEQ ID NOs 23 and 24 show the Rodent-COX2 primer set used in Example 8.
SEQ ID NOs 25 and 26 show the Rodent iNOS primer set used in Example 8.

BRIEF DESCRIPTION OF THE DRAWINGS

-FIG. 1.E. FIG. 1.B. SEM studies performed on rat *cochleae* show disruption of the stereociliary bundles indicating damage to the OHCs by cisplatin which was significantly ameliorated by pre-treatment with capsaicin. FIG. 1.C. Quantitative analysis of outer hair cell damage in the basal turn in the SEM images. (*indicates significant difference from control; **indicates significant difference from cisplatin treatment, $p<0.05$, n=4). FIG. 1.D. Cochlear whole mount preparations from animals stained with myosin VIIA and imaged by confocal microscopy indicate that cisplatin caused hair cell loss in the basal turn (indicated by red arrows), while capsaicin pre-treatment was protective. Scale bar is 25 μm. FIG. 1.E. Quantitative analysis of presence or absence of outer hair cells from the basal turn of the whole mount. (*indicates significant difference from control; **indicates significant difference from cisplatin treatment, $p<0.05$, n=4).

-FIG. 2.C. FIG. 2.A. Capsaicin inhibits cisplatin-induced stress and inflammation in the cochlea. Male Wistar rats were pretreated with trans-tympanic capsaicin (0.1 µM, 50 µl) 24 h prior to cisplatin (11 mg/kg). The cochleae was collected 72 h post cisplatin, and these specimens were saved either in RNA later or fixed with freshly prepared 4% paraformaldehyde, decalcified and processed mid-modiolar sections. Quantitative q-PCR analyses from total cochlear RNA indicate that cisplatin treatment increased the relative mRNA expression of TRPV1, NOX3 and iNOS that was inhibited by trans-tympanic pre-treatment with capsaicin. FIG. 2.B. and FIG. 2.C. Mid-modiolar sections were used for immunofluorescent staining of TRPV1 (FIG. 2.B), NOX3 and iNOS, FIG. 2.C. Cisplatin increased TRPV1, NOX3 and iNOS staining in the OC, SL, SV and SG, which with trans-tympanic capsaicin pretreatment blocked. Images shown are 20× and the insets were imaged at 100× by confocal microscopy. Scale bar is 100 µm. Data presented in FIG. 2.A represent the mean±S.E.M. of cochleae from four animals from each group. (*indicates statistically significant difference from vehicle; **indicates significant difference from the cisplatin group, p<0.05).

FIG. 4.A.-FIG. 4.B. FIG. 4.A. Capsaicin transiently activates STAT1 $Ser^{727}$ phosphorylation in UB/OC-1 cells. UB/OC1 cells treated with either capsaicin (2.5 µM) or cisplatin (2.5 µM) and harvested in a time dependent manner. Capsaicin treatment caused a transient increase of p-STAT1 at 45-60 minutes and reached baseline by 120 minutes. FIG. 4.B. Cisplatin treatment caused a more prolonged increase lasting till 120 minutes. *indicate statistically significant difference from 0 min (p<0.05); (n=4).

FIG. 5.A. and FIG. 5.B. UB/OC1 cells treated with capsaicin (2.5 µM) demonstrated significantly increased $Tyr^{705}$ p-STAT3 after 30 and 45 min (FIG. 5.A.). Cisplatin (2.5 µM) treatment suppressed the $Tyr^{705}$-p-STAT3 (FIG. 5.B.) in a sustained and significant manner at 120 minutes. FIG. 5.C. Capsaicin treatment significantly increased the ratio of p-STAT3/p-STAT1 in a transient manner at 45 minutes. FIG. 5.D. Cisplatin treatment persistently and significantly decreased the p-STAT3/p-STAT1 ratio. FIG. 5.E. and FIG. 5.F. UB/OC1 cells were pretreated with capsaicin (2.5 µM) for 30 minutes followed by cisplatin (2.5 µM) treatment for 45 minutes. Cisplatin increases p-STAT1 significantly, with no change in p-STAT3 phosphorylation, while capsaicin increased p-STAT1 and p-STAT3 significantly. Capsaicin+cisplatin treatment decreased p-STAT1 significantly with a concomitant significant increase in p-STAT3 activation. Graphical analyses of p-STAT3/p-STAT1 ratio indicates that cisplatin significantly decreased the p-STAT3/p-STAT1 ratio compared to control, capsaicin significantly increased p-STAT3/p-STAT1 ratio compared to cisplatin. Capsaicin+cisplatin group showed a significant increase in p-STAT3/p-STAT1 ratio compared to all the groups, possibly due to significant increase in p-STAT3 activation and significant decrease in p-STAT1 activation. FIG. 5.G. Mid-modiolar sections of cochleae from rats treated with sterile PBS, i.p (vehicle), capsaicin (20 mg/kg) or cisplatin (11 mg/Kg, i.p) for 72 hours were immunolabeled for $Ser^{727}$-p-STAT1 (green) or $Tyr^{705}$-p-STAT3 (red) and imaged using confocal microscopy (insets: 100× magnification). Cisplatin increased $Ser^{727}$-p-STAT1 staining at 72 h post administration, while capsaicin treatment did not alter p-STAT1 compared to control in the cochlea. Capsaicin (72 h) increased $Tyr^{705}$-p-STAT3 staining, while cisplatin (72 h) suppressed the $Tyr^{705}$-p-STAT3 staining. (*indicates statistically significant difference from 0 min or control cells, p<0.05; **indicates statistically significant difference from cisplatin, p<0.05; n=4, scale bar is 100 µm). FIG. 5.H. Graphical representation of p-STAT3/p-STAT1 ratio of the different cochlear regions as analyzed by image J software. FIG. 5.I. Cochlear gene expression by q-PCR indicates that cisplatin treatment increased the Bax/Bcl-2 ratio, which was abrogated by capsaicin pre-treatment.

-FIG. 6.B. FIG. 6.A. Capsaicin activates JAK2, while cisplatin decreases JAK2 phosphorylation. UB/OC1 cells treated with either capsaicin (2.5 µM) or cisplatin (2.5 µM) and harvested in a time dependent manner. Capsaicin treatment caused a robust increase of JAK2 at 45 minutes. FIG. 6.B. Cisplatin treatment decreased JAK2 phosphorylation in a sustained manner significantly. *indicate statistically significant difference from 0 min (p<0.05); (n=4).

-FIG. 8.D. FIG. 8.A. STAT3 is essential for capsaicin mediated protection and is TRPV1 independent. UB/OC-1 cells were pretreated with a selective inhibitor of STAT3 (STATTIC, 100 nM) for 45 min, followed by capsaicin (2.5 µM) for 45 min and then cisplatin (20 µM) for 48 h. The percentage of cell viability was assessed by MTS assay. Treatment of STATTIC (100 nM) alone did not induce cell death whereas treatment of cisplatin-induced significant cell death. Capsaicin (2.5 µM) protected against cisplatin (20 µM) induced cell death. However, pretreatment with STATTIC (100 nM) (or after the inhibition of STAT3) capsaicin could not protect against cisplatin-induced cell death. (*indicates statistically significant difference from control, p<0.05, n=8; **indicates statistically significant difference from cisplatin, p<0.05, n=8). FIG. 8.B. UB/OC-1 cells were pretreated with STATTIC (100 nM) for 45 min, followed by capsaicin (2.5 µM) for 45 min. Pretreatment of STATTIC inhibited the phosphorylation of $Tyr^{705}$ p-STAT3. (*indicates significant difference from control, p<0.05, n=4). FIG. 8.C. and FIG. 8.D. UB/OC-1 cells were pretreated with BCTC (100 nM) for 45 min followed by capsaicin (2.5 µM) for 45 min. Western blots show that inhibition of TRPV1 reduced the $Ser^{727}$ p-STAT1 (FIG. 8C) but not $Tyr^{705}$ p-STAT3 FIG. 8.D. Western blotting: All samples were loaded serially as depicted on the gel. The grouping of blots reflects the same blot re-probed with different antibodies. β-actin is used as loading control. None of the blots have lanes taken from different parts of the blot. Thick borders denote separate antibody probes for the same gel.

-FIG. 9.F. Cannabinoid Receptor CB2 activation is essential for capsaicin induced otoprotection. FIG. 9.A and FIG. 9.B. To determine the role of CB1 receptor in capsaicin induced cell survival, UB/OC-1 cells were pretreated with CB1 antagonist, AM281 (10 µM) for 30 min followed by capsaicin (2.5 µM) for 45 min. Western blots showed that inhibition of CB1 receptors (by AM281) did not affect either the capsaicin-mediated $Ser^{727}$ p-STAT1 (A) or $Tyr^{705}$ p-STAT3 (FIG. 9.B.). (*indicates statistically significant change from control, p<0.001, n=4). FIG. 9.C. and FIG. 9.D. To determine the role of CB2 receptor in capsaicin induced cell survival, UB/OC-1 cells were pretreated with CB2 antagonist, AM630 (10 µM) for 30 min followed by the capsaicin (2.5 µM) for 45 min. Western blots showed that inhibition of CB 2 receptors blocked the capsaicin-mediated $Ser^{727}$ p-STAT1 (C) and $Tyr^{705}$ p-STAT3 (FIG. 9.D.). (*indicates statistically significant change from control, p<0.001, n=4). FIG. 9.E. UB/OC-1 cells were pretreated with or without CB2 antagonist, AM630 (10 µM) for 30 min followed by CB2 agonist, JWH-015 (10 µM) for 30 min. Western blots showed CB2 agonist (JWH-015) increased $Tyr^{705}$ p-STAT3, and that inhibition of CB2 receptors (by AM630) reduced the JWH-015-mediated $Tyr^{705}$ p-STAT3 phosphorylation. Thus, this implicates CB2R in the protective signaling of STAT3. (*indicates statistically significant change from control, p<0.05, n=4). FIG. 9.F. UB/OC-1 cells were pretreated with AM630 for 45 min, followed by capsaicin (2.5 µM) for 24 h. Cell viability was assessed using MTS assay. Significant cell death occurred when cells were treated with CB2 antagonist, AM630 and capsaicin, implicating CB2 receptors in cell survival. (*indicates statistically significant change from control, p<0.05, n=4). Western blotting: All samples were loaded serially as depicted on the gel. The grouping of blots reflect the same blot re-probed with different antibodies. β-actin is used as loading control. None of the blots have lanes taken from different parts of the blot. Thick borders denote separate antibody probes for the same gel.

-FIG. 10.D. Capsaicin increased CB2 expression in UB/OC1 cells and in the rat cochlea. FIG. 10.A. UBOC-1 cells were treated with capsaicin (2.5 µM) for 24 h. Total protein was extracted and immunoblotting was performed for CB1 and CB2 receptors. B-actin was used for housekeeping and loading control. Capsaicin increased CB2 receptor staining. FIG. 10.B. *Cochleae* were harvested from rats treated with either oral PBS or oral capsaicin (20 mg/kg) for 24 h. Total RNA was harvested, converted to c-DNA and probed for CB2 receptor expression by q-PCR. GAPDH was used as housekeeping gene. Capsaicin treatment shows an increase in CB2 expression in the rat cochlea. FIG. 10.C. and FIG. 10.D. *Cochleae* were harvested from rats treated with PBS, fixed in 4% paraformaldehyde in PBS for 8 h. They were then decalcified in EDTA (10 mM), and mid modiolar sections of the *cochleae* were probed for the cannabinoid receptors subtypes, CB1 (FIG. 10.C.) and CB2 (FIG. 10.D.), while nuclei were stained with DAPI. Fluorescent images were obtained with a Leica confocal microscope. CB1 and CB2 immunoreactivity were seen in the IHCs, OHCs, stria vascularis and spiral ganglion cells of the basal turn of the rat cochlea. Magnification for OHC, spiral ganglion cells and stria vascularis (40×). Similar images were obtained from 3 different animals.

-FIG. 11.B. Cannabinoid receptors are expressed in the rat cochlea and CB2 receptor is integral to capsaicin mediated rescue of cisplatin-induced hearing loss. Male Wistar rats were treated with oral PBS (1 ml) or oral capsaicin (10 mg/kg) and collected the *cochleae* 72 h later. FIG. 11.A. Mid-modiolar sections of rat *cochleae* were immunoblotted for CB2R and imaged using confocal microscopy at 20× and 100×. CB2R expression was observed in outer hair cells (OHCs), supporting cells (SCs), spiral ganglion cells (SG) and in the stria vascularis (SVA). Scale bar is 25 µm. FIG. 11.B. Pretreated rats were pretreated with AM630 (0.1 µM, TT), CB2R antagonist for 1 hour, then capsaicin (20 mg/kg, 1 ml) by oral gavage 24 hours prior to cisplatin administration (11 mg/kg i.p.). After 72 hours, ABR threshold shifts were at 8, 16 and 32 kHz. Pretreatment with capsaicin (20 mg/Kg solution) by oral gavage significantly reduced the threshold shifts caused by cisplatin. CB2 receptor antagonist AM630 (TT) abrogated the capsaicin protection against cisplatin. AM630 (TT) alone also caused ABR threshold shifts. (* and ** indicate statistically significant increases from PBS and from cisplatin-treated animals, respectively, p<0.05, n=4).

-FIG. 12.J. Oral capsaicin pre-treatment does not affect cisplatin's chemotherapeutic ability in the SCID mouse xenograft model. Twenty seven SCID mice were injected with UMSCC-10b cells (1×10⁶ cells) subcutaneously and divided into four treatment groups: oral PBS+PBS (i.p, lml) (n=8), cisplatin (2 mg/kg, i.p) (n=7), oral capsaicin (0.5 mg/kg)+cisplatin (2 mg/kg, i.p) (n=7) and oral capsaicin alone (n=5). Drugs were administered by oral gavage and/or i.p injections every other day (three times a week), once the tumors were palpable, until the end of the study. Tumor growth was monitored closely. Oral capsaicin+Cisplatin and the cisplatin treated mice showed suppressed tumor size (FIG. 12.C, FIG. 12.D, FIG. 12.E, FIG. 12.F. and FIG. 12.I.) and tumor weight (FIG. 12.J.). Capsaicin treatment alone decreased tumor size and weight, but not significantly. Representative images of the tumor bearing mice and excised tumors at the end of the study from each group is shown in FIG. 12.A. -FIG. 12.H. Line graphs and histograms in FIG. 12.1 and FIG. 12.J represent mean±SEM from each treatment group. (*indicates statistically significant difference, p<0.05, from vehicle-treated mice).

FIG. 14.A.-FIG. 14.D. NIHL is associated with acute and chronic increase in the expression of pro-inflammatory cytokines. FIG. 14.A. Pre-treatment ABRs were performed on naïve Wistar rats, followed by noise exposure (OBN 122 dB, centered at 16 kHz for 1 h). Post treatment ABR thresholds were recorded 21 days after noise exposure. ABR threshold shifts of (25±4, 30±3 and 52±7 dB) at 8, 16 and 32 kHz respectively, demonstrates a permanent threshold shift. FIG. 14.B. SEM of the basal turn of cochlea showing damage to the outer hair cells (OHCs) from noise-exposure after 21 days. Arrows indicate damaged OHCs. Almost 50% of the OHCs show severe damage. FIG. 14.C. Graphical representation of the OHC damage seen by SEM. Noise damaged 43±4% of OHCs (n=6), compared to less than 5% OHC loss in untreated control condition. FIG. 14.D. Increased expression of stress response and inflammatory genes in NIHL. *Cochleae* were collected from rats at 48 h and 21d post noise exposure. Total RNA was extracted and converted into cDNA, and gene expressions for various genes were performed by Q-PCR. GAPDH was used as the housekeeping gene for normalization. Significant increase in all the genes were seen when compared to untreated control *cochleae*. * denotes statistically significant difference between noise exposed and control untreated cochlea.

-FIG. 15.M. TRPV1 mediated Ca2+ release by ROS is potentiated by TNF-α. To establish the role of TRPV1 channel in NIHL in vitro and to delineate the TNF-α potentiation of TRPV1 (Vanolloid Receptor 1—VR1) induced $Ca^{2+}$ pathway HEK cells stably transfected with VR1 (HEKVR1) and immortalized organ of *Corti* (UB/OC-1) cells were used. The cells were loaded with $Ca^{2+}$ dye-Fluo-4AM, washed and imaged every 3 seconds using Leica confocal microscope in a time series till 300 seconds. FIG. 15.A, FIG. 15.B, FIG. 15.C. and FIG. 15.D. Basal fluorescence was captured for 10 scans and 100 μM $H_2O_2$ was added at 30 seconds and the resulting fluorescence captured. $H_2O_2$ treatment elicited a rapid robust $Ca^{2+}$ response within 10 seconds with fluorescence returning to baseline by 60 seconds in the HEKVR1 cells (FIG. 15.A.), while a delayed $Ca^{2+}$ response at 30 seconds was seen in UB/OC-1 cells (FIG. 15.C.) that returned to baseline by 3 minutes, possibly due to the presence of fewer TRPV1 channels. However, pre-treatment with TNF-α (0.1 μg/ml) for 60 seconds prior to treatment with $H_2O_2$ causes a prolonged sustained calcium release in both HEKVR1 as well as UBOC1 cells that is observed till 5 minutes (FIG. 15.B. and FIG. 15.D.). Pictorial representation of baseline, maximal and fluorescence after 5 mins has been shown in HEKVR1 cells (FIG. 15.B.) and in UBOC1 cells (FIG. 15.D.). To determine the role of ERK phosphorylation in $H_2O_2$ mediated $Ca^{2+}$ release, UB/OC1 cells were pre-treated with 10 μM PD98059 (ERK inhibitor) which elicited little or no calcium release in both HEKVR1 as well as UBOC1 cells. FIG. 15.E, FIG. 15.F. $H_2O_2$ treatment causes ERK activation in UB/OC1 cells in a time dependent manner. UBOC1 cells were treated with 100 μM $H_2O_2$ and probed for ERK1/2 activation by western blotting. ERK activation was elicited in a time dependent manner, with highest expression seen at 60 minutes post treatment. Graphical representation is shown in (FIG. 15.F.). FIG. 15.G. $H_2O_2$ induced apoptosis is ERK dependent. UB/OC1 cells were pre-treated with ERK inhibitor PD98059 prior to treatment with 100 μM $H_2O_2$, which showed significantly decreased cell death by TUNEL. FIG. 15.H, FIG. 15.I. TNF-α (0.1 μg/ml) treatment elicits ERK activation in UB/OC1 cells. ERK activation by TNF-α (0.1p g/ml) treatment elicited a bell shape curve with highest expression seen at 30 minutes post treatment in UBOC1 cells. FIG. 15.J, FIG. 15.K. $H_2O_2$ or TNF-α mediated $Ca^{2+}$ response is TRPV1 dependent. UB/OC1 cells were treated with either scrambled siRNA or TRPV1 siRNA for 24 h. Inhibition of TRPV1 by transfection of UBOC1 cells with siRNA did not elicit a strong $Ca^{2+}$ response with either 100 μM $H_2O_2$ or 100 μM $H_2O_2$+TNF-α (0.1 μg/ml) (FIG. 15.J) and inhibited apoptosis by 100 μM $H_2O_2$ as seen by TUNEL staining (FIG. 15.K.). FIG. 15.L, FIG. 15.M. To determine the role of TNF-α in potentiating the $Ca^{2+}$ response via the TRPV1 channel, HEKVR1 cells were treated with a direct TRPV1 agonist (Capsaicin (2.5 μM)) and with TNF-α (0.1 μg/ml) for 30 minutes. A tremendous increase in $Ca^{2+}$ was observed with Capsaicin treatment (741±22%) over basal fluorescence, which was increased to 3146±532%, with the addition of TNF-α (FIG. 15.L, FIG. 15.M.). These data indicate that 1) TRPV1 is essential for increased $Ca^{2+}$ release seen in NIHL, and 2) accompanying inflammation by TNF-α potentiates this response and furthermore 3) this response is ERK dependent.

-FIG. 16.C. Capsaicin pretreatment abrogates NIHL and decreases "TNT triad" markers. Pre-treatment ABRs were performed, followed by oral capsaicin 24 h prior to noise exposure (122 dB OBN centered at 16 kHz for 1 h). Capsaicin was administered orally again on the day of NE and once more at 24 h, after noise exposure. Post treatment ABR threshold were recorded 21 days after noise exposure. FIG. 16.A. Noise exposure showed 25-45 dB threshold shift, which was abrogated by either intra-tympanic or oral capsaicin. *denotes statistically significant difference from the noise+vehicle group. Statistics were performed using ANOVA and Tukey's post hoc analysis, N=6. FIG. 16.B. Gene expression analyses of the various stress response, inflammatory and apoptotic markers by qPCR of the rat *cochleae* showed that oral capsaicin treatment inhibits the upregulation of all the stress markers by NE. Fold increases in gene expressions by NE over oral PBS treated control rat *cochleae* were as follows: TRPV1 (4.4±0.7), TNF-α (4.7±0.6), NOX3 (4.6±0.7), COX2 (3±0.2), Bax (3±0.1), while the oral Cap+NE group showed basal levels of gene expression where TRPV1 (0.85±0.2), TNF-α (0.9±0.1), NOX3 (0.5±0.2), COX2 (0.84±0.2) and Bax (0.86±0.1). Oral Capsaicin treatment alone showed basal levels of all genes namely: TRPV1 (0.9±0.1), TNF-α (1±0.15), NOX3 (0.7±0.2), COX2 (1±0.1) and Bax (0.69±0.1). FIG. 16.C. Immunolabeling for DAPI (blue), and TRPV1 (red) and TNF-α (green) was performed on day 21 post noise exposure. Noise increased TRPV1 and TNF-α immunoreactivity, which was significantly decreased by oral capsaicin pre-treatment. Scale bars represent 50 μm and 10 μm for insets.

-FIG. 17.D. Etanercept treatment prevents and treats NIHL. Pre-treatment ABRs were performed. FIG. 17.A. Pre-treatment paradigm: Subcutaneous (sc) or trans-tympanic (TT) administration of ETA 3 days or 7 days prior to noise exposure (OBN 122 dB, centered at 16 kHz for 1 h) was performed. Post treatment ABR thresholds were recorded 21 days after noise exposure. Post-treatment ABR thresholds were recorded 21 days after noise exposure. ABR threshold shift was measured. Noise trauma demonstrates a 25-60 dB elevation in hearing threshold. This increase in hearing threshold (hearing loss) was reduced to 5-10 dB by ETA pre-treatment. FIG. 17.B. Rescue paradigm: Noise exposure (OBN 122 dB, centered at 16 kHz for 1 h) was performed, and ETA treatment was rendered at 2 h or 24 h post NE (by either sc. or TT injections). Post treatment ABR thresholds were recorded 21 days after noise exposure. ABR threshold shift was measured. ETA rescue treatment by both routes of administration showed a significant decrease in threshold shifts when treatment was given at 2 h post NE. Subcutaneous delivery of ETA at 2 h post NE showed a threshold shift of (10-25 dB), while the TT route of delivery showed a (20-37.5 dB) threshold shifts. ETA when administered by the sc. route was observed to result in better rescue from NIHL than the TT route of delivery when administered at 24 h post NE. Thus ETA treatment helps in the prevention and treatment of NIHL. FIG. 17.C, FIG. 17.D. Cochleae harvested from the above rats were processed for gene expression studies by qPCR. Stress response genes such as TRPV1, NOX3 and inflammatory genes such as TNF-α, COX2, iNOS and pro-apoptotic Bax. Briefly, total RNA extracted from the cochlea, converted to cDNA and gene expression, was quantified by gene specific qPCR, GAPDH was used as the housekeeping gene. Prevention strategy: Noise exposure increased the expression of stress response and inflammatory genes significantly when compared to control cochleae. ETA pre-treatment at 3 days and 7 days ameliorated all these increases in gene expression seen in NIHL. FIG. 17.D. Treatment: Noise exposed male Wistar rats were treated with subcutaneous or TT ETA 2 h or 24 h post noise exposure. Significant increase in all the genes were seen in noise exposed cochleae when compared to untreated control cochleae. Significant decreases in inflammatory and stress response genes was seen with subcutaneous ETA treatment within 2 h. While most genes showed significant decrease when treated at 24 h post NE, the TRPV1 and TNF-α expression was not decreased by TT-ETA at 24 h, mirroring the ABR thresholds. **denotes statistically significant difference between noise exposed and control untreated cochlea and *denotes statistically significant difference between noise exposed and treatment groups.

-FIG. 18.B. Combined doses of capsaicin and ETA protected against NIHL. (FIG. 18.A). Rats were pretreated with oral vehicle or capsaicin (5 mg/kg) 24 h prior to noise exposure (122 dB OBN centered at 16 kHz for 1 h), followed by oral vehicle or capsaicin again on the day of NE and once more at 24 h after noise exposure. ETA (1 mg/kg) was administered 2 h following noise exposure. Post-treatment ABRs were performed 21 d following noise exposure and compared to pre-treatment values to determine threshold shifts Values are expressed as the mean±SEM of six rats per group. (FIG. 18.B). Wave 1 amplitude versus sound intensity plot demonstrates significant suppression by noise, partial restoration by pre-treatment with capsaicin or ETA and complete protection by suboptimal doses of the combination treatment of capsaicin and ETA when administered 4 weeks post NE. * indicate statistically significant differences in the noise-exposed rats ($p<0.01$).

-FIG. 19.C. Restoration of hearing following permanent NIHL using combined doses of capsaicin and ETA. FIG. 19.A.

FIG. 20.B. Rescue paradigm: noise exposed rats were evaluated for permanent threshold shifts at week 4. Treatment was started with oral capsaicin (5 mg/kg) for 3 days+single ETA (1 mg/kg s.c.) on day 2, for 3 weeks, followed by one wee of rest. Post treatment ABR threshold values were evaluated at week 8 after NE. Values are expressed as the mean+/−SEM of six rats per group. * indicate statistically significant differences the noise-exposed rats ($p<0.005$). Values are expressed as the mean+/−SEM of six rats per group.

FIGS. 23A-23C. Restoration of hearing following permanent NIHL using combination doses of capsaicin and ETA. FIG. 23A is a schematic representation of the experimental paradigm used in Example 10B. FIG. 23B is a graphical representation of ABR threshold shifts grouped according to treatments in accordance with Example 10B. FIG. 23C is a schematic representation of the systemic combination treatment of oral capsaicin and subcutaneous ETA used in Example 10B. Asterisk (*) denotes statistically significant difference compared to the sham control (untreated samples); ** denotes statistically significant difference compared to noise-exposed PTS groups at 4 weeks.

DETAILED DESCRIPTION

Figure 1A:
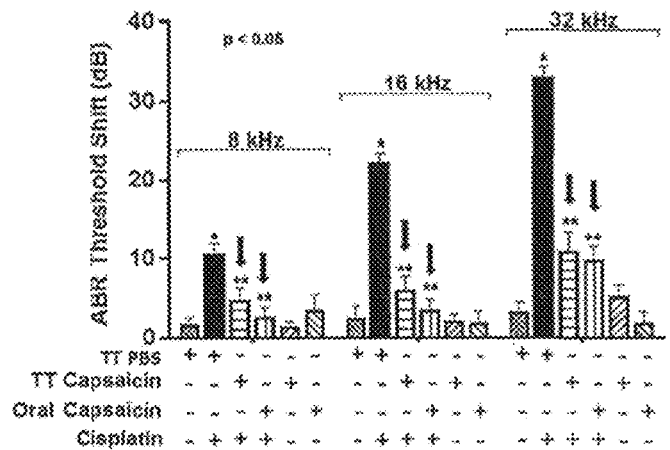
FIG. 1A. Capsaicin inhibits cisplatin-induced hearing loss ABR threshold shifts were recorded in Wistar rats pre-treated with either trans-tympanic capsaicin (0.1 μM, 50 μl) or PBS (50 μl), oral PBS or oral capsaicin (20 mg/kg), 24 h prior to cisplatin (11 mg/kg, i.p.). All post treatment ABR thresholds were measured at 72 h post cisplatin and they showed significant increase with cisplatin alone, which capsaicin attenuated at all frequencies tested. Black arrows indicate significant decrease in threshold shifts when compared to cisplatin. (*indicates significant difference from control; **indicates significant difference from cisplatin treatment, $p<0.05$, n=9).
Figure 1B:
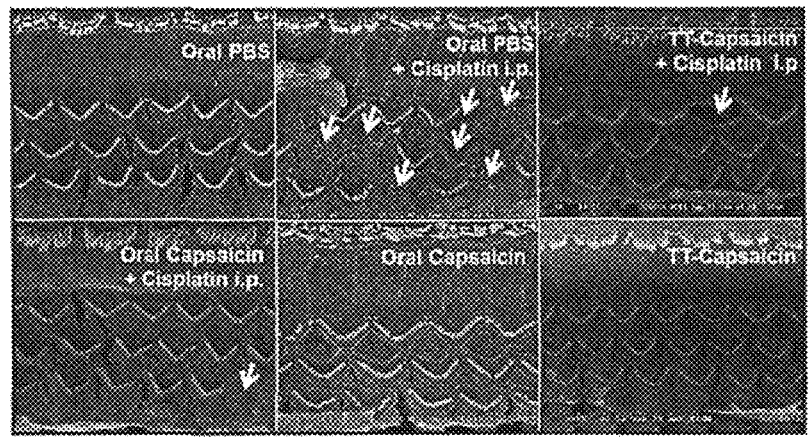
FIG. 1.A.
Figure 1C:
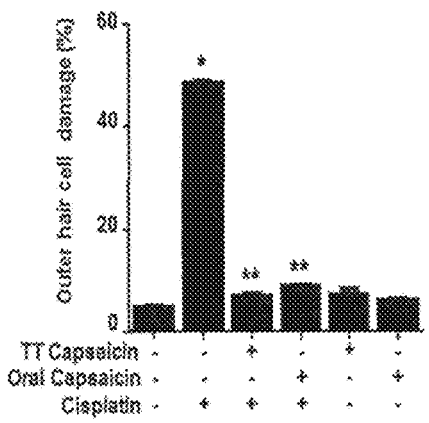
Figure 1D:
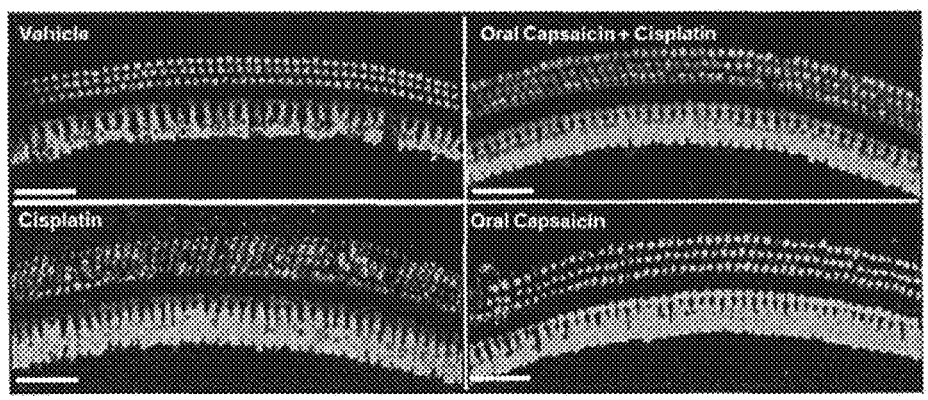
Figure 1E:
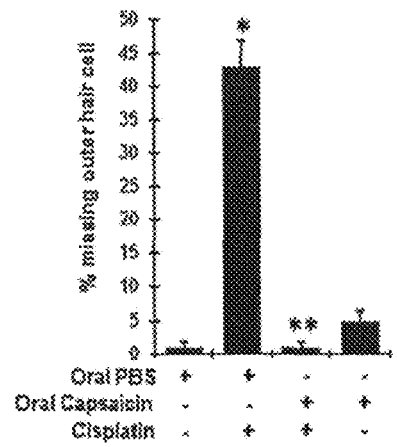

Unless defined otherwise, all technical and scientific terms used herein have the same meaning as commonly understood by one of skill in the art to which the disclosure pertains. Although any methods and materials similar to or equivalent to those described herein can be used in the practice or testing of the present technology, the preferred methods and materials are described herein.

Reference to an element by the indefinite article "a" or "an" does not exclude the possibility that more than one element is present, unless the context clearly requires that there be one and only one element. The indefinite article "a" or "an" thus usually means "at least one."

As used herein, "patient" or "subject" means an individual having symptoms of, or at risk for, cancer or other malignancy. A patient may be human or non-human and may include, for example, an animal such as a horse, dog, cow, pig or other animal. Likewise, a patient or subject may include a human patient including adults or juveniles (e.g., children). Moreover, a patient or subject may mean any living organism, preferably a mammal (e.g., human or non-human) from whom a blood volume is desired to be determined and/or monitored from the administration of compositions contemplated herein.

As used herein, "about" means within a statistically meaningful range of a value or values such as a stated concentration, length, molecular weight, pH, sequence identity, timeframe, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art. As used herein, the terms "subject" and "patient" are used interchangeably irrespective of whether the subject has or is currently undergoing any form of treatment.

As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human). Preferably, the subject is a human.

The term, otoprotective, as used in the description here, relates to preventing hearing loss, such as a loss in hearing that results from the loss of at least one auditory hair cell of the inner ear of the animal and/or subject having a reduced hearing capacity.

The term, otorestorative, as used in the description here, relates to restoring hearing loss by providing for the regeneration of at least one auditory hair cell of the inner ear of the animal and/or subject.

A "therapeutically effective amount" refers to an amount effective, at dosages and for periods of time necessary, to achieve the desired therapeutic result. A therapeutically effective amount of capsaicin and ETA may be determined by a person skilled in the art and may vary according to factors such as the disease state, age, sex, and weight of the individual, and the ability of the active agent(s) to elicit a desired response in the individual. A therapeutically effective amount is also one in which any toxic or detrimental effects of the active agent(s) are outweighed by the therapeutically beneficial effects. A therapeutically effective amount also encompasses an amount that is effective, at dosages and for periods of time necessary, to achieve the desired prophylactic (i.e., preventative) result.

As used herein, "pharmaceutically acceptable carrier, diluent or excipient" includes any and all solvents, dispersion media, coatings, antibacterial and antifungal agents, isotonic and absorption delaying agents, and the like that are physiologically compatible. Examples of pharmaceutically acceptable carriers, diluents and excipients include but are not limited to one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agent.

"Pharmaceutically accepted" is defined as not being toxic to living cells.

A "relatively low dose" or "low dosage amount" of an active ingredient (such as TNF-α inhibitor, a TRPV1 agonist, and any number of those active ingredients that fall within these groups of agents), may be described for purposes of the present disclosure as an amount of the active ingredient that is less than a previously recognized pharmaceutically active dose of the active ingredient, and may be referred to herein for descriptive purposes as a sub-optimal dose). However, in some cases and uses, while a dosage amount of an active ingredient may be observed to provide the pharmaceutical activity and/or hearing improvement physiological result described, greater dosage amounts of the active ingredient are not intended to be interpreted as negating or reducing the pharmacological activity and/or physiological effect (such as an improvement in a subject's hearing acuity) in a subject as described herein.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

A capsaicinoid, such as capsaicin, may be administered in any variety of forms. For example, it may be administered as part of an oral formulation. Alternatively, it may be administered as an inhalable preparation. Capsaicin may also be provided in an injectable preparation, such as an injectable preparation suitable for subcutaneous injection.

The following examples are presented to demonstrate preferred embodiments of the invention.

Example 1. Materials and Methods

Drugs and Reagents.

Cisplatin, capsaicin, STATTIC, and TRI reagent was purchased from Sigma-Aldrich (St. Louis, MO). CB1 antagonist, AM281, CB2 antagonist AM630, CB2 agonist JWH015 and BCTC was obtained from Tocris biotechnology (Minneapolis, MN). CellTiter 96® AQueous One Solution Cell Proliferation Assay was purchased from Promega (Madison, WI).

Antibodies Used and their Dilutions.

CB2 antibody (1:500) was purchased from Abcam Inc. (Cambridge, MA). CB1 (1:500), total STAT1 (1:1000), total STAT3 (1:1000), iNOS, NOX3, and TRPV1 (1:300) was purchased from Santa Cruz Biotechnology (Santa Cruz, CA). p-STAT1$^{Ser\ 727}$ (1:500), p-STAT3$^{Tyr\ 705}$ (1:500), p-JAK2 (1:1000) was purchased from Cell Signaling Technology Inc. (Danvers, MA). Secondary antibodies; goat anti-rabbit, donkey anti-goat and goat anti-mouse was purchased from Life Technology (Eugene, OR), and fluorescent tagged (dylight 488 and TRITC) secondary antibodies (1:500) from Jackson Immuno Laboratories (West Grove, PA).

Cell Culture.

UB/OC-1 cells, the immortalized organ of Corti cells derived from the mouse, were obtained from Dr. Matthew Holley (Institute of Molecular Physiology, Addison Building, Western Bank, Sheffield, UK). Cells were cultured in RPMI 1640 media supplemented with 10% Fetalclone II serum, and penicillin-streptomycin (1 ml/100 ml) and normocin (2 µl/ml). Cultures were grown at 33° C. in an incubator with 10% $CO_2$. Cells were passaged twice a week (1:3-4 media ratio). A head and neck cancer cell line was obtained from Southern Illinois University (SIU) School of Medicine (Springfield, IL, USA). Cancer cells were cultured in DMEM (HyClone) supplemented with 10% fetal bovine serum (Atlanta Biologicals Inc., Flowery Branch, GA, USA) and penicillin-streptomycin (Invitrogen).

Animals.

Adult male Wistar rats (200-350 g) (from Envigo) were used for this study. Rats were housed in a temperature controlled room with a twelve hour light/dark cycle. They had free access to commercial food and water provided by the SIU Laboratory Animal Care facility. Cisplatin is administered intraperitoneally at 11 mg/kg dose in the rat.

SCID mice (from Envigo, 5-6 weeks of age) were injected subcutaneously with $1.5 \times 10^6$ mycoplasma-free UMSCC 10B cells in one flank. When tumors reached palpable size (~100 mm3), attained in 10-15 days after injections, pretreated mice with oral PBS (vehicle) or oral capsaicin (0.5 mg/kg), each group was treated with intraperitoneal PBS or intraperitoneal cisplatin (2 mg/kg). Animals were subsequently treated with oral capsaicin, followed by intraperitoneal cisplatin, on alternate days three times per week for a total of 11 treatments. At the time of each treatment, tumor volumes were calculated based on the formula: volume=width2×(length/2) [Jajoo et al.]. Mice were killed 24 h after the eleventh treatment. All procedures were performed in accordance with relevant guidelines and regulations of SIU School of Medicine.

Auditory Brainstem Evoked Responses (ABRs).

Prior to experiments, rats were anesthetized with ketamine HCl/xylazine mixture (24.6/3 mg/kg) and then placed in a sound-attenuation chamber (Industrial Acoustic Company, Inc.). Body temperature of the rats was maintained at 37° C. with an animal blanket system. Pretreatment auditory brainstem responses (ABRs) was performed using an IHS-High-frequency System (Intelligent Hearing Systems, Miami, FL). The rats were exposed to acoustic stimuli via HIS transducers that were directly placed at the entrance of the ear canal. ABR thresholds were obtained for 5 ms duration tone bursts at 8, 16 and 32 kHz at a rate of 50/s. Thresholds were determined by visually produced lowest intensity evoked potentials (EP) that progressed in 10 dB steps. Evoked potentials (Eps) were amplified to 200,000×, and were band pass filtered (100-3000 Hz) and averaged over 1024 sweeps [Mukherjea et al., 2010].

Post treatment ABRs were performed 72 h following cisplatin administration. At the end of auditory testing, the anesthetized animals were decapitated and the cochlea harvested. The SIU Laboratory Animal Care and Use Committee approved all animal procedures.

Trans-Tympanic Injections.

Male Wistar rats were anesthetized using ketamine/xylazine cocktail. The tympanic membrane was punctured as described in [Mukherjea et al., 2010].

Cell Viability Assay (MTS Assay).

The in vitro UB/OC1 cell proliferation was performed by using the CellTiter 96® AQueous One Solution Cell Proliferation Assay Kit (Promega, Madison, WI), according to the manufacturer's instructions. 3,500 cells were seeded per well into a 96-well plate. Cells were pretreated with varying concentrations of capsaicin for 45 mins and cisplatin (20 µM) for 48 h. After 48 h, 20 µl of CellTiter 96 AQueous One Solution reagent was added to each well in 100 µl of total volume of media. Cells were incubated for 1 h, and recorded absorbance at 490 nm using an ELISA plate reader. The absorbance is directly proportional to the number of living cells and is expressed as a percent relative to vehicle-treated cells.

Processing of Cochlea for Immunohistochemistry.

Cochleae were perfused with a 4% paraformaldehyde solution, cochleae were decalcified for 7-10 days in 120 mM EDTA, embedded them in paraffin and then sectioned the specimens [Mukherjea et al., 2010]. Slides were deparaffined, rehydrated and then stained with primary and secondary antibodies. Glass coverslips were mounted on the specimens with ProLong Diamond mounting medium. Images were obtained using a Leica confocal microscope (Buffalo Grove, IL).

Fluorescent Intensity Analyses of Immunohistochemical Images.

Image J software was used to analyze the mean gray area for the various images. These values were then used to quantify the increase or decrease in % fluorescence intensity of the various regions of the samples compared to control.

Morphological Studies by Scanning Electron Microscopy (SEM) and Hair Cell Count.

Immediately after completion of post-treatment ABRs, rats were euthanized and their cochleae were harvested and the specimens processed as described previously by [Kamimura et al.]. Sputter-coated cochlea were viewed and photographed with a Hitachi S-500 scanning electron microscope (Hitachi Ltd.). The resulting scanning electron micrographs were examined to determine qualitative morphological characteristics in various regions including the basal, middle, and apical turns of the rat cochlea.

Hair cell counts were performed as described previously [Mukherjea et al., 2008]. Two representative areas of the basal turn, middle turn, and apex and hook portion were photographed. In each area, outer hair cells (OHCs) were counted in an area that was 10 pillar cell heads in length. The results are presented as the percentage hair cell damage per cochlear turn. At least three cochleae from different animals per treatment group were used.

Cochlear Whole Mount Preparation and Hair Cell Count.

To study the organization of the outer hair cells and inner hair cells, the cochlear whole mount technique was used. The cochleae was fixed in fresh 4% paraformaldehyde overnight, and then decalcified in 0.1 mM EDTA for 2 weeks, (pH 7.3) while stirring at room temperature for 2 weeks. After decalcification, the cochleae was microdissected into basal, middle, and apical turns for whole-mount preparation.

For further processing, segments were washed with 1×PBS twice for 5 mins. For blocking, the segments were incubated in 10% blocking serum (horse serum) for 3 hrs at room temperature. The segments were incubated with primary antibody in 0.2% Triton prepared in PBS and refrigerated overnight. The following day, the segments were washed in PBS (three washes) for 5 mins each wash. The segments were washed in secondary antibody for 2 hrs at room temperature in the dark. The antibodies were then washed with PBS (three washes). Glass coverslips were then mounted on the segments with ProLong Diamond Antifade Mountant (Thermo Fisher Scientific) and incubated them at room temperature overnight and then stored them in 4 degrees. Images were procured using a Leica confocal microscope (Buffalo Grove, IL).

For hair cell count in whole mount preparations, two to three random areas from the basal turn from each treatment group separately were selected. Hair cells were counted in 50 m and 25 m segments of the cochlea respectively. Counts were averaged across treatment group. This was further normalized as % of PBS (control) by taking the values of control as 100%.

RNA Isolation

RNA was isolated using RNeasy Mini Kit (Qiagen). Samples were obtained from the rat *cochleae* or UB/OC-1 cell cultures treatments by adding 1 ml TRIZOL reagent to 100 mg of each cochlea or 0.5 ml TRI reagent per well of each six-well plate as further described in [Mukherjea et al., 2008; Mukherjea et al., 2011].

Real-Time q-PCR 500 ng of total RNA was converted to cDNA using iScript cDNA Synthesis Kit (Bio-Rad). The reaction mixture was set up as follows: 4 μl of iScript reaction mix, 1 μl of iScript reverse transcriptase, 1 μg of total RNA and remaining amount of nuclease free water to bring the total volume to 20 μl. The reaction mix was incubated according to the cDNA protocol at the lab (25° C. for 5 min, 42° C. for 30 min and 85° C. for 5 min). The cDNA reaction mix was prepared for real-time PCR.

Real-time PCR was performed using Applied Biosystems StepOnePlus machine provided by the Research Imaging Facility (RIF) of SIU. PCR was set up as previously described in detail by [Mukherjea et al., 2010]. The primer sets were purchased from Sigma Genosys (St. Louis, MO), and were as follows:

```
Rodent-Bax (sense): 5'-ATGGCTGGGGAGACACCTGA-3'
(antisense): 5'-GCAAAGTAGAAGAGGGCAACC-3'

Rodent-Bcl2 (sense): 5'-CCTTCTTTGAGTTCGGTG-3'
(antisense): 5'-GAGACAGCCAGGAGAAAT-3'

Rodent-iNOS (sense): 5'-CATTCTACTACTACCAGATC-3'
(antisense): 5'-ATGTGCTTGTCACCACCAG-3'

Rodent-GAPDH (sense): 5'-ATGGTGAAGGTCGGTGTGAAC-3'
(antisense): 5'-TGTAGTTGAGGTCAATGAAGG-3'

Rodent NOX3 (sense): 5'-GTGAACAAGGGAAGGCTCAT-3'
(antisense): 5'-GACCCACAGAAGAACACGC-3'

Rodent-CB2 (sense): 5'- CTCGTACCTGTTCATCAGCAGC -3'
(antisense): 5'- CAGCAGGAAGATAGCGTTGGAG-3'

Rodent TRPV1 (sense): 5'- GGTGGACGAGGTAAACTGGA -3'
(antisense): 5'-GCTGGGTGGCATGTCTATCT -3'
```

Western Blot Analysis

At the end of the capsaicin and cisplatin treatment, UB/OC-1 cells were washed with ice cold 1×PBS with phosphatase inhibitor cocktail added immediately (1:2000 μl) added to it. Total cell lysates were prepared using ice-cold lysis buffer containing 50 mM Tris HCl, 10 mM $MgCl_2$ and 1 mM EDTA in the presence of protease inhibitors mixture and phosphatase inhibitor 1 (1:100) (Sigma, St. Louis, MO). The lysates were kept on ice for 5 min followed by centrifugation. The clear supernatant was transferred to a clean tube and discarded the pellet. The supernatant was mixed with 5× solubilization buffer with beta-mercaptoethanol (1:9), and heated on water bath at 95° C. for 6 min.

The samples were then resolved by SDS polyacrylamide gel electrophoresis using 12% gel as described previously by [Laemmli et al.]. Proteins were then transferred to nitrocellulose membranes, blocked in a 5% BSA solution in TBS (Tris-buffered saline) and refrigerated overnight with the primary antibody in 5% BSA in TBST (Tris-buffered saline, containing 0.15 Tween 20). The following day, after three washes in TBST, blots with secondary antibody were incubated in TBST for 1 h at room temperature. The blots were washed three times with TBST. The blot was imaged using Li—COR Odyssey, near-infrared imaging system. Densitometric analysis of the bands was performed by using Odyssey software. Individual phosphorylated bands were normalized to Total ERK, Total JAK2, Total INK, Total p38, Total STAT1. Total STAT3 and β-actin as a loading control. The percentage expression of phosphorylated proteins or other proteins was charted to compare the expression of different treatments.

For Western blotting, all samples were loaded serially as depicted on the gel. The grouping of blots reflect the same blot reprobed with different antibodies. β-actin is used as loading control. None of the blots have lanes taken from different parts of the blot. Thick borders denote separate antibody probes for the same gel.

Protein Determination

In order to load an equal amount of sample in each well of the gels, the level of protein in samples was determined by the Bradford assay [Bradford et al.] using bovine serum albumin to prepare standard curves. The amount of protein was calculated to add the exact same amount of proteins for all samples.

Statistical Analysis

Data was charted for visual clarification with values presented as mean±SEM. Parametric tests were performed such as Student's t-test or analysis of variance (ANOVA) followed by Tukey's post hoc test wherever appropriate in order to determine statistically significant differences among groups. Errors bars shown in the figures represent standard error of mean (SEM).

Example 2. Therapeutic Embodiments

The present example presents a number of particular therapeutic embodiments of the regimens, compositions, and methods of treatment of the disclosure.

Otoprotective and Otorestorative Compositions

One aspect of the present invention is directed to an otoprotective composition. An otoprotective composition comprises a low dose (sub-optimal) of capsaicin and ETA capable of preventing or reducing a level of hearing loss in a subject, from exposure to a ototoxic agent, including noise or a chemotherapeutic agent, or as a result of ageing. Treatment with the otoprotective composition provides for preventing or reducing the level of hearing loss in the animal compared to a level of hearing loss in an animal upon exposure to an otodestructive event without a treatment with the therapeutically effective amount of capsaicin and ETA.

As a otoprotective composition, treatment is provided as a pre-treatment to a subject, for example, prior to the exposure of a subject to an otodestructive event, such as, for example, before the subject is treated with a toxic agent (e.g., a chemotherapeutic agent), or will exposed to a loud and/or otodestructive level of noise, or even to a subject at risk of suffering a loss of hearing sensitivity associated with advancing age or disease.

TRPV1 Agonists—Capsaicinoid (Capsaicin)

TRPV1 agonists useful in the present invention include capsaicinoids, capsaicin analogs and derivatives, and other low molecular weight compounds (i.e., MW<1000) that agonize the TRPV1. Capsaicin can be considered the prototypical TRPV1 agonist. Capsaicin (also called 8-methyl-N-vanillyl-trans-6-nonenamide; (6E)-N-[(4-hydroxy-3-methoxyphenyl) methyl]-8-methylnon-6-enamide; N-[(4-hydroxy-3-methoxyphenyl) methyl]-8-methyl-(6E)-6-nonenamide; N-(3-methoxy-4-hydroxybenzyl)-8-methylnon tran-6-enamide; (E)-N-[(4-hydroxy-3-methoxyphenyl)methyl]-8-methyl-6-nonenamide) has the following chemical structure:

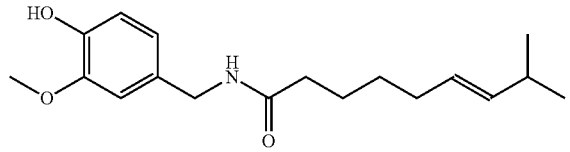 [SMILES: COc1cc(CNC(=O)CCCC/C=C/C(C)C)ccc1O]

In addition to capsaicin, a variety of capsaicin analogs and derivatives, and other TRPV1 agonists may be administered. Vanilloids, such as capsaicinoids, are an example of useful TRPV1 agonists. Exemplary vanilloids for use according to the invention include N-vanillyl-alkanedienamides, N-vanillyl-alkanedienyls, N-vanillyl-cis-monounsaturated alkenamides, capsaicin, dihydrocapsaicin, norhydrocapsaicin, nordihydrocapsaicin, homocapsaicin, and homodihydrocapsaicin.

In another embodiment, the TRPV1 agonist is a compound lacking the vanillyl function, such as piperine or a dialdehyde sesquiterpene (for example warburganal, polygodial, or isovelleral). In another embodiment, the TRPV1 agonist is a triprenyl phenol, such as scutigeral. Additional exemplary TRPV1 agonists are described in U.S. Pat. Nos. 4,599,342; 5,962,532; 5,762,963; 5,221,692; 4,313,958; 4,532,139; 4,544,668; 4,564,633; 4,544,669; 4,493,848; 4,532,139; 4,564,633; and 4,544,668; and PCT publication WO 00/50387. Other useful TRPV1 agonists include pharmacologically active gingerols, piperines, shogaols, and more specifically guaiacol, eugenol, zingerone, civamide, nonivamide, nuvanil, olvanil, NE-19550, NE-21610, and NE-28345 (see Dray et al., 1990, Eur. J. Pharmacol 181:289-93 and Brand et al., 1990, Agents Actions 31:329-40), resiniferatoxin, resiniferatoxin analogs, and resiniferatoxin derivatives (e.g., tinyatoxin). Any active geometric- or stereo-isomer of the forgoing agonists may be used.

Other TRPV1 agonists are vanilloids that have TRVP1 receptor-binding moieties such as mono-phenolic mono-substituted benzylamine amidated with an aliphatic cyclized, normal or branched substitution. Still other useful TRPV1 agonists for practicing the invention can be readily identified using standard methodology, such as that described in U.S. patent publication US20030104085. Useful assays for identification of TRPV1 agonists include, without limitation, receptor binding assays; functional assessments of stimulation of calcium influx or membrane potential in cells expressing the TRPV1 receptor, assays for the ability to induce cell death in such cells (e.g., selective ablation of C-fiber neurons), and other assays known in the art.

Mixtures of agonists and pharmaceutically acceptable salts of any of the foregoing may also be used. See Szallasi and Blumberg, 1999, Pharmacological Reviews 51:159-211, U.S. Pat. No. 5,879,696, and references therein. Various injectable formulations of capsaicin are described in the literature and known to those of skill in the art. The injectable formulation may typically contain water and one or more additional components to render the formulation optimally suited for injection into a subject.

When administering capsaicinoid according to methods described herein, the capsaicinoid is desirably administered in the form of a pharmaceutical composition formulated for oral administration, injection or to be inhaled.

As an oral preparation, the capsaicin will be provided, for example, as a capsule. The capsule will include a sufficient amount of the capsaicin such as to provide a dosage to the subject of about 1 mg/kg, or 2 mg/kg, or 3 mg/kg, or 4 mg/kg, or 5 mg/kg to about 6 mg/kg, or 7 mg/kg, or 8 mg/kg, or 9 mg/kg, or 10 mg/kg, or in some embodiments from about 4 mg/kg to 6 mg/kg, or about 5 mg/kg. In some regimens, this capsule form will be provided to the subject for 3 days, or 6 days, or 9 days. In an embodiment, the capsule form will be provided to the subject for a single set of 3 consecutive days, or two sets of three consecutive days, or three sets of three consecutive days, wherein, when the capsule is provided for two or more sets of three consecutive days, each set is separated by at least 3 days, or at least 4 days, or at least 5 days, or at least 6 days, or at least 7 days. A dosage of a TNF-α inhibitor, for example etanercept, would be provided at a dosage amount from about 0.5 mg/kg, or 0.75 mg/kg, or 1 mg/kg to 1.25 mg/kg, or 1.5 mg/kg on day 2, or in some embodiments from about 0.7 mg/kg, or 0.8 mg/kg, or 0.9 mg/kg, or 1.0 mg/kg to 1.1 mg/kg, or 1.2 mg/kg, or 1.3 mg/kg, or 1.4 mg/kg, or in further embodiments about 1.0 mg/kg, and for at least one set of three consecutive days of the regimen, or at least two sets of three consecutive days of the regimen, or all three sets of the three consecutive days of the regimen. This regimen will in some embodiments, be provided to a subject for 3 weeks. In a specific embodiment, capsaicin is administered on days 1, 2 and 3 of a given week, for three consecutive weeks, with a dosage of etanercept administered on day 2 of each of the three consecutive weeks. In some embodiments, the TNF-α inhibitor (e.g., etanercept) is formulated as a trans-tympanic injection, sub-cutaneous injections, or as an orally bioavailable formulation.

In other embodiments, the pharmaceutical composition formulated for injection of capsaicin is provided in an aqueous pharmaceutical composition. The capsaicinoid may be dissolved in oils, polyethylene glycol (PEG), propylene glycol (PG), and/or other solvents commonly used to prepare injectable or implantable solutions. Suitable pharmaceutically acceptable vehicles include aqueous vehicles, nonaqueous vehicles, antimicrobial agents, isotonic agents, buffers, antioxidants, suspending and dispersing agents, emulsifying agents, sequestering or chelating agents, and combinations or mixtures thereof. It is appreciated that when one or more solvents are used in the formulations of the invention, they may be combined, e.g., with a pharmaceutically acceptable buffer and may be present in the final formulation, e.g., in an amount ranging from about 10% to about 100%, more preferably from about 20% to about 100%.

Exemplary aqueous vehicles include Sodium Chloride Injection, Bacteriostatic Sodium Chloride Injection, Ringers Injection, Isotonic Dextrose Injection, Sterile Water Injection, Bacteriostatic Sterile Water Injection, Dextrose Lactated Ringers Injection and any combinations or mixtures thereof.

Exemplary nonaqueous parenteral vehicles that may be used for formulation include fixed oils of vegetable origin, cottonseed oil, corn oil, sesame oil, peanut oil, and combinations or mixtures thereof.

Exemplary antimicrobial agents in bacteriostatic or fungistatic concentrations include phenols, cresols, mercurials, benzyl alcohol, chlorobutanol, ethyl and propyl p-hydroxybenzoic acid esters, thimerosal, benzalkonium chloride, benzethonium chloride, and mixtures thereof.

Exemplary isotonic agents include sodium chloride, dextrose, and combinations or mixtures thereof. Exemplary antioxidants include ascorbic acid, sodium bisulfate, and combinations or mixtures thereof. Exemplary suspending and dispersing agents include sodium carboxymethylcellulose, hydroxypropyl methylcellulose, polyvinylpyrrolidone, any combinations or mixtures thereof. Exemplary emulsifying agents include anionic emulsifying agents (e.g., sodium lauryl sulfate, sodium stearate, calcium oleate, and combinations or mixtures thereof), cationic emulsifying agents (e.g., cetrimide), and non-ionic emulsifying agents (e.g., Polysorbate 80 (Tween 80)). Exemplary sequestering or chelating agents of metal ions include ethylenediaminetetraacetic acid (EDTA), citric acid, sorbitol, tartaric acid, phosphoric acid, and the like. Suitable surfactants include, but are not limited to, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations thereof. When one or more surfactants are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%. In certain other embodiments, a surfactant can preferably be combined with one or more of the pharmaceutically acceptable vehicles previously described herein so that the surfactant or buffering agent prevents the initial stinging or burning discomfort associated with capsaicinoid administration, as a wetting agent, emulsifier, solubilizer and/or antimicrobial.

Buffering agents may also be used to provide drug stability; to control the therapeutic activity of the drug substance (Ansel, Howard C., "Introduction to Pharmaceutical Dosage Forms," 4.sup.th Ed., 1985); and/or to prevent the initial stinging or burning discomfort associated with capsaicin administration. Suitable buffers include, but are not limited to, sodium bicarbonate, sodium citrate, citric acid, sodium phosphate, pharmaceutically acceptable salts thereof, and combinations thereof. When one or more buffers are utilized in the formulations of the invention, they may be combined, e.g., with a pharmaceutically acceptable vehicle and may be present in the final formulation, e.g., in an amount ranging from about 0.1% to about 20%, more preferably from about 0.5% to about 10%. In certain embodiments, the buffer is an acetate salt, phosphate salt, citrate salt; corresponding acids of the foregoing; and combinations or mixtures thereof.

In certain embodiments, the pharmaceutical vehicle utilized to deliver the injectable capsaicinoid may comprise about 20% PEG 300, about 10 mM histidine and about 5% sucrose in water for injection. In certain other embodiments, the pharmaceutical vehicle utilized to deliver the injectable capsaicinoid may comprise about 100% PEG 300. This may be used as such or further diluted in water for injection to achieve a larger volume.

The concentration of the active ingredient in the compositions provided as part of the described regimens and treatments are expected to vary depending on a number of criteria, including the specific agent being formulated, the route of administration, and other subject (patient) specific considerations (age, level of hearing loss, other medications/treatments). However, the injectable formulation may be further characterized, in some applications, according to the concentration of capsaicinoid in the formulation. In certain embodiments, the injectable formulation contains the capsaicinoid at a concentration ranging from about 1 ng/mL to about 100 mg/mL, about 1 mg/mL to about 100 mg/mL, about 1 mg/mL to about 50 mg/mL, about 10 mg/mL to about 50 mg/mL, or about 5 mg/mL to about 50 mg/mL.

In certain embodiments, the injectable formulation contains the capsaicinoid at a concentration ranging from about 1 ng/mL to about 10 mg/mL, and an amount of this formulation will be administered to the subject sufficient to provide an amount of capsaicin of 5 mg/kg., the volume of the injection being calculated based on the specific weight of the subject.

The injectable formulation may be further characterized according to the solvent present to dissolve the capsaicinoid. In certain embodiments, the solvent in the injectable formulation is a mixture of water and polyethylene glycol (e.g., polyethylene glycol having a number-average molecular weight of about 300 g/mol). The relative amounts of water and polyethylene glycol in the injectable formulation may be characterized. For example, in certain embodiments, the injectable formulation contains a mixture of water and polyethylene glycol (e.g., polyethylene glycol having a number-average molecular weight of about 300 g/mol) as solvent, wherein upon a volume basis there is 3-6 times more water than polyethylene glycol. In certain embodiments, the injectable formulation contains a mixture of water and polyethylene glycol (e.g., polyethylene glycol having a number-average molecular weight of about 300 g/mol) as solvent, wherein upon a volume basis there is 4-5 times more water than polyethylene glycol. In certain embodiments, the polyethylene glycol having a number-average molecular weight in the range of about 250 g/mol to about 350 g/mol.

The injectable formulation may be further characterized according to the volume of injectable formulation administered to the subject. In certain embodiments, the volume of injectable formulation administered to the subject is in the range of about 0.01 mL to about 100 mL, so as to provide an appropriate dosage of the capsaicin to the subject of about 1 mg/kg to about 5 mg/kg per day over the treatment regimen period.

In another aspect, an otorestorative composition is provided. An otorestorative composition comprises a therapeutically effective amount of capsaicin and etanercept capable of restoring a level of hearing, or improving a preexisting level of compromised hearing, in an otocompromised subject having less than a reference baseline hearing capacity. The otorestorative composition provides for an increase in hearing level in the otocompromised subject compared to the level of hearing in the otocompromised subject prior to treatment with the otorestorative composition. The otorestorative composition would be provided to the subject, for example, after a subject had been exposed to an otodestructive event, such as after exposure to a toxic agent (e.g., chemotherapeutic agent), an otodestructive level of noise, or both.

The otoprotective composition and otorestorative composition will in some embodiments, comprise a purified capsaicin and a purified etanercept, but may be utilized as unpurified components.

The otoprotective composition or otorestorative composition may be administered to a subject in need thereof that has been exposed to an otocompromising event, such as exposure to a toxic agent, noise, or a combination thereof. By way of example, the ototoxic agent may comprise a platinum-based chemotherapy agent, an aminoglycoside antibiotic, or a combination thereof. The otoprotective composition may be administered for preventing hearing loss.

Methods of Preventing Hearing Loss, Methods of Restoring Lost Hearing

Methods of preventing hearing loss are provided. In some embodiments, the method comprises administering an otoprotective regimen or combination of compositions to a subject before or during exposure to an ototoxic agent. Preventing hearing loss may comprise inhibiting damage to at least one auditory hair cell/synapse or ganglion of the inner ear of a subject. In these applications, a dosage of the capsaicin and a dosage of the TNFα inhibitor (such as ETA), will be provided to the subject before exposure to damaging noise or a chemical agent, or within 24 hours of having been exposed to damaging noise or a chemical agent, or any other potentially hearing impairing event.

Methods of restoring hearing loss are also provided. In some embodiments, the method comprises administering an otorestorative regimen or combination of compositions to a subject during or within a relatively short time after exposure to the ototoxic agent. The compositions will comprise an amount of capsaicin and an amount of ETA as described herein. These events may include exposure to loud noise, a chemical agent, or other hearing impairing event. Restoring hearing loss may comprise repairing damage to at least one auditory hair cell/synapse or ganglion of the inner ear of the subject.

The otoprotective compositions and the otorestorative compositions of the present invention may comprise a "therapeutically effective amount" of capsaicin and ETA.

The otoprotective and otorestorative compositions may further comprise a pharmaceutically acceptable carrier, diluent or excipient.

The subject in need of an otorestorative treatment may be a subject that had been exposed to or is in the process of being exposed to an ototoxic agent. The ototoxic agent may be a platinum-based chemotherapy agent, aminoglycoside antibiotic, or noise.

Method for otoprotective treatment of a subject. Preventing hearing loss may comprise administering the otoprotective composition to a subject before or during exposure to an ototoxic agent. Preventing hearing loss may comprise inhibiting damage to at least one auditory hair cell/synapse or ganglion of the inner ear of the subject. The method may include multiple treatments with the otoprotective composition, or a single treatment with the otoprotective composition. The particular treatment regimen may include a step wherein a single agent of the composition is administered to the subject prior to exposure of the subject to an ototoxic event, followed by administration of the otoprotective composition.

Method of restoring hearing loss. Restoring hearing loss may comprise administering the otoprotective regimens and/or combination of compositions during or after exposure to the ototoxic agent. Restoring hearing loss may comprise repairing damage to at least one auditory hair cell/synapse or ganglion of the inner ear of the subject. A dosage of the capsaicin and a dosage of the TNFα inhibitor (such as ETA), will be provided to the subject after exposure to damaging noise or a chemical agent, and preferably within 30 days of having been exposed to damaging noise or a chemical agent, or any other potentially hearing impairing event (such as disease, traumatic blow to the head, etc.). Restoring hearing loss may also comprise regenerating at least one auditory hair cell/synapse or ganglion of the inner ear of the subject.

Capsaicin and Cisplatin Induced Hearing Loss-Chemotherapy Treatment

Capsaicin is known to possess anti-inflammatory [Chen et al., 2003] and anticancer properties [Bessler et al; Yang et al.; Bhutani et al.]. Capsaicin has also been reported to ameliorate cisplatin-induced nephrotoxicity [Shimeda et al.; Jung et al.]. TRPV1 expression is reported to increase in the cochlea in cisplatin-mediated ototoxicity [Mukherjea et al., 2008]. Several studies have implicated TRPV1 in mediating entry of cisplatin and aminoglycosides into auditory hair cells [Mukherjea et al., 2008; Waissbluth et al.; Ta et al.]. Local administration of capsaicin by trans-tympanic injection produced temporary hearing loss [Mukherjea et al., 2011]. The transient nature of the capsaicin-induced hearing loss was examined by the present investigators. With the studies provided in the present disclosure, the present investigators have now discovered that capsaicin treatment may be used as a unique preconditioning stimulus to reduce damage to the cochlea produced by ototoxic drugs, such as cisplatin. These proposed capsaicin treatments are further combined with a low dosage of a TNFα inhibitor (such as ETA), in some embodiments, as a technique for preventing and/or rescuing hearing loss in a subject undergoing chemotherapy.

Both cisplatin and capsaicin activate TRPV1, and STAT1, but produce different downstream signaling pathways. Capsaicin produces a transient activation of STAT1 phosphorylation compared to a sustained STAT1 up-regulation following cisplatin treatment which leads to inflammation and apoptosis. Capsaicin also activates the pro-survival transcription factor $Tyr^{705}$ p-STAT3, whereas cisplatin decreases STAT3 phosphorylation. Thus, there seems to be a dichotomy in the downstream mechanisms activated by capsaicin versus cisplatin in the cochlea. The dichotomy of p-STAT3/p-STAT1 ratio was explored due to capsaicin treatment versus that of cisplatin and discovered that capsaicin increased the p-STAT3/p-STAT1 ratio. This tilted the ratio towards survival. By contrast, cisplatin reversed this ratio leading to cell death. Pre-treatment with capsaicin prior to chemotherapy (such as cisplatin), increases the p-STAT3/p-STAT1 ratio significantly. Thus, damage to the cochlea associated with cisplatin may be reduced and/or inhibited.

Some endocannabinoids appear to interact with TRPV1 in sensory nerves [Di Marzo et al.; Zygmunt et al.] and since the cochlea is a sensorineural organ, capsaicin was examined for activation of cannabinoid (CB) receptors in the cochlea.

CB2 agonists activate STAT3 and confer protection against oxidative damage in myocardial infarction [Han et al.]. The data here indicates that capsaicin increased the expression of cannabinoid receptor CB2 in the cochlea, and this leads to the activation of pro-survival $Tyr^{705}$ p-STAT3 transcription factor. The results of this study have significant translational implications for amelioration of cisplatin-induced hearing loss, and other conditions associated with inflammatory conditions.

Noise Induced Hearing Loss

Noise trauma is the most common cause of hearing loss in adults. There are no known FDA approved drugs for prevention or rescue of noise induced hearing loss (NIHL). Hearing loss induced by loud noise is associated with the generation of reactive oxygen species (ROS), increased Calcium ($Ca^{2+}$) in the endolymph and hair cells, and increased inflammation in the cochlea. Increased ($Ca^{2+}$) and ROS activity persists for several days after traumatic noise exposure (NE). Chronic increases in ($Ca^{2+}$) and ROS have been shown to increase inflammation and apoptosis in various tissues, but the role of $Ca^{2+}$ upregulation and the resulting inflammation causing a positive feedback loop in the cochlea to generate sustained toxic amounts of $Ca^{2+}$ are unknown.

Cochlear TRPV1 dysregulation is identified here to be a key step in NIHL and that TNF-α potentiation of TRPV1 induced $Ca^{2+}$ release is an essential mechanism of NIHL. In the Wistar rat model of NIHL, an acute (within 48 h) and a chronic (21 days) increase in cochlear expression TRPV1 (non-specific ligand gated cation channel), cochlear specific NADPH oxidase 3 (NOX3), pro-inflammatory mediators like tumor necrosis factor-α (TNF-α), cyclooxygenase-2 (COX2) and proapoptotic moiety Bax is seen. NE, mimicked by 100 μM $H_2O_2$ in vitro, elicits a robust $Ca^{2+}$ release which is prolonged by addition of TNF-α via the TRPV1 channel with the involvement of ERK phosphorylation. In addition, mitigation of NIHL can be mediated by: 1) desensitization of TRPV1 channel by oral capsaicin pretreatment, or 2) by inhibition of TNF-α by administration of FDA approved drug etanercept (ETA) (TT or subcutaneous (sc)) either pre NE or when administered within 24 hrs of NE will rescue from NIHL. These results demonstrate the central role of inflammation mediated by TNF-α potentiating TRPV1 response in the noise exposed rat cochlea. Hence, the regimens and techniques disclosed herein provide a method for improving hearing acuity in a subject suffering from noise induced hearing loss.

Combination Treatment and Regeneration

Hearing loss induced by loud noise is associated with the generation of reactive oxygen species (ROS) [Turner et al.; Evans et al.], increased $Ca^{2+}$ in the endolymph and hair cells [Ohlemiller et al.; Yamane et al.] and corresponding increased inflammation [Hu et al., 2002; Yamashita et al.] in the cochlea. Increased $Ca^{2+}$ and ROS activity persist for several days after traumatic noise exposure (NE) [Bohne et al., 1976; Ramkumar et al.; Murai et al.]. Chronic increases in $Ca^{2+}$ and ROS have been shown to increase inflammation and apoptosis in various tissues [Bohne et al., 2007; Banfi et al.; Pouyatos et al.; Mukherjea et al., 2008]. However, the precise roles of ROS, $Ca^{2+}$ and inflammatory cytokines (especially TNF-α) in mediating NIHL have not been clearly defined. The primary source of ROS in the cochlea is the NOX3 isoform of NADPH oxidase [Banfi et al.] which is activated by noise [Ramkumar et al.,] and which contributes to further induction of NOX3 expression [Pouyatos et al.; Mukherjea et al., 2008]. The existence of a positive feedback loop between ROS and NOX3 appears to exist. Thus, scavenging ROS by lipoic acid could block the subsequent induction of NOX3 participation and contributes to reduction in NIHL [Mukherjea et al., 2010]. ROS induces the expression of a number of genes in the cochlea, including the NADPH oxidase, NOX3, transient receptor potential vanilloid 1 (TRPV1) channel, and inflammatory cytokines, such as TNF-α [Mukherjea et al., 2010]. Knockdown of TRPV1 by short interfering (si) RNA reduces cochlear inflammation, damage to cochlear hair cells and cisplatin induced hearing loss in rats. These data suggest that TRPV1 is an essential mediator of cochlear inflammation and hearing loss [Pouyatos et al.]. Similarly, knockdown of cochlear NOX3 reduces cisplatin ototoxicity in the rat by reducing TRPV1 expression [Mukherjea et al., 2008]. The present data of the inventors supports a coordinated regulation of TRPV1 and NOX3 [Mukherjea et al., 2011] in cisplatin-induced inflammation and ototoxicity. The inflammatory response is mediated in part through activation the transcription factor, signal transducer and activator of transcription 1 (STAT1). Noise represents a similar trauma to the cochlea as cisplatin, and therefore NIHL is mediated by the interplay among these factors.

As validated herein, noise trauma is shown to activate an inflammatory process regulated by a coordinate activation of TRPV1, NOX3 and STAT1, which contributes to hearing loss. TNF-α is an early mediator of NIHL [Fujioka et al., 2006; Tan et al.]. Inflammation serves an important trigger for hearing loss [Kanzaki et al.]. Corticosteroids protect against sensorineural hearing loss. Increases in inflammatory markers (such as iNOS) within 2 h of noise trauma, followed by induction of TRPV1 and NOX3 and inflammatory mediators (COX2, TNF-α) at 48 h (FIG. 14) are demonstrated here to occur.

The role of TRPV1 in cochlear physiology has been examined by the Nuttall group. It was reported that capsaicin produced an increase in cochlear blood flow in the guinea pig, mediated by activation of TRPV1, release of substance P and nitric oxide [Vass et al., 1994; Vass et al., 1995b]. Subsequent studies showed the existence of TRPV1, TrkA and substance P immunoreactivity in neurons and vestibulo-basilar artery [Vass et al., 1995a]. These investigators also report that infusion of capsaicin or resiniferatoxin (RTX) into the scala media elevated the thresholds of the auditory nerve compound action potential, reduced cochlear microphonics and electrically evoked otoacoustic emissions [Zheng et al.]. Also reported is a desensitization of these responses with prolonged infusion of capsaicin or RTX. Wu et al. report that high concentrations of capsaicin (300-600 μM) blocked $K^+$ conductance and electromotility of guinea pig OHCs, independent of TRPV1 activation.

It has been observed that these channels are induced by oxidative stress mediated by activation of a Rac1/NADPH oxidase pathway. ROS induction of these channels in the inner ear by cisplatin contributes to hearing loss [Mukherjea et al., 2008]. Based on these reports, direct activation of TRPV1 by capsaicin may produce hearing loss. However, contrary to this, the present investigators found that transtympanic administration of capsaicin into the rat cochlea produced only transient hearing loss within 24 h of application, which recovered by 72 h [Mukherjea et al., 2011]. This transient phase of hearing loss was associated with increased expression of NOX3, TNF-α, recruitment of CD14 positive immune cells and activation of signal transducer and activator of transcription 1 (STAT1) [Mukherjea et al., 2011]. Surprisingly, the hearing loss was not associated with apoptosis of OHCs or induction of apoptotic mediators such as p53.

Figure 22:
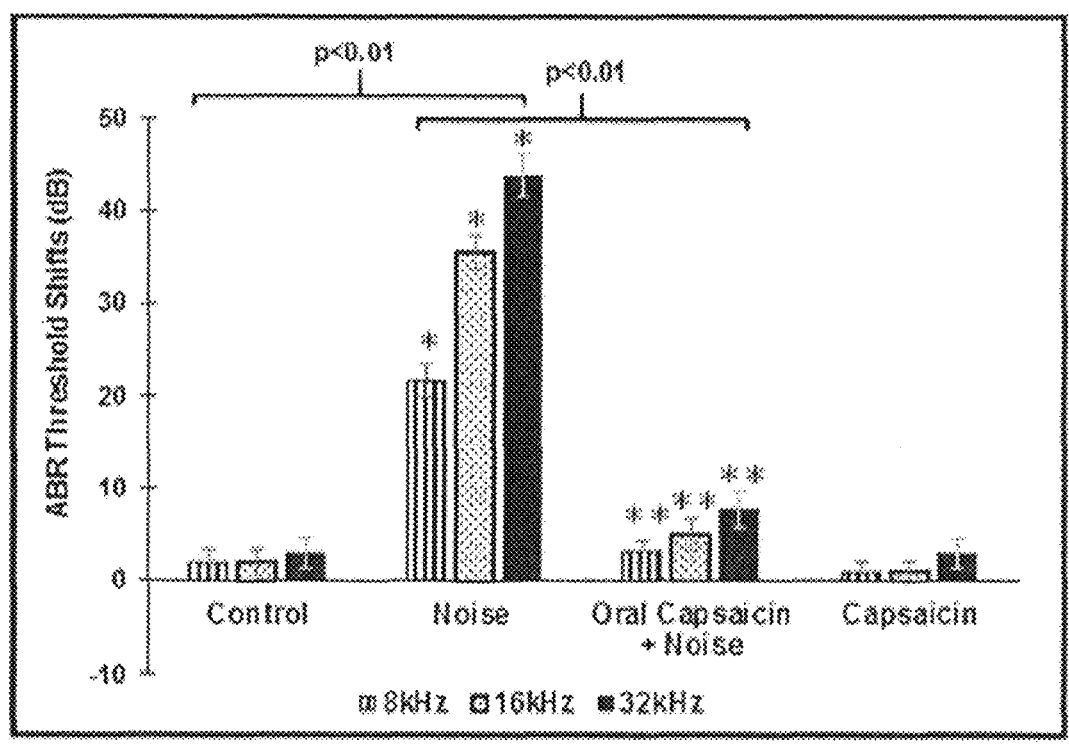
FIG. 22. Capsaicin pretreatment abrogates NIHL. Pre-treatment ABRs were performed, followed by oral capsaicin 24 h prior to NE. Capsaicin was administered orally again on the day of NE and once more at 24 h after NE. Post treatment ABR threshold were recorded 21 days after NE. NE showed 25-45 dB threshold shift, which was abrogated by either intra-tympanic or oral capsaicin. Asterisk (*) denotes statistically significant difference from the noise+vehicle group (ANOVA and Tukey's post hoc analysis, N=6).

Capsaicin may serve as a preconditioning stimulus which protects against subsequent acoustic trauma. Data presented here (FIG. 22) demonstrates that capsaicin pretreatment protects against NIHL. These findings implicate STAT1 and NOX3 in mediating the transient hearing loss produced by capsaicin. Transient hearing loss produced by capsaicin results from desensitization of TRPV1. This was reportedly observed by Zheng et al., with subsequent uncoupling of TRPV1 from the regulation of STAT1 and NOX3 pathways. This property of capsaicin serves as the basis of its utility to treat diabetic peripheral neuropathy. Alternatively, capsaicin could activate non-canonical alternative signaling pathways via G protein coupled receptors, such as cannabinoid receptors. Acharya et al. report cytoprotection from inflammatory bowel diseases. The desensitization and/or preconditioning property of capsaicin may be exploited to treat NIHL.

TNF-α is an important mediator of NIHL. Noise exposure increases production of TNF-α and other cytokines in the cochlea [Fujioka et al., 2006]. This is significant because it has been demonstrated that active inflammatory cells from the circulation migrate into the cochlea of mice after acoustic trauma [Hirose et al,]. Increased expression of TNF-α in the cochlea in noise-exposed rats has also been demonstrated [Bas et al.]. The local immune cells participate in the initial immune response to noise which could subsequently enhance recruitment of immune cells from the peripheral circulation. In vitro data in an organ of Corti-derived cell model (UB/OC1) and human embryonic kidney (HEK) cells stably transfected with TRPV1 show that oxidative stress (mediated by $H_2O_2$) increases $Ca^{2+}$ accumulation. This function was potentiated by TNF-α, acting via activation of ERK1/2 (FIG. 15). Furthermore, TNF-α reduced the ability of TRPV1 to desensitize, suggesting that it enhances $Ca^{2+}$ accumulation within the cell. A synergy between TRPV1 and TNF-α appears to exist, and provides that targeting TRPV1 and/or TNF-α receptor for inhibition will serve as an effective strategy for treating NIHL.

A "TNT triad" mechanism of NIHL is presented here with a focus on dysregulation of TRPV1 channels, cochlear specific NADPH oxidase NOX3 expression and TNF-α-mediated inflammation and cell death. A three pronged approach for treating NIHL is provided here that combats the three elements of this "TNT triad". The first prong of the treatment provides for the use of capsaicin (TRPV1 agonist) to precondition the cochlea and decrease prolonged inflammation. The second prong of the treatment utilizes etanercept (ETA) to inhibit cochlear TNF-α. The third prong of the treatment combines providing a composition of capsaicin and etanercept to the subject, to effect greater control of cochlear inflammation by reducing the synergy between TRPV1 and TNF-α.

Example 3. Hearing Restorative and/or Regenerative Treatment—Rescue from Complete Hearing Loss in a Subject—Capsaicin Alone Capsaicin provides a preconditioning stimulus which protects against subsequent acoustic trauma, and is shown here to protect against hearing loss. Data presented herein demonstrates that capsaicin pretreatment protects against NIHL (FIG. 23) These findings implicate STAT1 and NOX3 in mediating the transient hearing loss produced by capsaicin. Transient hearing loss produced by capsaicin results from desensitization of TRPV1. This was reportedly observed by Zheng et al., with subsequent uncoupling of TRPV1 from the regulation of STAT1 and NOX3 pathways. This property of capsaicin serves as the basis of its utility to treat diabetic peripheral neuropathy [Derry et al.]. Alternatively, capsaicin could activate non-canonical alternative signaling pathways via G protein coupled receptors, such as cannabinoid receptors. Acharya et al report cytoprotection from inflammatory bowel diseases. This desensitization and/or preconditioning property of capsaicin may be exploited to treat NIHL.

Example 4. Capsaicin Protects Against Cisplatin Ototoxicity by Changing the STAT3/STAT1 Ratio and Activating Cannabinoid (CB2) Receptors in the Cochlea Capsaicin Protects Against Cisplatin Ototoxicity.

ABRs in naïve adult male Wistar rats prior to treatment was first assessed with either trans-tympanic (TT) vehicle or capsaicin (0.1p M in 50 µl). Twenty-four hours later, cisplatin was infused (11 mg/kg) intraperitoneally (ip) and determined post-treatment ABRs 72 h later to assess hearing loss. Trans-tympanic administration of vehicle (sterile PBS in a volume of 50 µl) produced negligible changes in ABR threshold compared to naïve controls. ABR threshold shifts 72 h following cisplatin administration showed significant elevation. TT-Capsaicin (50 µl of a 0.1 µM solution) pretreatment 24 h prior to cisplatin significantly reduced ABR threshold shifts produced by cisplatin at all three frequencies tested (8, 16 and 32 kHz) (FIG. 1.A.). TT-Capsaicin administered alone did not significantly alter ABR thresholds, compared to trans-tympanic vehicle-treated rats after 72 h.

The efficacy of oral capsaicin for preventing cisplatin ototoxicity was tested. Oral capsaicin was effective in ameliorating cisplatin-induced hearing loss when administered 24 h prior to cisplatin. A dose dependent reduction in cisplatin-induced ABR threshold shifts was observed. Capsaicin doses were 5, 10 or 20 mg/kg. Significant protection against cisplatin hearing damage was observed in rats administered 10 or 20 mg/kg (FIG. 1.A.). The lowest dose of capsaicin tested (5 mg/kg) did not protect against cisplatin-induced ABR threshold shifts. Capsaicin administered by either trans-tympanic injection or by oral gavage alone did not significantly alter ABR threshold, when assessed 72 h later.

Scanning electron microscopic (SEM) images of the basal turn of the cochlea obtained from the rats treated above showed significant morphological changes in the stereociliary bundles on the outer hair cells (OHCs) indicating damage to the OHCs in the cisplatin group (FIG. 1.B.). In these studies, cisplatin produced a ten-fold greater loss or damage of outer hair cells compared to vehicle controls. Rats pretreated with trans-tympanic capsaicin had no significant loss of outer hair cells compared to vehicle controls. Oral capsaicin also significantly reduced stereociliary damage induced by cisplatin. Graphical representation of the data is shown in (FIG. 1.C.). Whole mount images of cochleae from similar groups of rats were stained with a polyclonal antibody against myosin VIIa, a hair cell-specific marker. These images supported the SEM findings, wherein cisplatin-induced hair cell loss was significantly decreased by capsaicin pre-treatment (FIG. 1.D), the arrows indicative of missing OHCs). Quantitative analyses of hair loss indicates that cisplatin-induced outer hair cell death was 43±4%; rats pretreated with oral capsaicin prior to cisplatin demonstrated no significant outer hair cell loss compared to control. Oral capsaicin alone produced minimal hair cell damage (FIG. 1.E.). Capsaicin is demonstrated here to alleviate cisplatin-induced hearing loss and OHC damage administered locally or orally.

Capsaicin Reduces Cochlear Oxidative Stress and Inflammatory Genes Induced by Cisplatin.

Figure 2A:
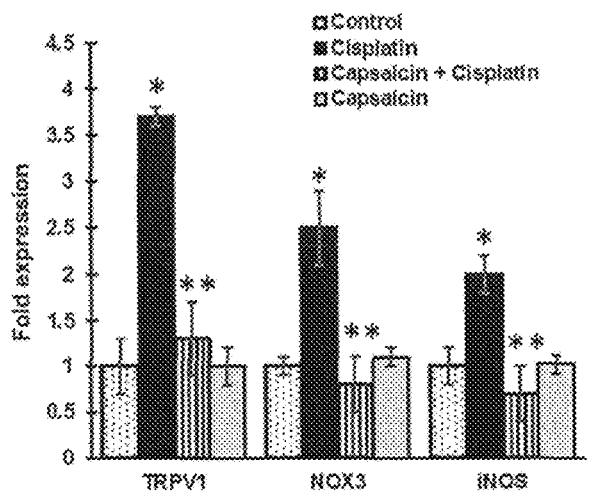
FIG. 2.A.
Figure 2B:
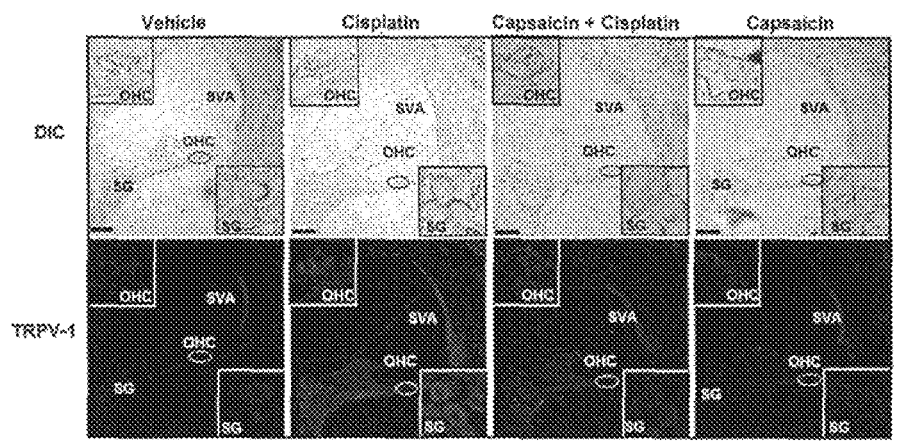
Figure 2C:
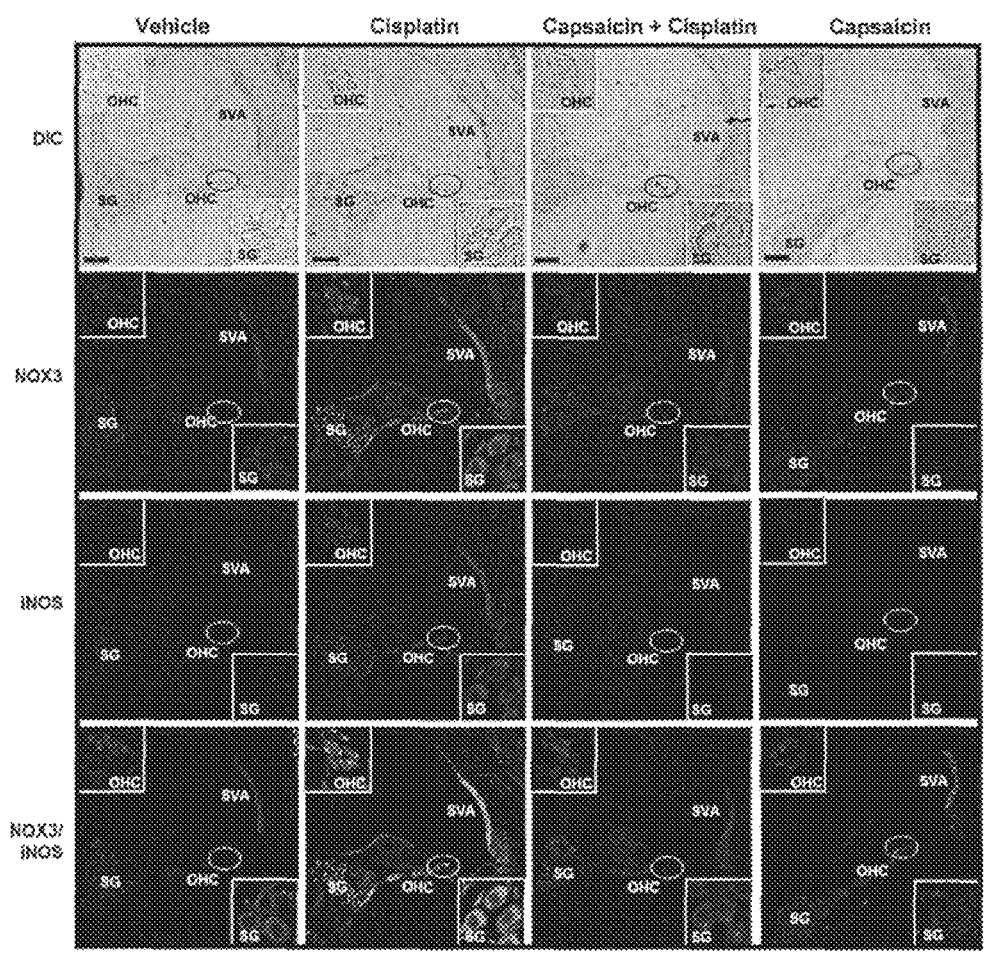
Figures 3, 4A, 4B:
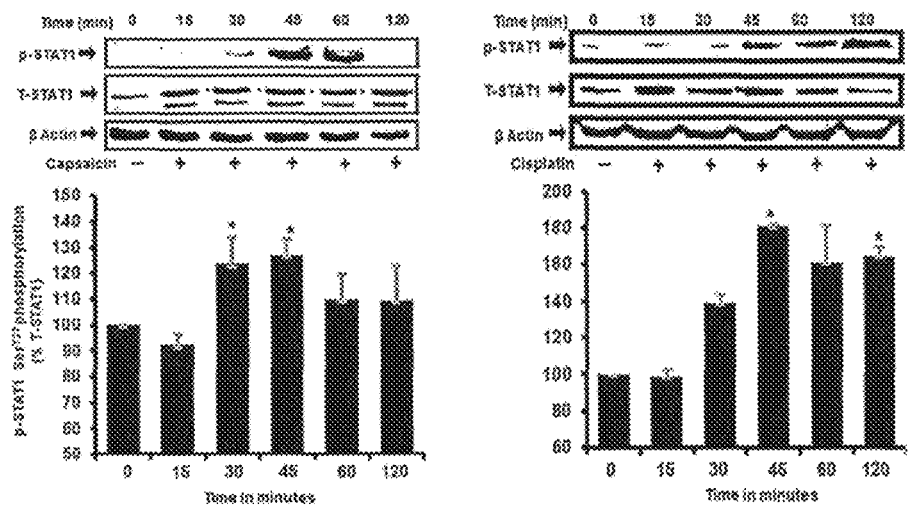
FIG. 3. Capsaicin pretreatment decreases cisplatin-induced stress response as shown by fluorescent intensity analyses of stress response immune reactivity in rat cochlea. Mid-modiolar sections of rat cochlea were probed with TRPV1, NOX3 or iNOS antibodies and imaged using confocal microscopy. Fluorescent intensity analyses of the images were performed using Image J software. Mean gray values for each region were then used to quantify the increase or decrease in % fluorescence intensity of the various regions of the samples compared to control. Fluorescent intensity analyses represented as % increases or decreases compared to baseline control images (p<0.05, *significant difference compared to control, **significant difference compared to cisplatin).

Cisplatin increased the expression of several cochlear oxidative stress and inflammatory genes. These genes regulate different cellular pathways which culminate in the death of OHCs and other cells of the cochlea, leading to hearing loss [Mukherjea et al., 2011; So et al.; Fujioka et al., 2014; Tornabene et al.]. Capsaicin was examined to determine if regulate genes linked to cochlear inflammation, such as TRPV1, NOX3 and iNOS. Real time quantitative PCR studies of the *cochleae* 72 h following cisplatin administration indicate 2-3 fold increases in TRPV1, NOX3 and INOS expression. Rats pretreated with TT-capsaicin 24 h prior to cisplatin administration demonstrated significant reduction in the expression of these genes to control levels. Capsaicin administration alone did not significantly change the expression of these genes (FIG. 2.A.). These data suggest an anti-inflammatory role of capsaicin in the cochlea when combined with cisplatin. Gene expression in mid-modiolar sections of the rat cochlea was further examined by immunolabelling for TRPV1, NOX3 and iNOS proteins. Cisplatin increased TRPV1, NOX3 and iNOS immunoreactivity in the organ of *Corti* (OC), spiral ligament (SL), spiral ganglions (SG) and marginal cells of stria vascularis (SVA) compared to control. Capsaicin pre-treatment prevented this increase (FIGS. 2.B. and 2.C.). Fluorescent intensity analyses performed using image J software revealed that cisplatin significantly increased TRPV1, NOX3 and iNOS labelling in the OHCs, SG and SVA compared to control. Capsaicin pre-treatment significantly decreased the expression of these proteins induced by cisplatin, while capsaicin treatment alone did not produce significant change compared to control (FIG. 3.). These data provide additional support for an anti-inflammatory role of capsaicin against cisplatin in the cochlea.

Example 5. Capsaicin Treatment Changes S-STAT3/P-STAT1 Dynamics During Cisplatin Insult Capsaicin stimulates the $Ser^{727}$ phosphorylation of STAT1, which is linked to transient inflammation in the cochlea and temporary hearing loss [Mukherjea et al., 2011]. Recovery from the transient hearing loss involves resolution of the initial inflammatory response. Capsaicin administration is linked to activation and/or inhibition of STAT3 phosphorylation in cancer cells [Bessler et al.; Yang et al.; Bhutani et al.]. The significance of these findings to cochlear cells under physiological conditions is unclear.

Figure 5A:
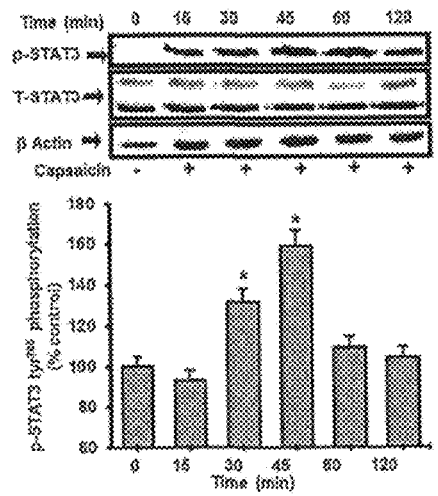
FIG. 5.A-FIG. 5.H. Capsaicin activates both STAT1 and STAT3, while cisplatin activates STAT1 and suppresses pro-survival STAT3.
Figure 5B:
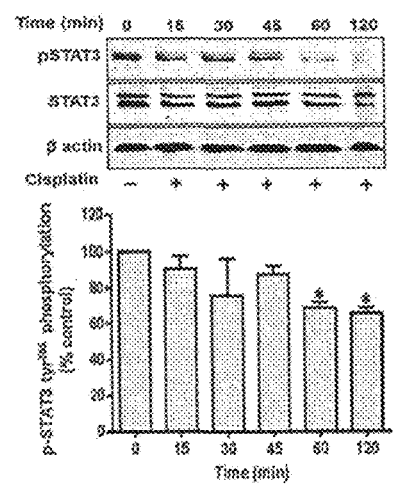
Figure 5C:
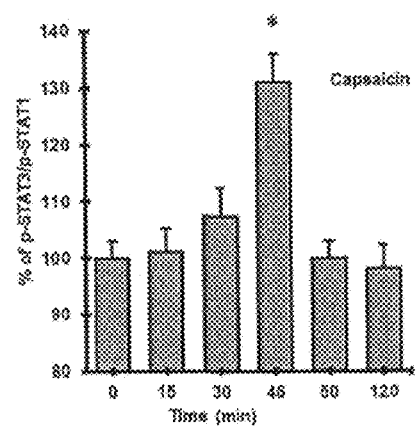
Figure 5D:
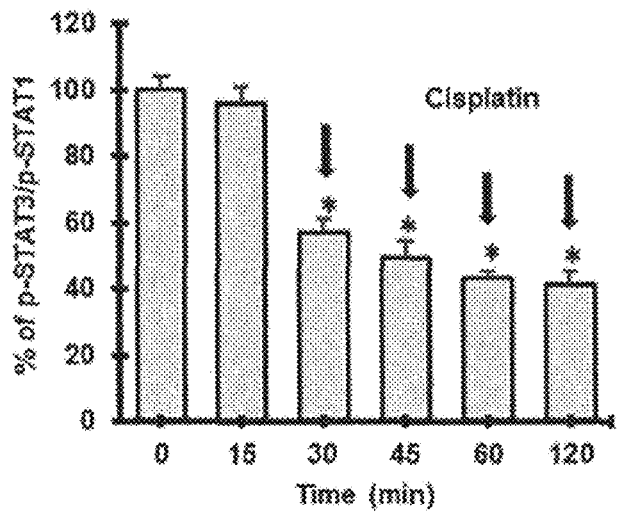
Figure 5E:
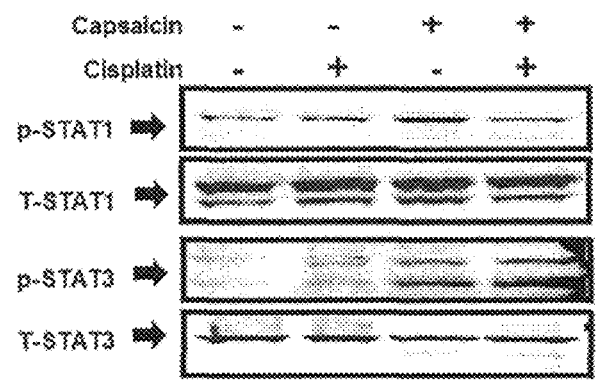
Figure 5F:
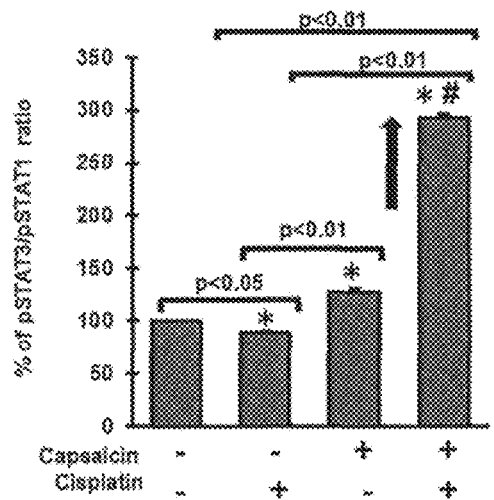
Figure 5G:
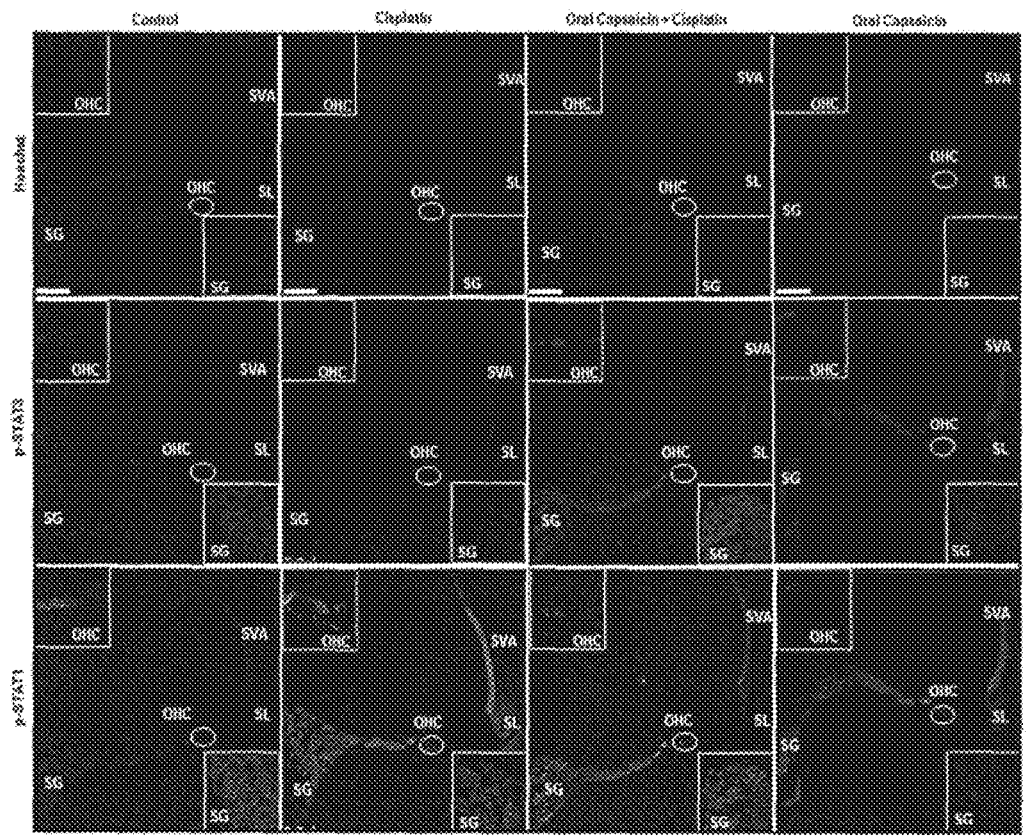
Figure 5H:
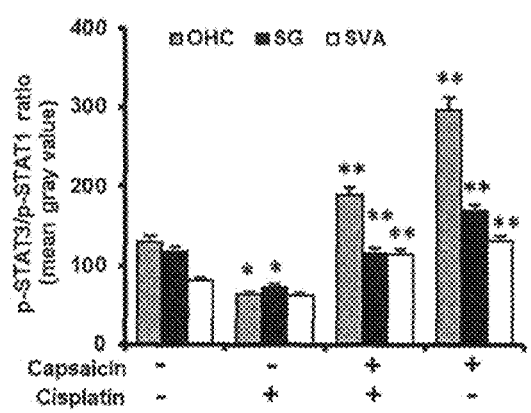
Figure 5I:
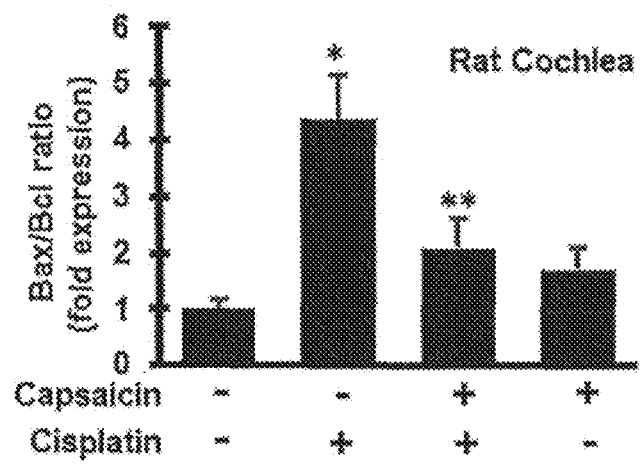
Figure 6A:
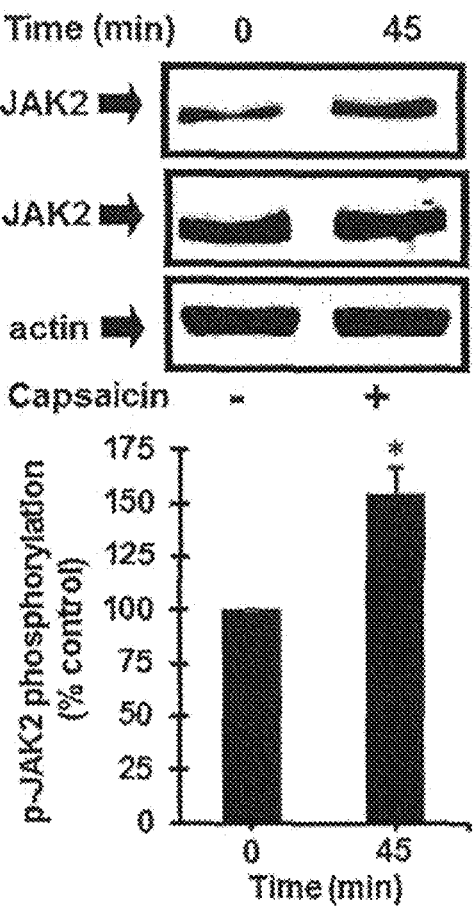
FIG. 6.A.

It was reported that EGCG (epigallocatechin gallate) protects against cisplatin-induced apoptotic cell death by stabilizing the STAT3/STAT1 ratio [Borse et al.]. In the present study, capsaicin-regulated STAT1 and STAT3 activation is monitored. The latter promotes anti-inflammatory responses and cell survival [Tornabene et al.; Borse et al.]. Capsaicin (2.5 µM) is shown here to actiate STAT1 $Ser^{727}$ phosphorylation in UB/OC-1 cells in a time-dependent fashion, which peaks at 45 min and returns to baseline by 120 min (FIG. 4A). Capsaicin induced $Tyr^{715}$ p-STAT3 phosphorylation was time-dependent, and peaks at 45 min after drug administration and returns to baseline by 120 min (FIG. 5A). This was associated with increased activation of p-JAK2, the immediate upstream regulator of STAT3 phosphorylation at 45 min (FIG. 6A). Capsaicin treatment showed significant increase in p-STAT3/p-STAT1 ratio over time with a peak value (~130%) reached in 45 min, with recovery to baseline by 60 min (FIG. 5C), thus tilting the balance of the cell fate towards pro-survival. The ratio of pSTAT3/pSTAT1 was relatively unchanged beyond that time period.

Figures 6B, 7:
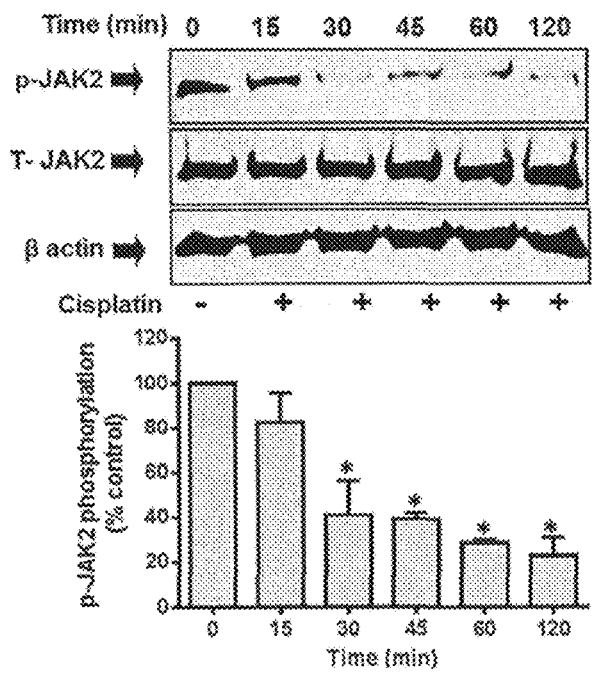
FIG. 7. Capsaicin pretreatment induces pro-survival p-STAT3/p-STAT1 signal as shown by fluorescent intensity analyses of the pro-survival signal in rat cochlea. Mid-modiolar sections of rat cochlea were probed with p-STAT3 and p-STAT1 antibodies and imaged using confocal microscopy. Fluorescent intensity analyses of the images were performed using Image J software. Mean gray values of p-STAT3 and p-STAT1 were calculated and the ratio for each sample in each group were then calculated as %. (p<0.05, *significant difference compared to oral PBS group, **significant difference compared to cisplatin treatment group).
Figure 8A:
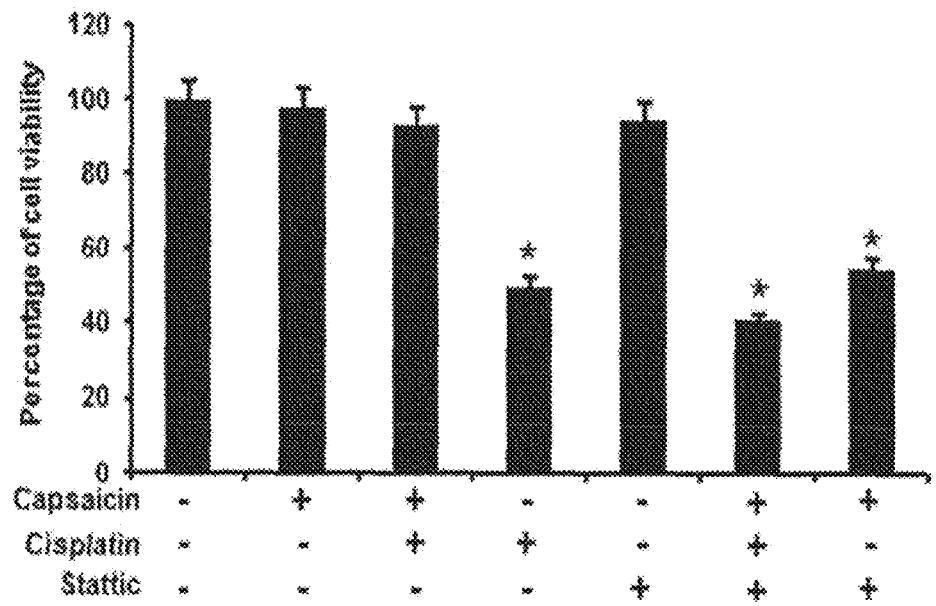
FIG. 8.A.
Figure 8B:
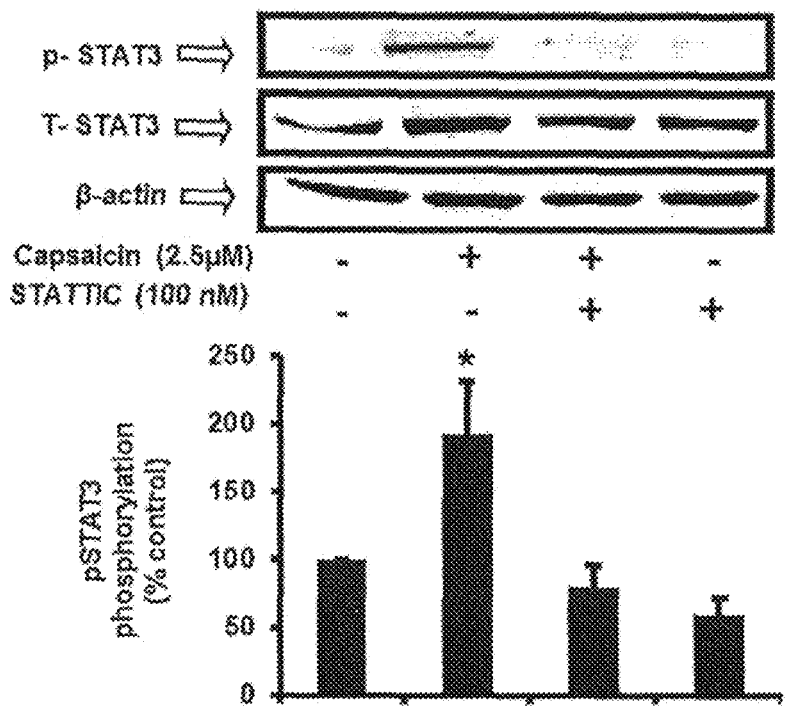
Figure 8C:
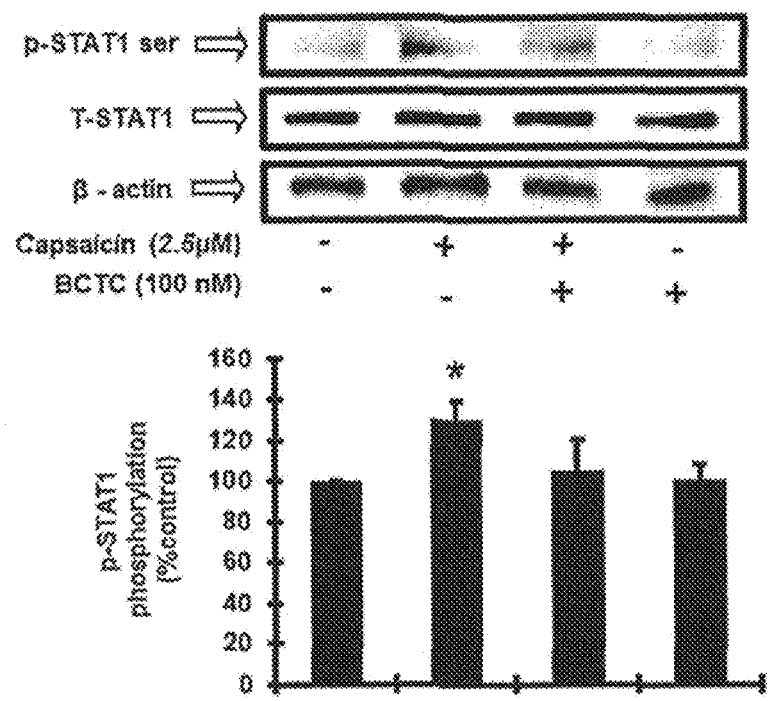
Figure 8D:
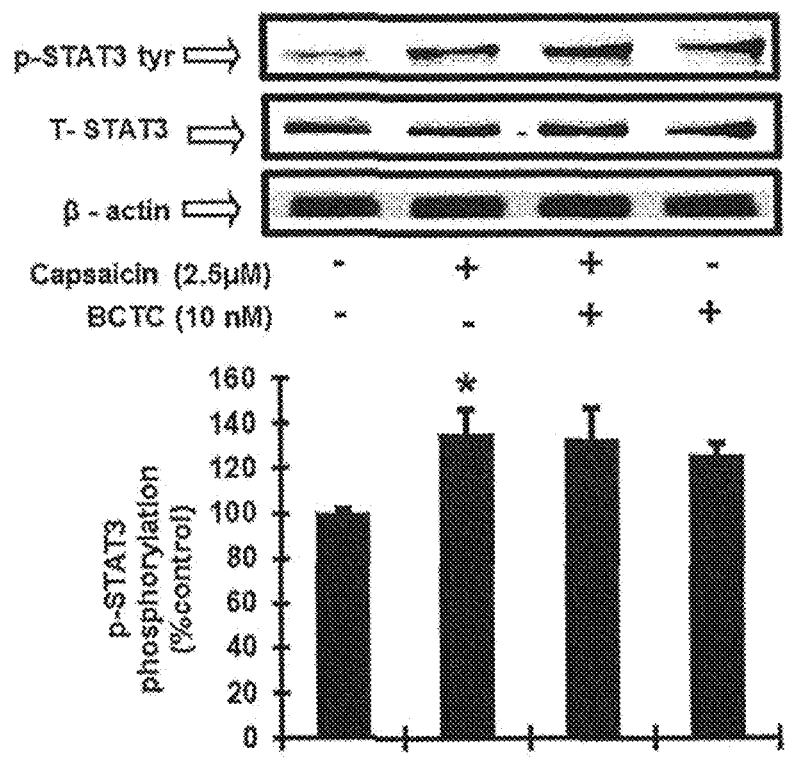
Figure 9A:
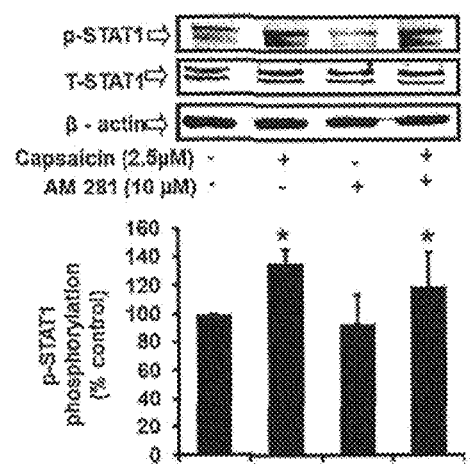
FIG. 9.A.
Figure 9B:
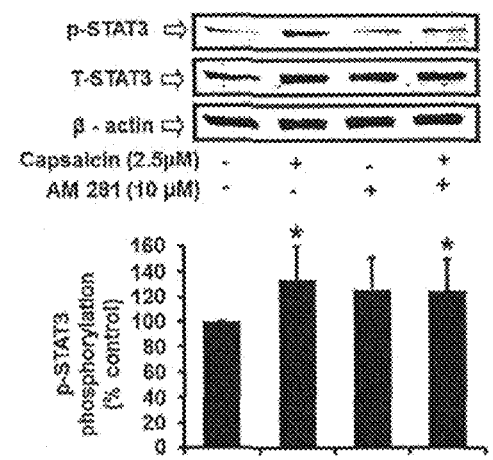
Figure 9C:
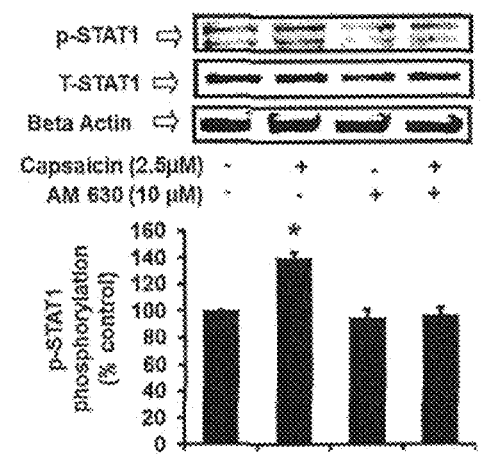
Figure 9D:
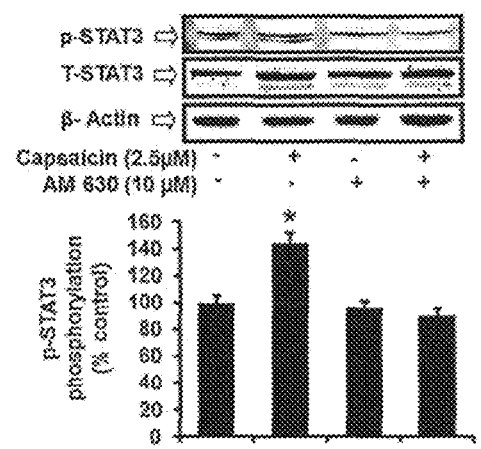
Figure 9E:
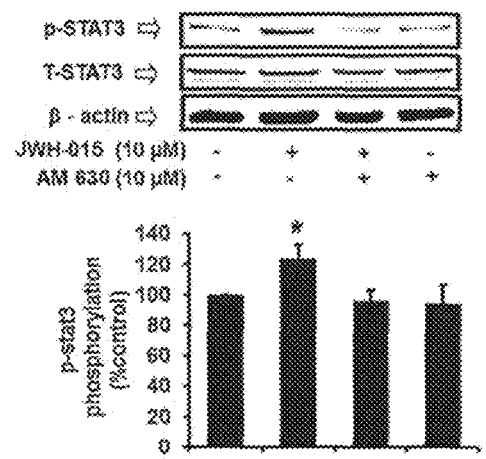
Figure 9F:
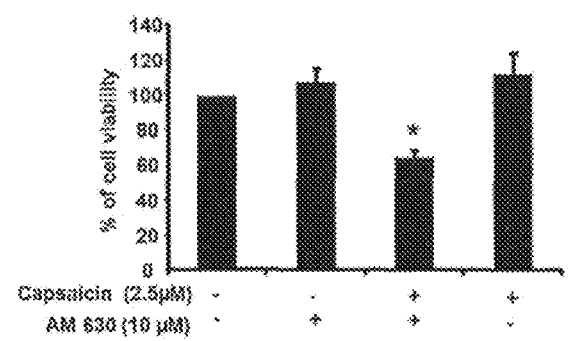
Figure 10A:
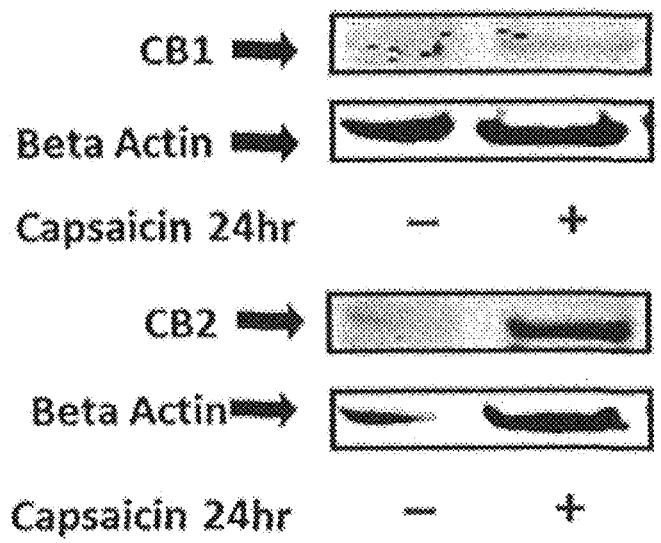
FIG. 10.A.
Figure 10B:
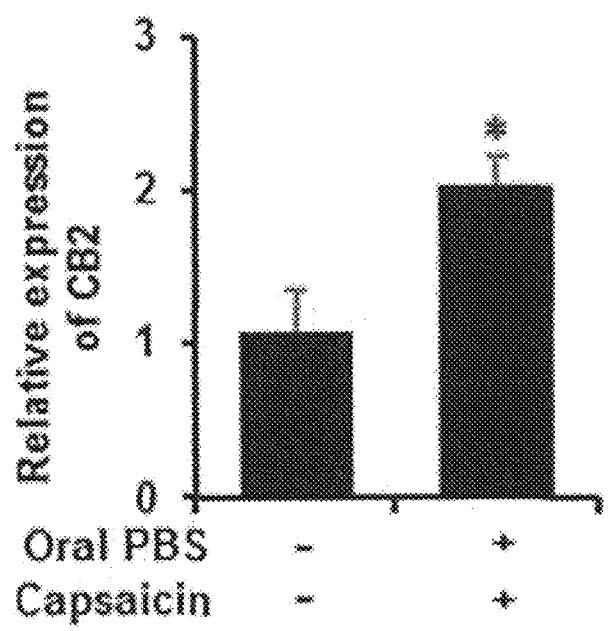
Figure 10C:
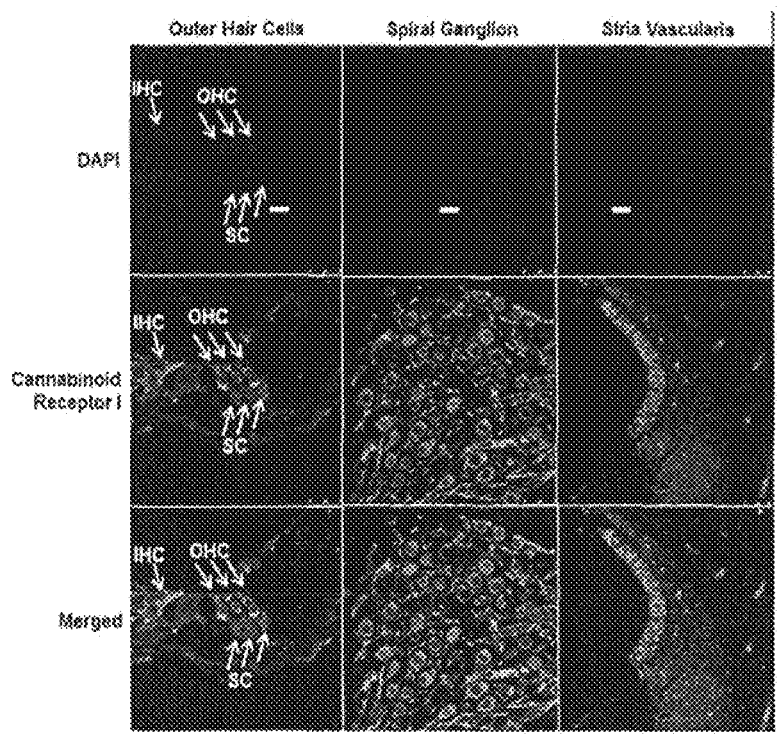
Figure 10D:
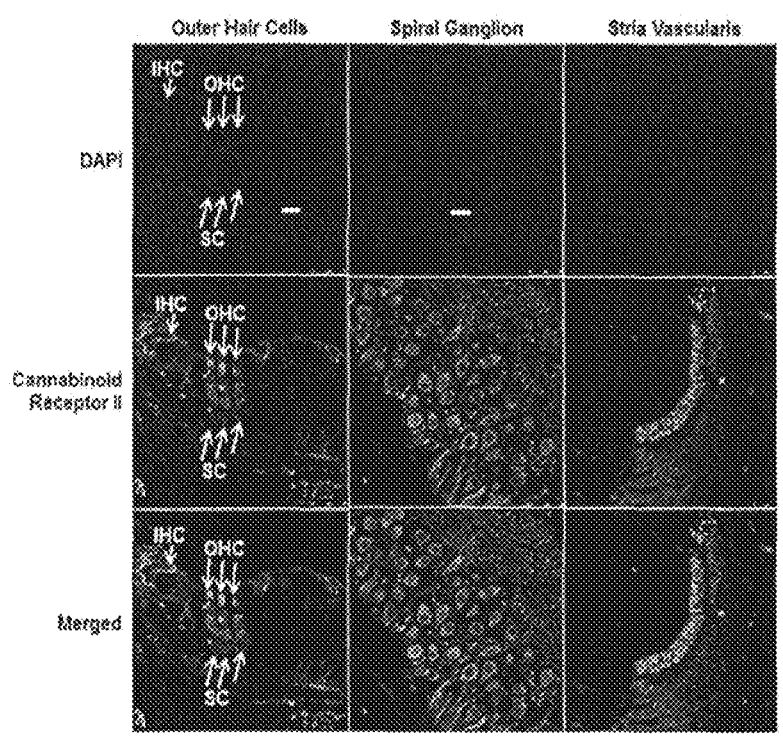

Cells treated with cisplatin (2.5 µM) showed a persistent increase in $Ser^{727}$ p-STAT1, which was still elevated at 120 min (FIG. 4B). Cisplatin was observed to produce a sustained inhibition of $Tyr^{707}$ p-STAT3 at 120 minutes (FIG. 5.B.). The ratio of p-STAT3/p-STAT1 following cisplatin treatment is shown in FIG. 5.D. This indicates a significant and persistent reduction in this ratio from 30 min to 120 min. Disruption of p-STAT3/STAT1 balance by inhibiting or knockdown of STAT3 sensitizes UB/OC-1 cells to cisplatin [Borse et al.]. Suppression of p-STAT3 phosphorylation was associated with persistent and significant reductions in JAK2 phosphorylation at 45 minutes up to 2 hours (FIG. 6.B.). This dichotomy in regulation of the p-STAT3/p-STAT1 ratio between capsaicin and cisplatin could stimulate different sets of genes, which in turn functions to provide cytoprotection in the cochlea by capsaicin. UB/OC1 cells pretreated with capsaicin (2.5 µM) for 30 minutes prior to cisplatin treatment for 45 minutes showed significantly decreased p-STAT1 (63.9±3%) with a concurrent increase in p-STAT3 (186.2±6.6%) activation. Cisplatin treatment increases p-STAT1 (120±2%) significantly, with little or no significant change in p-STAT3 phosphorylation (106.5±2.5%), while capsaicin treatment increased p-STAT1 (135.4±4%) and p-STAT3 (173±4%) significantly (FIG. 5.E.). The p-STAT3/p-STAT1 ratio of the cisplatin treatment alone (88.74±3.8%) was significantly decreased from control. Capsaicin treatment alone increased the ratio significantly (128±4.1%) compared to control as well as cisplatin, while capsaicin+cisplatin treatment increased the p-STAT3/p-STAT1 ratio to (292.8±5%) of control (FIG. 5.F.), confirming our hypothesis that capsaicin protects from cisplatin-induced stress response by altering the p-STAT3/p-STAT1 ratio to cell survival.

Immunohistochemistry studies using mid-modiolar cochlear sections from rats treated with cisplatin for 72 h showed up-regulation of $Ser^{727}$ p-STAT1 in the basal turn. Similar mid-modiolar sections from oral capsaicin-treated rats did not show up-regulation in $Ser^{727}$ p-STAT1 (FIG. 5.G.), indicating inherent differences between these two drugs. Interestingly, oral capsaicin increased $Tyr^{705}$ p-STAT3 phosphorylation as shown in mid-modiolar cochlear sections at 72 h post drug administration, while cisplatin suppressed STAT3 phosphorylation. Mean intensity analyses of the images with image J software indicate that the p-STAT3/p-STAT1 ratio is decreased significantly by cisplatin treatment in the OHC and SG, while SVA showed decreased ratio compared to oral PBS control sections. Oral capsaicin pretreatment significantly increased this ratio compared to cisplatin treatment, while oral capsaicin alone increased the p-STAT3/p-STAT1 ratio in all the three regions of the organ of *Corti* significantly, compared to control as well as cisplatin (FIG. 5.H.). The intensity ratios of p-STAT3/p-STAT1 in the different regions of organ of *Corti* are presented in FIG. 7. Capsaicin thereof are demonstrated to protect from cisplatin-induced hearing loss by inhibiting the pro-inflammatory pathway and, by stabilizing the p-STAT3/p-STAT1 ratio, thus, tilting the delicate balance towards cell survival.

Two genes, Bax and Bcl-2, were then monitored whose expressions are regulated by STAT1 [Benco et al.; Stephanou et al.] and STAT3 [Alas et al.; Jeong et al.], respectively. In UB/OC1 cells, Bax/Bcl-2 ratios were 1±0.2 for control, 2.9±0.1 for cisplatin, 1.31±0.1 capsaicin+cisplatin, and 1.1±0.2 for capsaicin-treated cells, respectively (graph not shown). Rat cochlear gene expression studies showed similar expression patterns of Bax/Bcl-2 ratio. In rats treated with oral PBS, the ratio was 1±0.2. Rats treated with cisplatin demonstrated a significant increase in the Bax/Bcl-2 ratio. Rats pre-treated with oral capsaicin prior to cisplatin demonstrated a significant decrease of this ratio. Rats treated with oral capsaicin alone showed a ratio less than half of that observed following cisplatin alone (FIG. 5.I.).

Capsaicin Mediated Protection is Dependent on STAT3 Activation.

The role of the STAT3 pathway in UB/OC-1 cell growth and survival is examined in the present study. Capsaicin, added prior to cisplatin, blocked cisplatin-induced cell killing of UB/OC-1 cells. Pre-treatment of UB/OC1 cells with STATTIC (a small molecule inhibitor of STAT3) abrogated the protective action of capsaicin against cisplatin-induced cell killing. Surprisingly, STATTIC also unmasked a toxic action of capsaicin (FIG. 8.A.). STATTIC (100 nM) significantly reduced the $Tyr^{705}$ p-STAT3 levels (FIG. 8.B.). An active role of STAT3 in cytoprotection is then demonstrated in cells challenged with a cytotoxic agent, such as cisplatin. The cytotoxic effect of capsaicin produced by STAT3 inhibition (FIG. 8.A.) implicates this transcription factor in the cell survival/proliferative actions of capsaicin. The lack of effect of STATTIC when added alone demonstrates that STAT3 pathway is not tonically active under normal resting conditions (FIG. 8.B.).

The importance of STAT3 activation in capsaicin-induced protection of UB/OC-1 cells is mediated by TRPV1. Blockade of the TRPV1 channel by a selective TRPV1 antagonist BCTC (N-(4-tertiarybutylphenyl)-4-(3-chloropyridin-2-yl) tetrahydropyrazine-1(2H)-carbox-amide, Tocris, Minneapolis, MN) was tested, this agent is known to have the ability to block the activation of TRPV1 by capsaicin [Pomonis et al.; Valenzano et al.]. Data shown in FIG. 8.C. indicate that the use of BCTC (100 nM) decreases the TRPV1 mediated STAT1-$Ser^{727}$ phosphorylation without significantly altering $Tyr^{715}$ STAT3 phosphorylation (FIG. 8.D.). These data demonstrates that capsaicin activates STAT1 through a TRPV1-dependent pathway and causes STAT3 phosphorylation independently.

Capsaicin Mediated pSTAT3 Activation is Cannabinoid Receptor CB2 Dependent.

Other potential targets of capsaicin were examined to explore whether capsaicin stimulates STAT3 phosphorylation independent of TRPV1. Some endocannabinoids can interact with TRPV1 [Di Marzo et al.; Zygmunt et al.]. Capsaicin, a TRPV1 agonist, was examined to determine if it could interact with cannabinoid receptors. UB/OC1 cells were treated with either CB1 antagonist AM281 (10 μM) or a CB2 antagonist, AM630 (10 μM) for 30 min prior to capsaicin (2.5 μM). Capsaicin significantly increased p-STAT1 $Ser^{727}$, while AM281 had no effect (FIG. 9.A.). Likewise, AM281 did not alter capsaicin induced p-STAT3 $Tyr^{715}$ phosphorylation (FIG. 9.B.). However, inhibition of CB2 receptors with AM630 significantly decreased capsaicin-induced $Tyr^{705}$ p-STAT3 and $Ser^{727}$ p-STAT1. Western blots showed that AM630 pretreatment decreased capsaicin-induced $Ser^{727}$ p-STAT1 phosphorylation (FIG. 9.C.) and also decreased $Tyr^{705}$ p-STAT3 phosphorylation (FIG. 9.D.). Moreover, the CB2 receptor agonist JWH015 increased p-STAT3 and this effect was reversed by AM630 (FIG. 9.E.). Pre-treatment of UB/OC-1 cells with AM630 30 minutes prior to capsaicin for 24 h significantly decreased cell viability compared to capsaicin (FIG. 9.F.). Thus, capsaicin is demonstrated to activate STAT3 via CB2 receptors. These effects may enhance cell survival.

Example 6. Cannabinoid Receptors are Expressed in the Rat Cochlea, and CB2 Receptor is Essential for Capsaicin-Induced, Protection of Cisplatin-Mediated Hearing Loss CB2 receptors have been reported to be expressed in HEI/OC1 cells [Jeong et al.] and in the albino rat cochlea [Martin-Saldana et al.]. CB1 expression has also been reported in SAMP8 mice *cochleae* [Hwang et al.]. Cannabinoid receptors (CB1 and CB2) were examined to determine if they are expressed in UB/OC1 cells and in the rat cochlea. Capsaicin treatment could increase the expression of CB receptors. Western blotting was performed on UB/OC1 cells treated with capsaicin for 24 h. Capsaicin increased CB2 expression in UB/OC1 cells (FIG. 10.A.). Rat cochlear gene expression levels were determined 72 h d after oral capsaicin treatment. Capsaicin increased the expression of CB2 receptor in the rat cochlea fold relative to basal expression (FIG. 10.B.). CB1 and CB2 receptor expression was observed by immunofluorescent labeling in the organ of *Corti* in the OHCs, IHC's, the supporting cells (SC's), the spiral ganglion and the stria vascularis in mid-modiolar sections of untreated rats (FIGS. 10.C. and 10.D.).

Figure 11A:
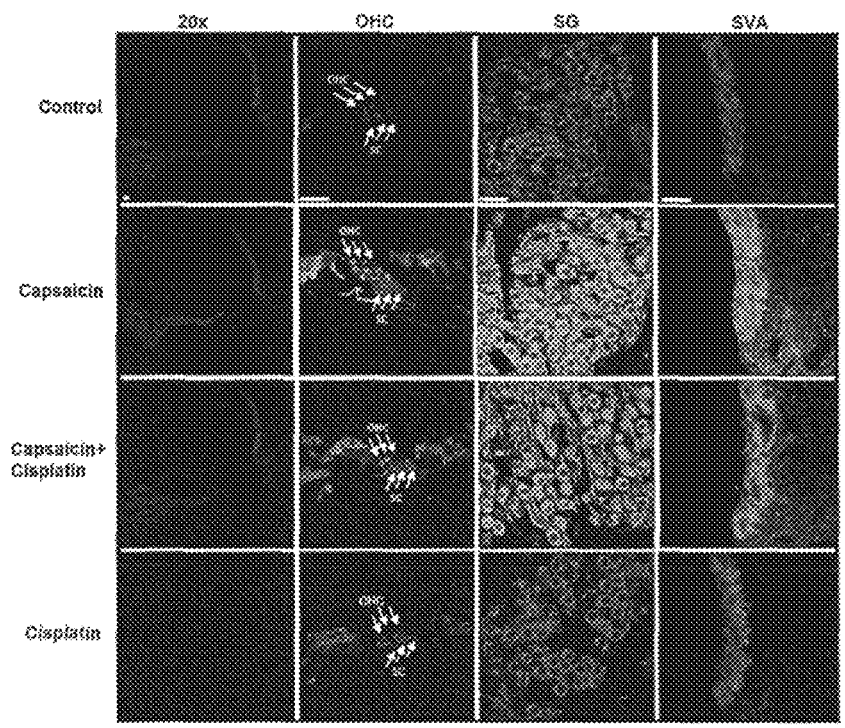
FIG. 11.A.
Figure 11B:
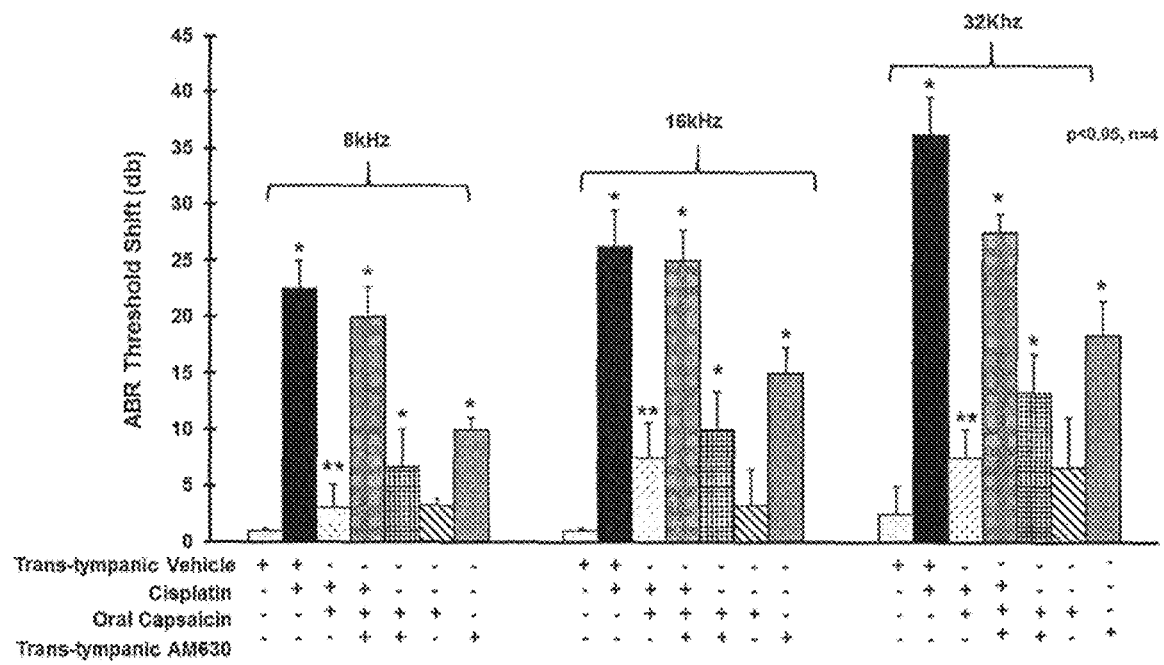
Figure 12A:
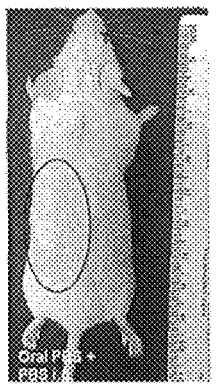
FIG. 12.A.
Figure 12C:
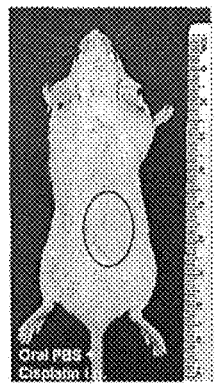
Figure 12E:
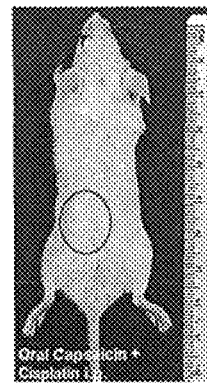
Figure 12G:
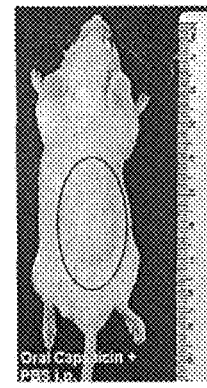
Figure 12B:
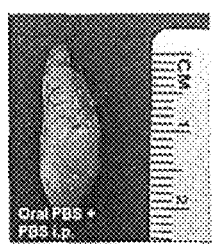
Figure 12D:
Figure 12F:
Figure 12H:
Figure 12I:
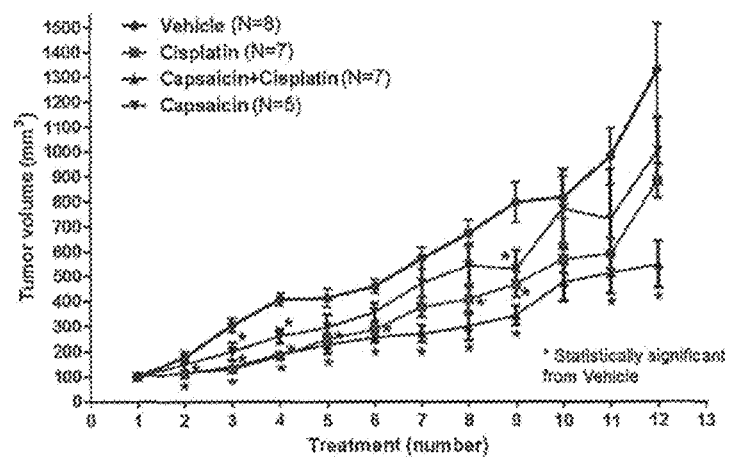
Figure 12J:
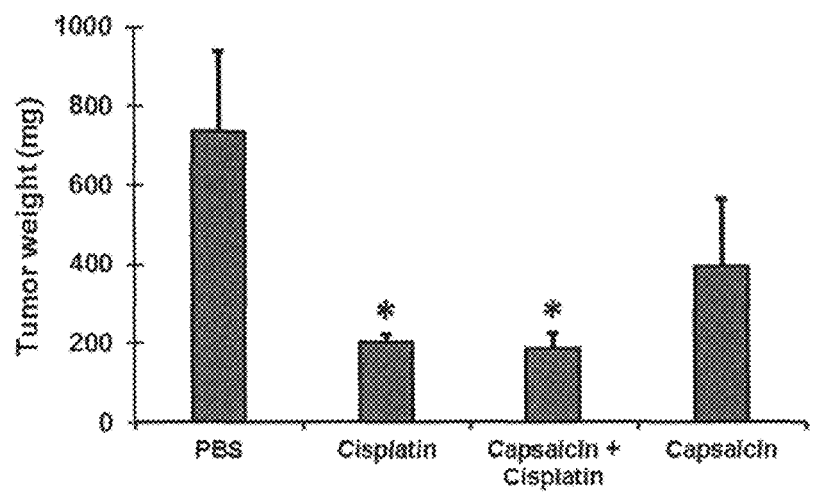

Capsaicin induced CB2 receptor activation was examined. Rats were pretreated with either vehicle or AM630 by the trans-tympanic route, followed by oral capsaicin (20 mg/kg) or vehicle 4 h later. Cisplatin (11 mg/kg, i.p.) was administered 24 h after oral capsaicin and recorded ABR thresholds 72 h later. Relative fluorescent intensity (rfi) analyses of mid-modiolar section using confocal microscopy by ImageJ software indicated that cisplatin treatment did not significantly change the level of CB2 labelling in the OHCs, SGs or in the SVA. However, capsaicin pretreatment significantly increased the expression of CB2 in all the three regions of the *cochleae*, while capsaicin treatment alone increased CB2 labelling in all the three regions to an even greater extent compared to control (FIG. 11.A.). Cisplatin produced a 20-40 dB ABR threshold shift with increasing frequencies ranging, from 8-32 kHz, which was abrogated by oral capsaicin. Trans-tympanic administration of CB2 receptor antagonist AM630 reversed the protective effect of oral capsaicin against cisplatin-induced hearing loss. Interestingly, AM630 added either alone or in combination with capsaicin resulted in significant increases in ABR thresholds (FIG. 11.B.). CB2 exerts is therefore demonstrated to provide a tonic protective function in the cochlea, thus providing a novel target for otoprotection.

Example 7. Capsaicin does not Interfere with the Antitumor Efficacy of Cisplatin and Augments Inhibition of Tumor Growth In Vivo A SCID mouse xenograft model was employed to determine the effect of oral capsaicin treatment chemotherapeutic efficacy of cisplatin. Mice were injected with $1 \times 10^6$ head and neck squamous cell carcinoma (UMSCC-10b) cells subcutaneously in the flank region. Tumor growth plotted over a four week period showed a substantial increase in tumor volumes over time which was significantly reduced by cisplatin. Administration of oral capsaicin shifted the cisplatin tumor growth curves to the right, suggesting improved efficacy of this drug combination over cisplatin alone. Tumor weights obtained at the end of the treatment period support these findings (FIG. 12).

Figure 13:
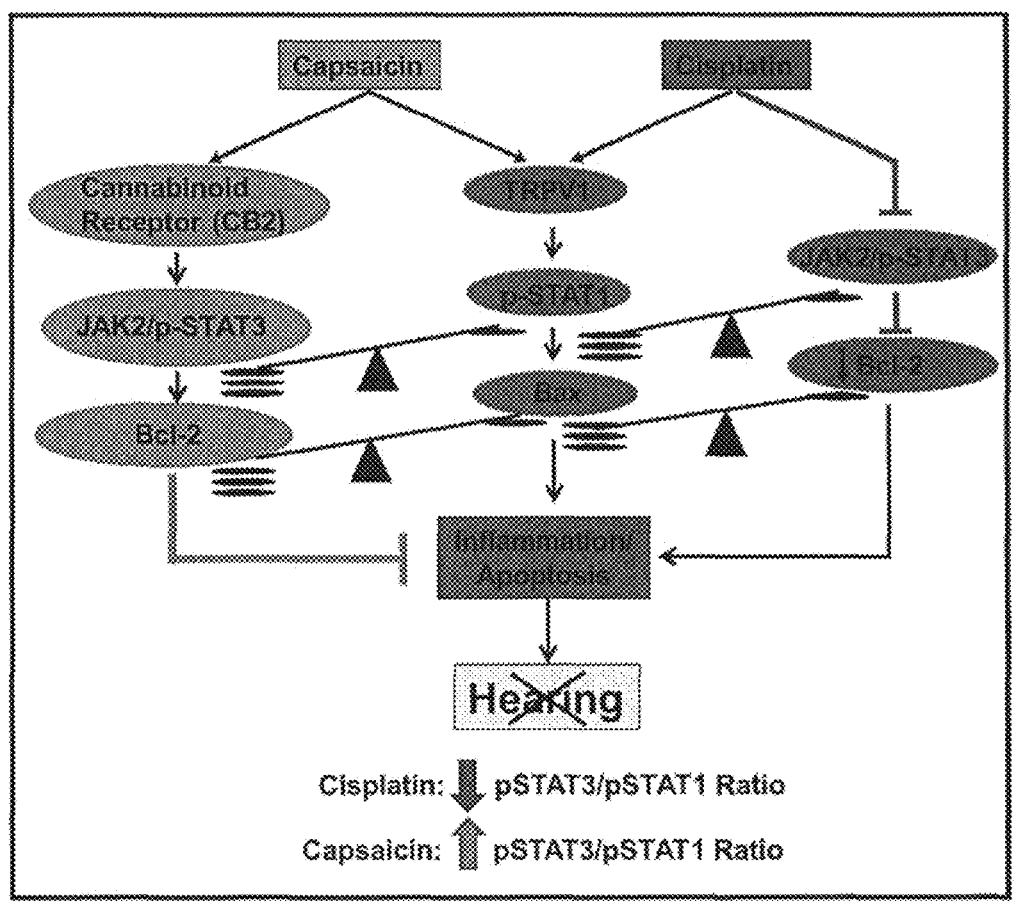
FIG. 13. A summary of capsaicin protection against cisplatin ototoxicity. This chart summarizes the proposed molecular mechanisms underlying capsaicin mediated protection against cisplatin-induced ototoxicity. Otoprotection mediated by capsaicin is produced, at least in part, by activation of CB receptors which further activates STAT3. Activation of STAT1 by capsaicin contributes to the transient inflammatory response without recruitment of apoptotic pathways as previously observed in vivo (as shown by the green dotted arrow). The transient inflammation through the activation of STAT1 desensitizes the TRPV1 receptors, decreasing the presence of STAT1 to be activated by cisplatin. Such phenomenon can mitigate the undesired inflammation further initiated by cisplatin. The net protective action of capsaicin could result from an increase in the JAK2 and STAT3/STAT1 ratio in cells in the cochlea, abrogating the negative impact of cisplatin on this ratio.
Figure 15A:
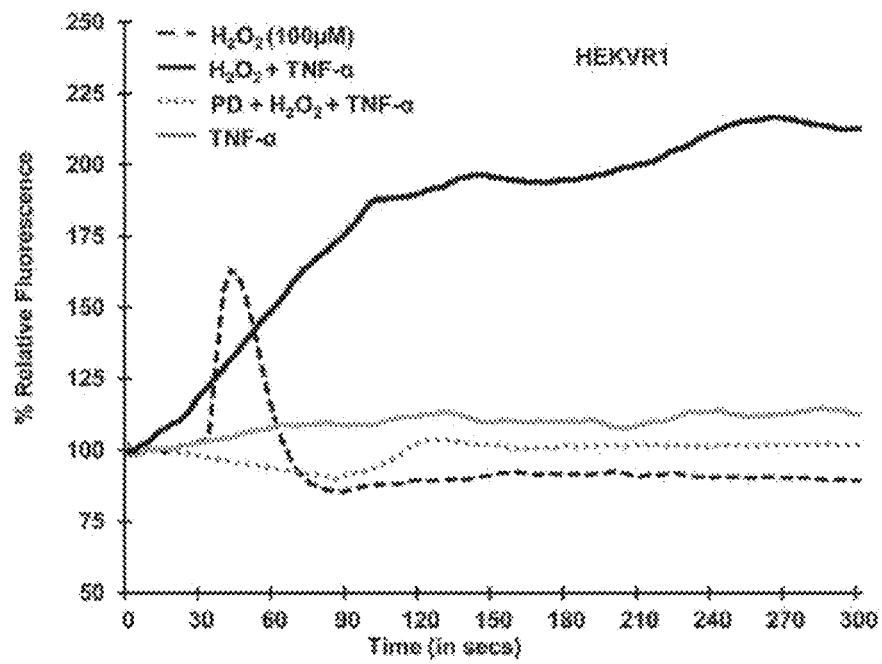
FIG. 15.A.
Figure 15B:
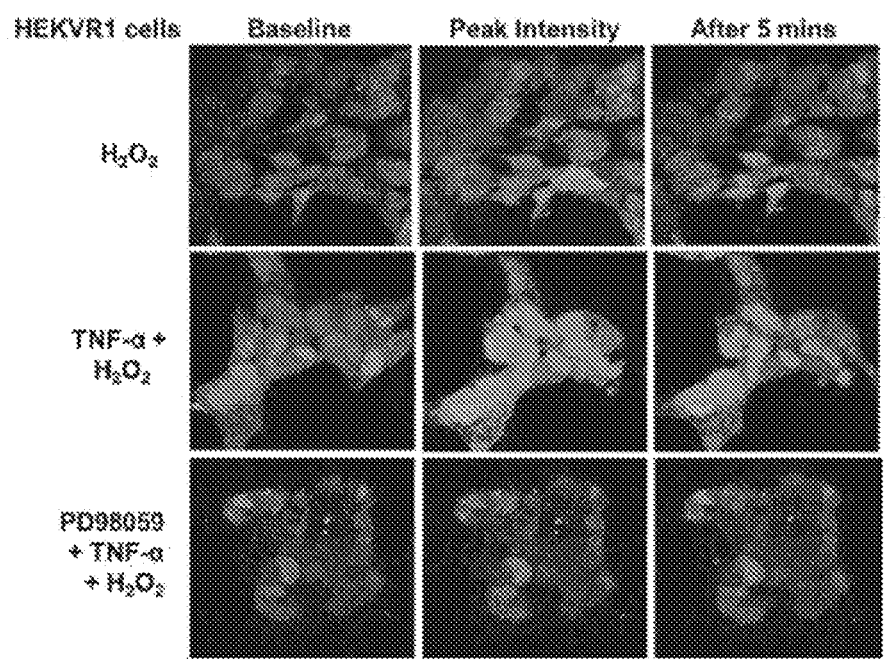
Figure 15C:
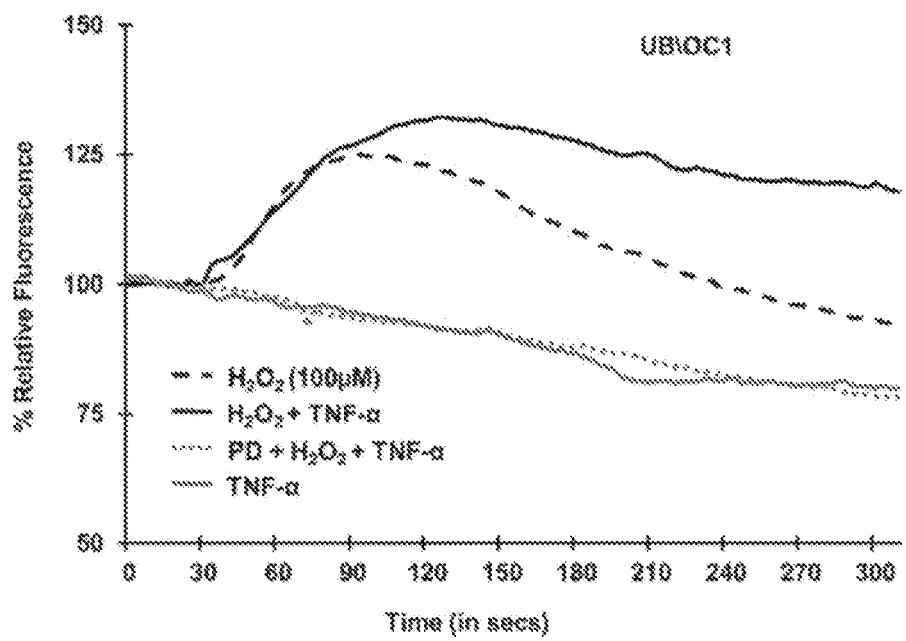
Figure 15D:
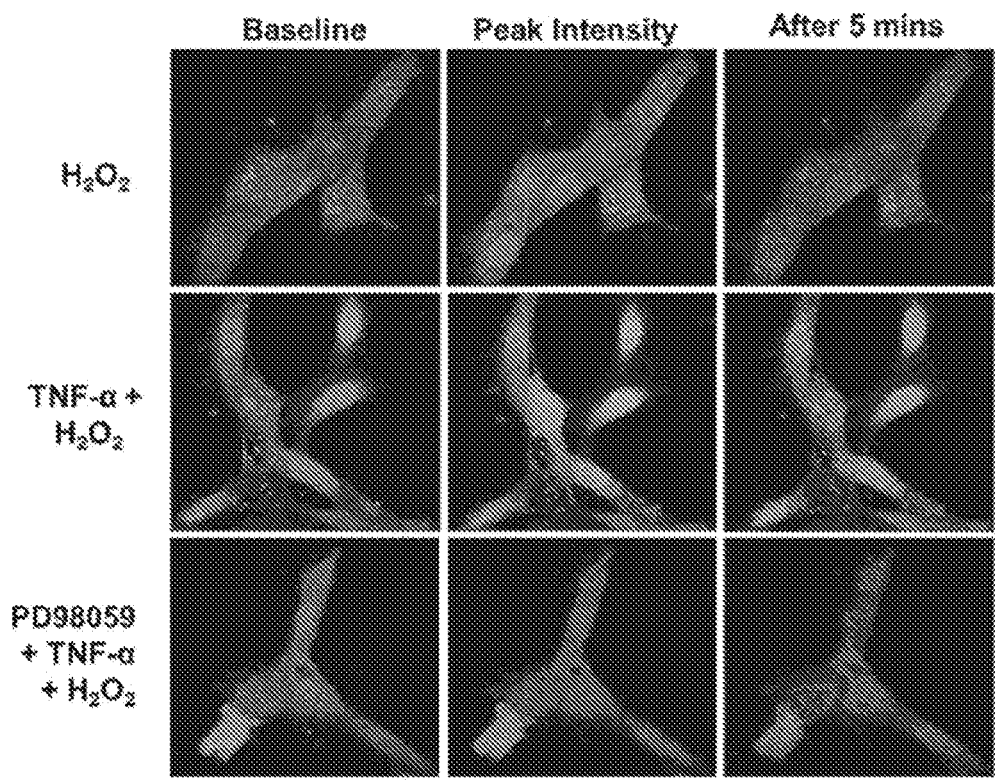
Figure 15E:
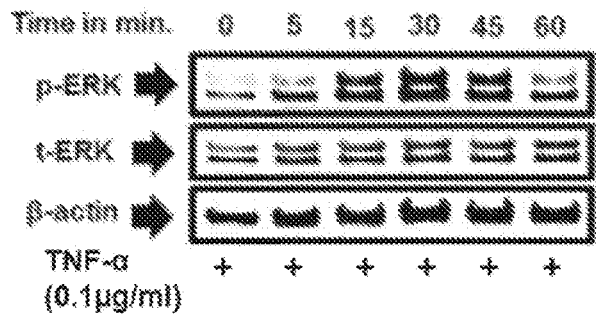
Figure 15F:
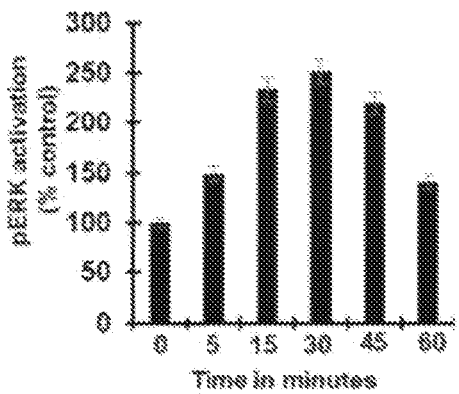
Figure 15G:
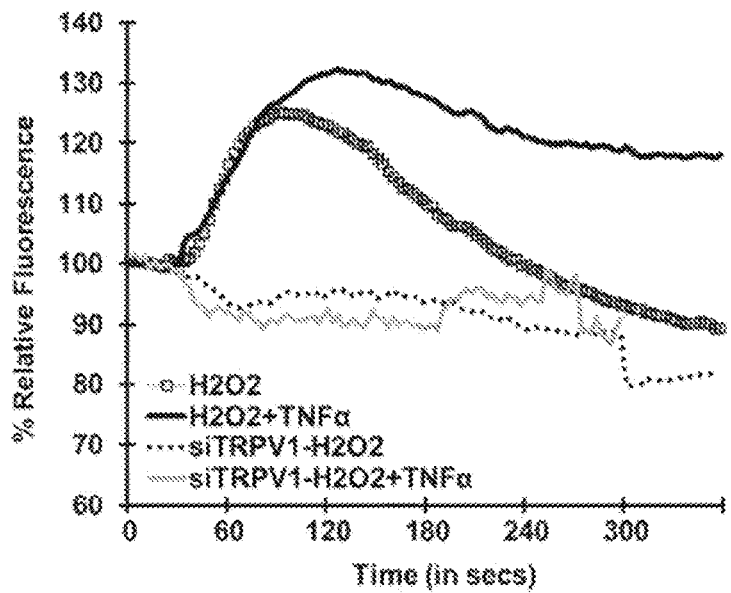
Figure 15H:
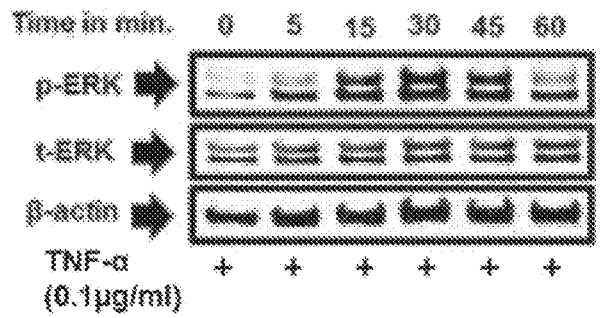
Figure 15I:
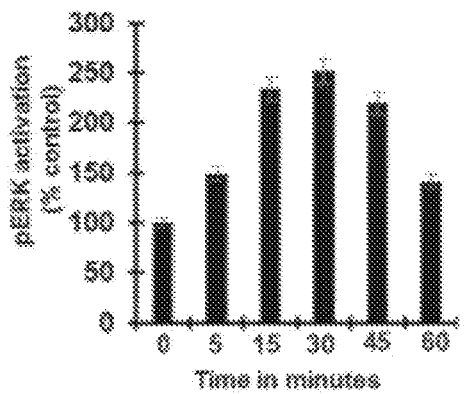
Figure 15J:
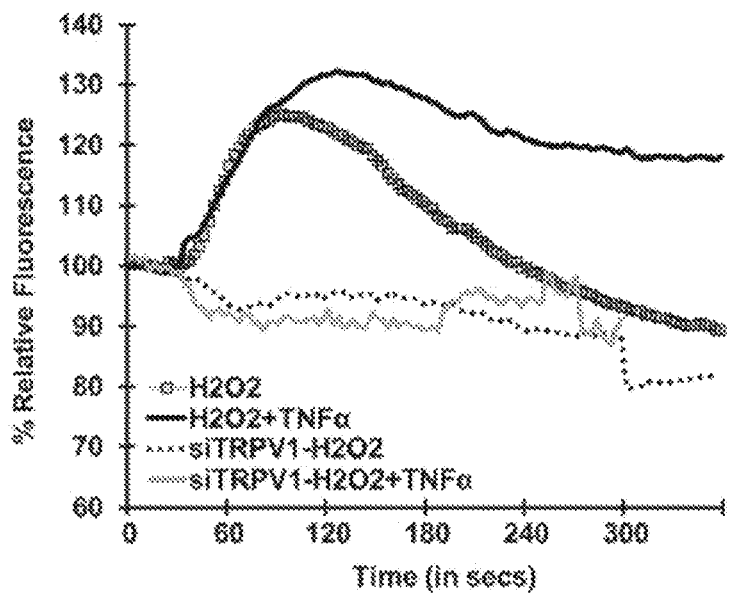
Figure 15K:
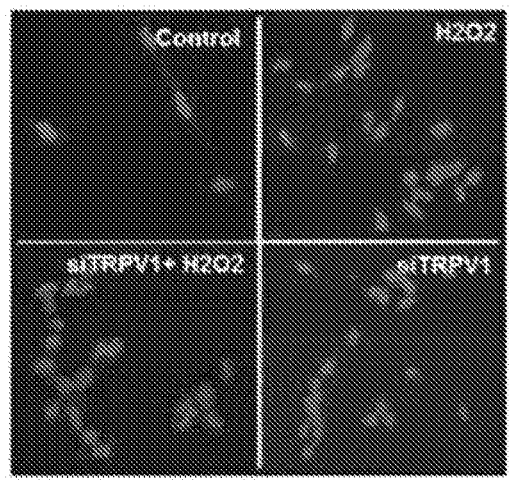
Figure 15L:
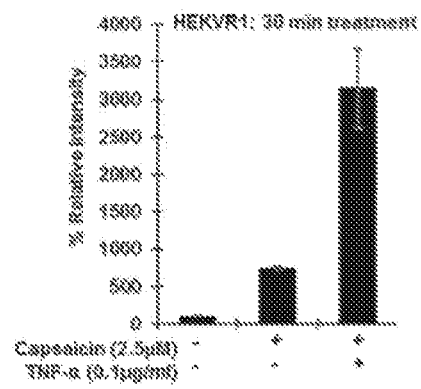
Figure 15M:
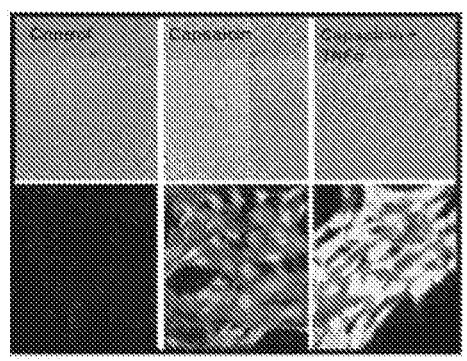

Capsaicin protects against ototoxic agent (e.g., cisplatin)-induced ototoxicity. Capsaicin produces transient hearing loss in the rat which recovered over a three day period, unlike cisplatin which produced persistent hearing loss [Mukherjea et al., 2011]. The transient nature of capsaicin's action preconditions the cochlea to a subsequent cochlear trauma (i.e. to an ototoxic drug) (FIG. 13). This study confirms that capsaicin preconditions the cochlea and reduces cisplatin ototoxicity. Capsaicin, unlike cisplatin, produces transient activation of STAT1 in UB/OC-1 cells and in the cochlea. These findings contrast with the more persistent activation of STAT1 by cisplatin in both UB/OC-1 cells and cochlea and likely result from the more persistent activation of TRPV1 by cisplatin.

Preconditioning sound in rat and mouse models have been reported to protect from noise injury as well as age-induced hearing loss [Canlon et al; Tanaka et al.; Yoshida et al.]. Sound preconditioning may work via the induction of heat shock proteins (HSPs) [Roy et al.]. A study in zebrafish reports that dexmedetomidine (DEX) (an alpha-2 adrenoreceptor selective agonist) is effective in preconditioning against cisplatin ototoxicity [Min et al.].

The differences in the ABR threshold shifts in the capsaicin and cisplatin-treated rats were unexpected, given that both capsaicin and cisplatin target TRPV1 [Mukherjea et al., 2008]. Data here shows the involvement of TRPV1 in both capsaicin and cisplatin mediated inflammatory response leading to either a temporary or a permanent ABR threshold shift respectively. Capsaicin mediated TRPV1 activation is transient and resolved within 72 h. The data here further indicates that capsaicin causes an induction of pro-apoptotic STAT1 transcription factor as well as the pro-survival STAT3 transcription factor. This induction of p-STAT3 in the cochlea persists even at 72 h after capsaicin. However, capsaicin transiently induced p-STAT1. This tilts the balance of the p-STAT3/p-STAT1 ratio towards cell survival. Activation of TRPV1 by capsaicin promotes STAT1 activation and the transient induction of inflammatory genes in the cochlea, leading to temporary hearing loss for 24 hr [Mukherjea et al., 2011]. Similarly, activation of TRPV1 in small diameter C-fiber neurons promotes neurogenic inflammation [Caterina et al.; Holzer 1988]. However, following cisplatin treatment, STAT1 activation persists for 72 h while STAT3 activation is decreased. This alters the balance of p-STAT3/p-STAT1 towards cell death. Cisplatin treatment results in sustained increase in cochlear ROS generation. This leads to TRPV1 activation and persistent inflammation [Mukherjea et al., 2008]. Thus, TRPV1 appears to be a target for the induction of hearing loss by cisplatin. Knockdown of this protein provided significant protection against cisplatin-induced hearing loss, and apoptosis of outer hair cells [Mukherjea et al., 2008]. However, TRPV1 agonists appear to be effective in treating bladder pain and over reactive bladder, presumably by inducing desensitization of this receptor [Bley et al.]. These data suggest a bimodal function of TRPV1 activation by capsaicin but not cisplatin in the cochlea.

The mechanism underlying the transient activation of STAT1 by capsaicin is unclear but may involve rapid dephosphorylation of this protein by phospho-serine phosphatases, such as protein phosphatase 2A and calcineurin. In addition, it is possible that the increased STAT3 activation produced by capsaicin negatively influences STAT1 activation [Shen et al.; Qing et al.]. Another difference between capsaicin and cisplatin is their differing ability to regulate JAK2 and STAT3 phosphorylation. In the present cell culture model, rapid phosphorylation was shown of both JAK2 and STAT3 by capsaicin, which persisted for at least 120 min. In contrast, cisplatin produced rapid inhibition of JAK2 and STAT3 phosphorylation. Therefore, the cellular STAT3/STAT1 ratio and cell viability is greater in the capsaicin-treated cells as compared to the cisplatin-treated cells.

Similar results were found in vivo. Capsaicin increased STAT3 activation without activating STAT1 at 3 days following exposure to cisplatin. In contrast, rats administered cisplatin demonstrated reduced p-STAT3 and greater p-STAT1 in the cochlea than vehicle-treated rats. In nerve injury, STAT3 appears to play a pro-survival role. This transcription factor appears to be crucial for Schwann cell survival and phenotype conversion for regeneration in mice [Benito et al.]. STAT3 also inhibits interferon-mediated STAT1 activity and its ability to form homodimers in myeloid cells [Ho et al.]. Therefore, an increase in STAT3 by capsaicin could serve to diminish the activity of STAT1 and prevent inflammation produced by cisplatin. In contrast, inhibition of STAT3 by STATTIC enhanced killing of UB/OC-1 cells by cisplatin in vitro, without affecting survival under basal conditions. Furthermore, STATTIC unmasked a cytotoxic property of capsaicin, likely resulting from unopposed activation of STAT1. STAT3 has important cellular functions linked to cell survival [Levy et al.] and the relative proportions of STAT1/STAT3 can regulate the transcriptional activity of anti-apoptotic genes such as Bcl-2 and Bcl-x [Stephanou et al.]. Thus, inhibition of STAT3 by cisplatin could play a major role in its initiation of cell death in the cochlea.

Another important finding of this study is that capsaicin-dependent activation of STAT3 is mediated, at least in part, through CB2 receptors. Immunohistochemical studies show expression of CB2 in the cochlea, localized primarily in the OHCs, IHCs, stria vascularis and spiral ganglion cells. Activation of these receptors appears to protect against cisplatin ototoxicity. Inhibition of these receptors by a CB2-selective antagonist reversed this protective action of capsaicin and produced significant hearing loss when added alone. Thus, CB2 receptor activation by endogenous cannabinoids could have a tonic influence on hearing.

The otoprotective function of capsaicin did not appear to compromise cisplatin-induced reduction of tumor growth in a SCID mouse xenograft model. In fact, there appeared to be a trend towards increased chemotherapeutic efficacy of combined capsaicin and cisplatin drug compared to cisplatin alone. Therefore, combining oral capsaicin with cisplatin-based chemotherapy could protect against hearing loss without compromising the chemotherapeutic efficacy of cisplatin. The ease of administering capsaicin orally could enhance the feasibility of this approach. Capsaicin is available commercially as a flavored capsule that is easily tolerated. In addition, capsaicin is already in use clinically as a topical ointment for pain and skin conditions, and *cannabis* derived medicines are also in clinical use for the treatment of various inflammatory diseases.

Without being bound to any particular theory, a mechanism for the protective effect of capsaicin against cisplatin ototoxicity may exist in that capsaicin mediates a transient early inflammatory response in the cochlea. It also activates a delayed anti-inflammatory, pro-survival cascade that protects against cisplatin-induced hearing loss. Capsaicin appears to be otoprotective by desensitization of TRPV1 and also by activation of CB2 receptors. CB2 receptor activation leads to JAK2/STAT3 pro-survival signaling that negates the cisplatin-induced inflammatory/apoptotic (STAT1/Bax: Bcl2) pathways. Capsaicin also activates the TRPV1 pathway transiently which causes an increase in $Ca^{2+}$ release, an increase in ROS generation and increased p-STAT1Ser$^{727}$ phosphorylation. However, apoptotic pathways are not recruited since p53 is not activated [Hughes et al.]. Cisplatin activates TRPV1 receptors chronically. This leads to increases in $Ca^{2+}$, ROS and p-STAT1Ser$^{727}$ phosphorylation and inflammation. This is followed by recruitment of p53, BAX and caspase cascade [Kaur et al.]. Thus capsaicin shifts the delicate balance of STAT3/STAT1 [Shen et al.] towards pro-survival signaling, enabling a CB2R activation leading to cell survival. This inhibits damage and apoptosis of outer hair cells and prevents hearing loss in cisplatin treated animals (FIG. 13).

Example 8. Etanercept and Capsaicin Ameliorates and Provides A Treatment for Noise Induced Hearing Loss The present example demonstrates the utility of the present methods and compositions for ameliorating noise induced hearing loss in a subject in vivo with etanercept treatment and is enhanced with treatment with capsaicin at sub-optimal doses.

Materials and Methods

Animal Procedures and Sample Collection

Male Wistar rats (150-250 gm) were used for this study under an animal care protocol approved by the Laboratory and Animal Care and Use Committee (SIU School of Medicine). Pre-treatment ABRs were performed. Animals were then treated according to the experimental paradigm. Prevention strategy: consisted of administration of ETA either intra-tympanic ally (IT) (250 µg/50 µl) or subcutaneously (sc) (3 mg/kg) or PBS (IT-50 µl or sc-1 ml) either 3 days or 7 days prior to noise exposure (NE).

Treatment

Animals were exposed to noise (NE), and then provided ETA treatments either IT or SC at either 2 h or 24 h post noise injury. Post treatment ABR thresholds were determined at 21 days post noise exposure and *cochleae* were excised for morphological, molecular and biochemical studies. *Cochleae* used for RNA preparations were flushed immediately with RNA later and kept in RNA later for 24 h at 4° C. Those used for immunohistochemical studies were perfused and fixed with 4% paraformaldehyde, while those used for Scanning electron microscopy (SEM) were perfused and fixed with 2.5% glutaraldehyde. *Cochleae* used for whole mounts were decalcified for 7-10 days in 100 mM EDTA at room temperature.

Noise Exposure.

Male Wistar rats were exposed to octave band noise at 122 dB centered at 16 kHz for 1 h under isofluorane anesthesia, with the 3 inch silicon tubes attached to the high frequency transducer resting in the middle ear cavity. This exposure typically results in a 30-50 dB temporary threshold shift (measured as an immediate pre-to-post noise exposure shift in ABR thresholds) across all frequencies; with slightly more elevation at those frequencies around 16 kHz and 20-40 dB permanent threshold shift measured at 21 days post noise exposure at all frequencies. Acoustic stimuli are calibrated using a cloth model rat and a Bruel & Kjaer Pulse System with a ½ inch free-field microphone (B&K model 4191). Baseline noise levels in the test chamber (with background test noise turned off) are typically measured below 20 dB SPL in the 4-40 kHz range.

Intra-Tympanic Injections.

Male Wistar rats were exposed to octave band noise at 122 dB centered at 16 kHz for 1 h under isofluorane anesthesia, with the 3 inch silicon tubes attached to the high frequency transducer resting in the middle ear cavity. This exposure typically results in a 30-50 dB temporary threshold shift (measured as an immediate pre-to-post noise exposure shift in ABR thresholds) across all frequencies; with slightly more elevation at those frequencies around 16 kHz and 20-40 dB permanent threshold shift measured at 21 days post noise exposure at all frequencies. Acoustic stimuli are calibrated using a cloth model rat and a Bruel & Kjaer Pulse System with a ½ inch free-field microphone (B&K model 4191). Baseline noise levels in the test chamber (with background test noise turned off) are typically measured below 20 dB SPL in the 4-40 kHz range.

Auditory Brainstem Evoked Responses (ABRs).

Pre-treatment ABR thresholds were determined using the high frequency Intelligent Hearing Systems (IHS) on naive rats prior to any treatment or noise exposure for each ear. Animals were tested with a stimulus intensity series that was initiated at 0 dB sound pressure level (SPL) and reached a maximum at 90 dB SPL. The stimulus intensity levels were increased in 10 dB increments, and the evoked ABR waveforms were observed on a video monitor. The auditory stimuli included tone bursts at 8, 16, and 32 kHz with a 10 msec plateau and a 1 msec rise/fall time presented at a rate of 5/sec. Threshold was defined as the lowest intensity capable of evoking a reproducible, visually detectable response with two distinct waveforms and minimum amplitude of 0.5 µV.

Scanning Electron Microscopy.

*Cochleae* were dissected out, perfused with 2.5% glutaraldehyde and processed for SEM as described previously. The relative effects of different treatments were assessed by comparing the percentage of hair cells present, as previously published by our group [Mukherjea et al., 2010].

Hair Cell Count.

Hair cell counts were performed using a modified version of the method described previously [Orrenius et al., 1992b]. Two representative areas of the basal turn and hook portion were photographed. In each area, OHCs were counted in an area that was ten pillar cell heads in length. The results are presented as the percent hair cell damage per cochlear turn.

Immunohistochemistry (IHC).

*Cochleae* were processed by a rapid decalcification method, paraffin-embedded, and sectioned to obtain midmodiolar sections. For IHC processing, primary antibody (1:100 titer) and secondary fluorescent labelled antibodies (1:200 titer) were used. Slides were imaged by Leica confocal microscope (Leica America).

RNA Isolation.

*Cochleae* were pared down to the bone, crushed in liquid nitrogen followed by extraction in 500 µl of TRI reagent. 0.1 ml of chloroform was added, and the tube was shaken vigorously for 15 seconds and centrifuged at 12,000×g for 15 min. RNA was extracted by washing the pellet with 0.5 ml ice-cold isopropanol followed by cold 75% treated ethanol. The ethanol was removed and the tube was air dried briefly. The RNA pellet was resuspended in nuclease free water and RNA levels were determined using optical density readings corresponding to wavelengths of 260 nm, 280 and 320 nm using a spectrophotometer (Eppendorf BioPhotometer, Hamburg, Germany).

Real Time RT-PCR.

500 ng of total RNA was converted to cDNA using iScript cDNA Synthesis Kit (Bio-Rad, Hercules, CA). The reaction mixture was set up as follows: lng of total RNA, 4 μl of iScript reaction mix, 1 μl of iScript reverse transcriptase, nuclease free water to bring the total volume to 20 μl. The reaction mix was incubated at 25° C. for 5 min, 42° C. for 30 minutes and 85° C. for 5 minutes. This cDNA reaction mix was used for real time PCR, as described previously [Mukherjea et al., 2006]. Gene specific primer pairs were used for the various reactions and mRNA expression levels were normalized to the levels of GAPDH. The primer sets were purchased from Sigma Genosys (St. Louis, MO), and were as follows:

```
Rodent-GAPDH (sense):  5'-ATGGTGAAGGTCGGTGTGAAC-3'
(antisense):  5'-TGTAGTTGAGGTCAATGAAGG-3'

Rodent TRPV1 (sense):  5'-CAAGGCTGTCTTCATCATCC-3'
(antisense):  5-AGTCCAGTTTACCTCGTCCA-3'

Rodent NOX3 (sense):  5'-GTGAACAAGGGAAGGCTCAT-3'
(antisense):  5'-GACCCACAGAAGAACACGC-3'

Rodent-TNF-α (sense):  5'-CAGACCCTCACACTCAGATCA-3'
(antisense):  5'-TGAAGAGAACCTGGGAGTAGA-3'

Rodent-COX2 (sense):  5'-TGATCGAAGACTACGTGCAAC-3'
(antisense):  5'-GTACTCCTGGTCTTCAATGTT-3'

Rodent iNOS (sense):  5'-AAGTACGAGTGGTTCCAGGA-3'
(antisense):  5'GCACAGCTGCATTGATCTCG-3'
```

Statistical Analysis.

Statistical significance differences among groups were performed using analysis of variance, followed by Tukey's post hoc test.

TRPV1 has been shown to play a role in cochlear homeostasis by altering cochlear blood flow, compound action potential (CAP), cochlear microphonics (CM) [Vass et al., 1995a; Zheng et al.] and has been reported to be increased in acoustic model of tinnitus [Bauer et al.]. However, TRPV1 being a mediator of NIHL has not been shown. While, TNF-α has been shown to be an early inflammatory mediator in NIHL [Fujioka et al., 2006; Tan et al.], the potentiation of TRPV1 activity by TNF-α in NIHL has not been shown. NIHL is shown here to induce auditory brainstem recording (ABR) threshold shifts of 25-50±8 dB in rats at the frequencies 8, 16 and 32 kHz tested (FIG. 14.A.), and to be associated with increased cochlear TRPV1 and TNF-α expression. Scanning Electron Microscopic (SEM) images of the organ of *Corti* show ~40-50% loss/damage of stereocilia on outer hair cells (FIGS. 14.B. and 14.C.) in the NE animals. The expression of cochlear stress and inflammatory genes measured by qPCR at 48 h and 21 d following NE were elevated in a time-dependent manner. Interestingly, the increases for TRPV1 and TNF-α were greater at 21 d, as compared to 48 h. TRPV1 expression was increased to 2.0±0.2 fold at 48 h and further increased to 3±0.2 fold by 21 days while TNF-α expression increased from 2.1±0.2 to 3.5±0.2 fold over the same time period. NOX3, iNOS and COX2 expression increased significantly at 48 h to 2.2±0.4, 1.5±0.2, and 2.3±0.2 fold respectively, with no further changes at 21 days post NE (FIG. 14.D.). NE parameters were (122 dB for 1 hr, OBN, centered at 16 kHz). These findings establish the dysregulation of TRPV1, TNF-α, and NOX3 as an early and chronic event in NIHL.

NE has been linked to immediate increase in ROS generation and persistent oxidative stress in the cochlea2, leading to generation of reactive oxygen species such as: hydroxyl anion ($OH^-$), superoxide anion ($O^{2-}$) and hydrogen peroxide ($H_2O_2$). To establish the role of TRPV1 channel in NIHL in vitro and to delineate the TNF-α potentiation of TRPV1 (Vanolloid Receptor 1—VR1) induced $Ca^{2+}$ pathway HEK cells stably transfected with VR1 (HEKVR1) and immortalized organ of *Corti* (UB/OC-1) cells were used. The cells were loaded with $Ca^{2+}$ dye—Fluo-4AM, washed and imaged every 3 seconds using Leica confocal microscope in a time series till 300 seconds. Basal fluorescence was captured for 10 scans and 100 μM $H_2O_2$ was added at 30 seconds and the resulting fluorescence captured. $H_2O_2$ treatment elicited a rapid robust $Ca^{2+}$ response within 10 seconds with fluorescence returning to baseline by 60 seconds in the HEKVR1 cells, while a delayed $Ca^{2+}$ response at 30 seconds was seen in UB/OC-1 cells that returned to baseline by 3 minutes, possibly due to the presence of fewer TRPV1 channels. However, pretreatment with TNF-α (0.1p g/ml) for 60 seconds prior to treatment with $H_2O_2$ causes a prolonged sustained calcium release in both HEKVR1 as well as UBOC1 cells that is observed till 5 minutes (FIGS. 15.A. and 15.C.). Pictorial representation of baseline, maximal and fluorescence after 5 mins has been shown in HEKVR1 cells (FIG. 15.B.) and in UBOC1 cells (FIG. 15.D.). This increase in $Ca^{2+}$ release is ERK dependent, as pre-treatment of the cells with 10 μM PD98059 (ERK inhibitor) shows little or no calcium release in both HEKVR1 as well as UBOC1 cells.

ERK activation has been reported to contribute to the pathology of noise induced hearing loss [Meltser et al.; Maeda et al.]. Increase in ERK phosphorylation in UBOC1 cells treated with 100 μM $H_2O_2$ was observed in a time dependent manner (FIGS. 15.E. and 15.F.), with highest expression seen at 60 minutes post treatment. Additionally, inhibition of ERK activation by PD98059 prior to treatment with 100 μM $H_2O_2$ showed significantly decreased cell death by TUNEL (FIG. 15.G.). Interestingly, ERK activation by TNF-α (0.1 μg/ml) treatment elicited a bell shaped curve with highest expression seen at 30 minutes post treatment (FIGS. 15.H. and 15.I.) in UBOC1 cells. Furthermore, inhibition of TRPV1 by transfection of UBOC1 cells with siRNA did not elicit a strong $Ca^{2+}$ response with either 100 μM $H_2O_2$ or 100 μM $H_2O_2$+TNF-α (0.1 μg/ml) (FIG. 15.J.) and inhibited apoptosis by 100 μM $H_2O_2$ as seen by TUNEL staining (FIG. 15.K.).

To further confirm the role of TNF-α in potentiating the $Ca^{2+}$ response via the TRPV1 channel, HEKVR1 cells were treated with a direct TRPV1 agonist (Capsaicin (2.5 μM)) and with TNF-α (0.1 μg/ml) for 30 minutes. A tremendous increase in $Ca^{2+}$ was observed with Capsaicin treatment (741±22%), over basal fluorescence, which was increased to 3146±532%, with the addition of TNF-α (FIGS. 15.L. and 15.M.). These data demonstrate that 1) TRPV1 is essential for increased $Ca^{2+}$ release seen in NIHL, 2) accompanying inflammation by TNF-α potentiates this response and 3) this response is ERK dependent.

TRPV1 expression has been reported in the various cells of the cochlea including outer and inner hair cells, supporting cells, marginal cells of the stria vascularis, inner and outer pillar cells as well as in the Hensen's cells and the spiral ganglion [Zheng et al.; Liedtke et al.]. Direct activation of TRPV1 by capsaicin decreases CAP and CM threshold reversibly and desensitization was observed on prolonged perfusion [Zheng et al.]. Capsaicin (TT) administration (50 μl of 0.1 μM) caused a transient ABR threshold shift for 24 hours without recruitment of apoptotic pathway [Mukherjea et al., 2011].

Figure 16A:
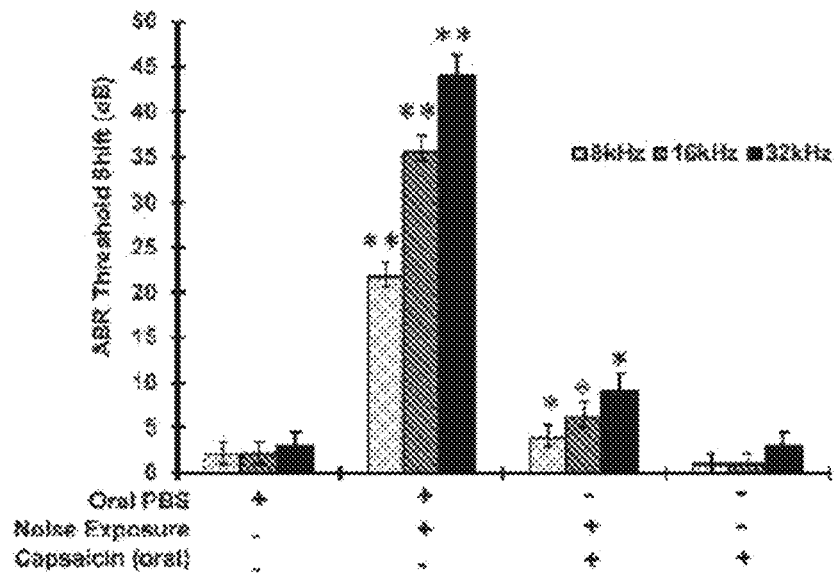
FIG. 16.A.
Figure 16B:
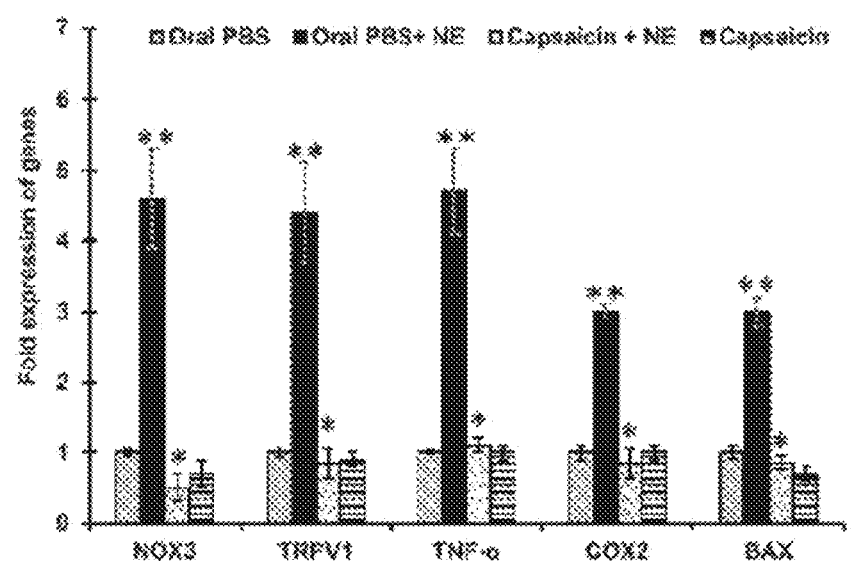
Figure 16C:
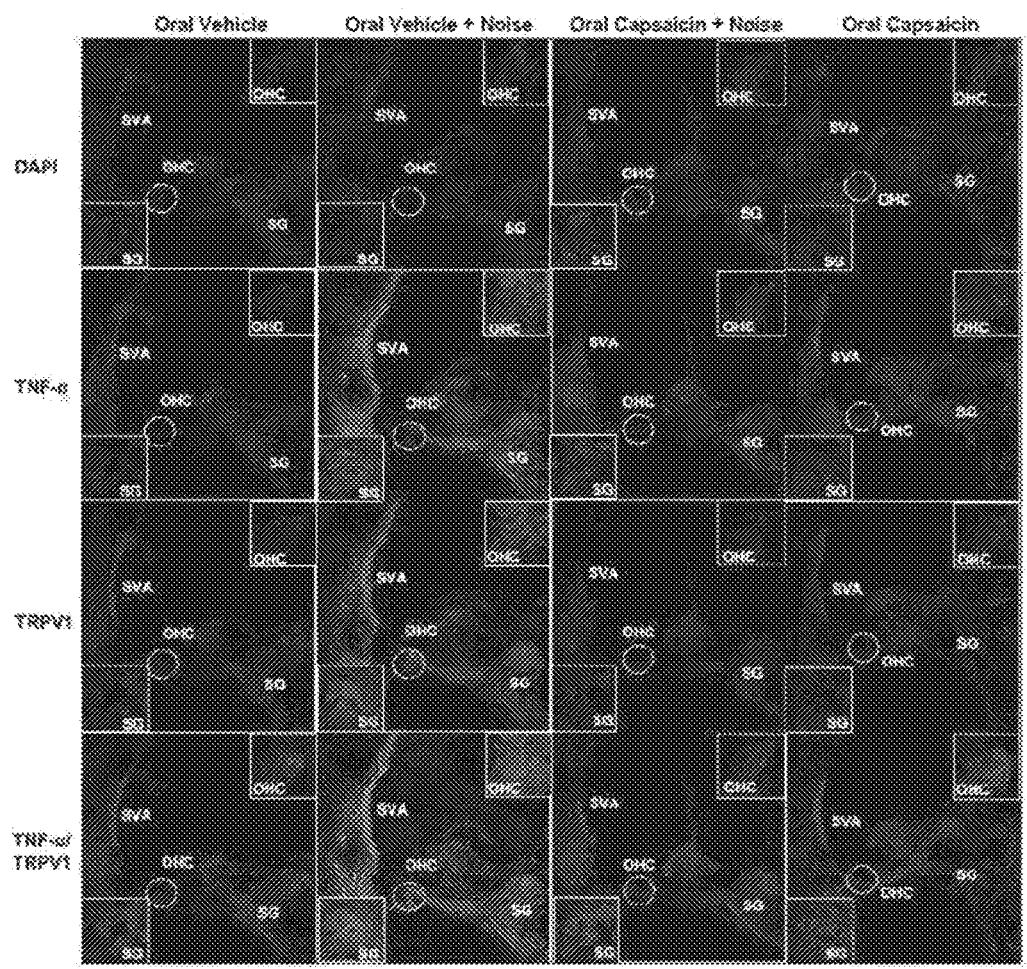

Preconditioning of the TRPV1 receptor in the rat cochlea by oral administration of capsaicin is shown here to protect from NIHL. Male Wistar rats weighing 200-250 gms were used. ABRs from naïve rats were recorded. Rats were then treated with oral phosphate buffered saline (PBS—1 ml) or capsaicin (1 ml of 20 mg/ml) starting 24 hrs prior to NE, on the day of NE, and 24 hrs post NE. The final ABRs were recorded 21 days post NE. Cochleae were collected for various biochemical tests and immunohistochemistry. At least 6 animals were used per treatment group. NE caused an ABR threshold shift of 21.6±1.7, 35.5±1.9 and 43.9±2.3 dB threshold shift at 8, 16 and 32 kHz respectively. Oral capsaicin treatment completely protects from NIHL (3.9±1.4, 6.1±1.8 and 8.9±2.1 dB threshold shift at 8, 16 and 32 kHz respectively), there is no significant change in ABR threshold shift compared to control. Oral Capsaicin administration did not show any significant ABR threshold shift compared to control (1±1.1, 1±1.1, 3±1.6 dB threshold shift at 8, 16 and 32 kHz respectively). Statistical significance was calculated using one way ANOVA with Tukey's post-hoc analyses, p<0.05 (FIG. 16.A.). Gene expression analyses of the various stress response, inflammatory and apoptotic markers by qPCR of the rat cochleae showed that oral capsaicin treatment inhibits the upregulation of all the stress markers by NE (FIG. 16.B.). Fold increases in gene expressions by NE over oral PBS treated control rat cochleae were as follows: TRPV1 (4.4±0.7), TNF-α (4.7±0.6), NOX3 (4.6±0.7), COX2 (3±0.2), Bax (3±0.1), while the oral Cap+NE group showed basal levels of gene expression where TRPV1 (0.85±0.2), TNF-α (0.9±0.1), NOX3 (0.5±0.2), COX2 (0.84±0.2) and Bax (0.86±0.1). Oral Capsaicin treatment alone showed basal levels of all genes namely: TRPV1 (0.9±0.1), TNF-α (1±0.15), NOX3 (0.7±0.2), COX2 (1±0.1) and Bax (0.69±0.1). Fluorescent immunohistochemical staining of the mid modiolar sections of the rat cochleae stained with TRPV1 and TNF-α antibody shows a robust increase in fluorescence in NE cochleae which is inhibited by oral capsaicin treatment (FIG. 16.C.). Preconditioning of the TRPV1 receptor by direct TRPV1 activation by oral capsaicin treatment is demonstrated here to prevent NIHL, suggesting TRPV1 as a major player in the inflammatory cascade in NIHL.

Example 9. Inhibition of the TNF-α Signaling Ameliorates NIHL

A TNF-α inhibitor, ETA, was administered to rats by two routes (either TT or sc) and either as a pretreatment preventative regimen or as a rescue treatment after NE in the male Wistar rat. Sequestering the free floating TNF-α by ETA pretreatment either 3 days or 7 days prior to NE will prevent TNF-α potentiation of the TRPV1 induced calcium response leading to chronic inflammation. Rescue ETA treatment if given within a window period of either 2 hours or 24 hours post NE, alleviates the TNF-α induced inflammation to some extent.

ABR measurements were conducted in naïve male Wistar rats. Single ETA administration (TT-250 µg/50 µl, or s.c:3 mg/kg) or sterile PBS (TT-50 µl, s.c:1 ml) was performed either before or after NE according to the experimental design. Post treatment ABR assessments were performed 21 days post NE. The cochleae were collected and processed for various biochemical and immunohistochemical assays. At least 4 animals were used per treatment group. NE causes (36.25±3, 45±3 and 48.75±2.5 dB) ABR threshold shifts at 8, 16 and 32 kHz. ABR analyses indicate that 3 day pre-treatment with TT-ETA provides best otoprotection from NE, (1.25±1.25, 0 and 3.75±1.8 dB) while subcutaneous ETA pretreatment provides a statistically significant protection (4±1.6, 8±2.5 and 11±18 dB) at 8, 16 and 32 kHz respectively (FIG. 17.A.).

Figure 17A:
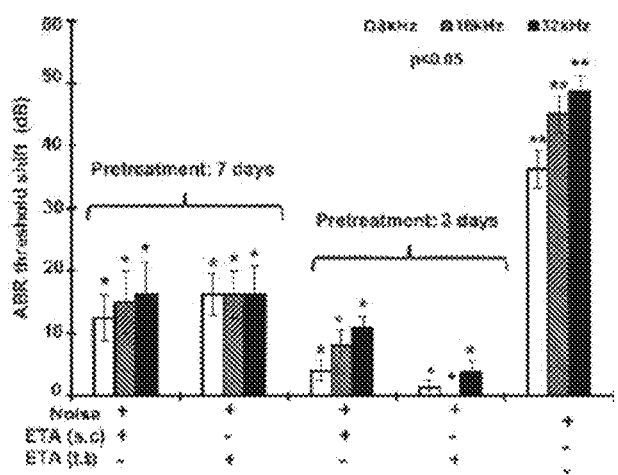
FIG. 17.A.
Figure 17B:
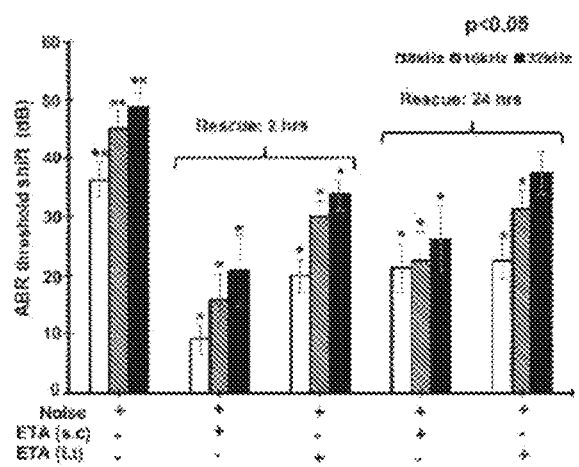
Figure 17C:
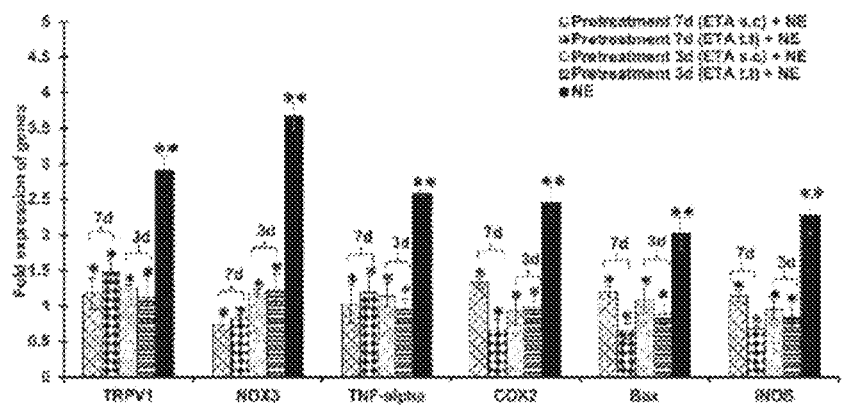
Figure 17D:
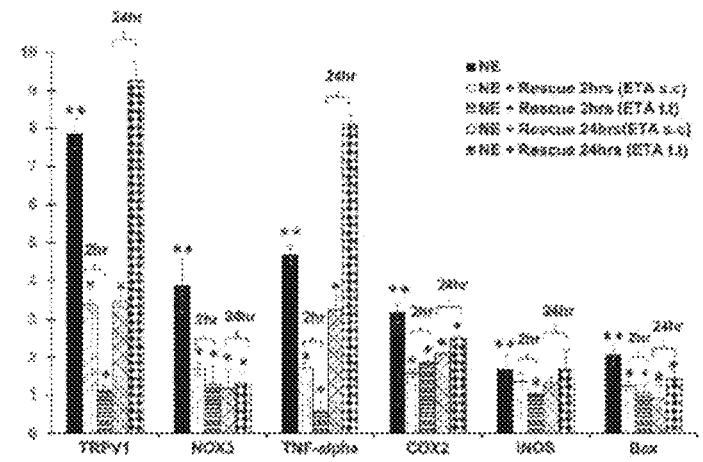

The 7 day pretreatment paradigm yielded partial protection from NE: TT ETA showed (16.25±3.25, 16.25±3.75 and 16.25±4.6 dB), while s.c ETA showed (12.5±3.6, 15±5 and 16.25±5.3 dB) threshold shifts at 8, 16 and 32 kHz (FIG. 17.A.). Thus, the severity of hearing loss from NE can be prevented up to 7 days in a time and route dependent manner. Additionally, in case of unanticipated NE, rescue treatment when initiated within 2 hours show (TT ETA: 20±2.6, 30±2.7 and 33.75±2.7 dB), and (s.c. ETA: 9.16±2.6, 15.8±4.5 and 20.8±6.0 dB), threshold shifts at 8, 16 and 32 kHz respectively (FIG. 17B). When initiated at 24 hours post NE (TT ETA: 22.5±2.9, 31.25±3.2 and 37.5±3.7 dB) and (s.c. ETA: 21.25±3.9, 22.5±4.9 and 26.25±5.6 dB ABR threshold shifts at 8, 16 and 32 kHz were recorded (FIG. 17.B.). In the rescue situation, ETA when administered post NE, subcutaneously provides better protection than the localized TT delivery possibly due to the resulting vasoconstriction and swelling of the cochlea decreasing the permeability of the oval window thus making it difficult for the 150 kD ETA molecule to enter. However, subcutaneous ETA travels via the blood and has a better chance of reaching the target site. The cochlear gene expression analyses of the different treatment groups are reflective of the ABR threshold changes. In FIG. 17.C., pretreatment with ETA prevents the NE induced up regulation of TRPV1, TNF-α, NOX3, COX2, iNOS and Bax. Similar results are seen in the rescue group when ETA is administered within 2 hours of NE. The localized rescue treatment by TT injection at 24 hours is unable to decrease the TRPV1, TNF-α and COX2 to basal levels (FIG. 17.D.). This could be attributed to the cochlear response to NE and the treatment being administered beyond the critical window of opportunity, thus attenuating the hearing loss due to NE, it is unable to rescue completely. The other explanation could be that not enough ETA gets to the cochlea, thus unable to sequester all the TNF-α produced.

TRPV1 channel dysregulation is shown here to be essential in hearing loss due to NE, and the accompanying inflammation caused by TNF-α potentiates this. In addition, preconditioning of the TRPV1 receptor by oral consumption of capsaicin can prevent the NIHL or sequestration of TNF-α by FDA approved ETA can also prevent NIHL. Although it has been shown that ETA administration 15 minutes after NE (106 dB for 30 minutes) will ameliorate temporary threshold shift at 180 minutes [Arpornchayanon et al.], possibly due to improved cochlear blood flow, it was not clear whether ETA administration will prevent or treat the permanent hearing loss seen at 21 days from NIHL.

Exposure to a period of intense noise results in hearing loss which is associated with increases in the expression of inflammatory-related genes. Furthermore, inhibition of the cytokine, TNF-α, abrogated or reduced hearing loss. The optimal protective responses with etanercept were observed when administered by subcutaneous injections either 3 d prior to or 2 h post noise exposure. These results suggest that inflammatory cytokines are important players in mediating NIHL and that etanercept could be an effective drug for the treatment and prevention of NIHL.

The present data demonstrate that TNF-α is a critical player in initiating NIHL. Increased staining for TNF-α could be observed throughout the cochlea, including the OHCs, stria vascularis, spiral ganglia and spiral ligament. The source of the TNF-α is likely the cochlea which is possibly supplemented later by circulating immune cells. Administration of ETA, by either the IT or subcutaneous routes, reduced the levels of cochlear TNF-α. This suggests effective penetration of the drug into the cochlea via both of these routes. The importance of intra-cochlear TNF-α in mediating NIHL is supported by the fact that intra-tympanic etanercept effectively reduced NIHL when administered prior to or following NIHL.

Interestingly, etanercept was also effective in regulating other inflammation-related genes, such as COX-2, iNOS, NOX3 and TRPV1. This suggests that the expression of these genes is positively regulated by TNF-α in the cochlea. TRPV1 interaction with NOX3 facilitates cisplatin-mediated inflammation in the cochlea and hearing loss [Mukherjea et al., 2011]. Up-regulation of these genes by TNF-α could serve as a way of prolonging the inflammation in the cochlea, which likely contributes to NIHL. The efficacy of ETA against NIHL when administered following noise exposure suggest that there is a small time window for treating patients exposed to noise trauma. A preferred time point may be 2 h post noise exposure when the drug is administered by the subcutaneous route, even though protection was observed when treatment was delivered 24 h post noise exposure. The lower efficacy of the IT route of ETA administration post noise exposure is a bit puzzling, as one would expect the drug would be more effective when delivered close to its site of action.

Etanercept may be used prophylactically or soon after noise exposure to reduce NIHL. The drug might also be effective against age-related hearing loss and cisplatin-induced hearing loss, which involves activation of similar inflammatory pathways.

Example 10A. Capsaicin and Etanercept Treatment Regimen in Combination

Two clinically used drugs, capsaicin and ETA, are provided for the treatment of NIHL. Molecular interplay between TRPV1, NOX3 and inflammatory cytokines networks in the cochlea following cochlear trauma provides at least part of the mechanism by which this treatment combination provides for treatment of NIHL is a subject. Cisplatin and noise trauma are demonstrated here to promote the generation of ROS (primarily via the NOX3 pathway) which enhance activation and induction of local TRPV1 channels in the cochlea, triggering production of inflammatory cytokines (such as TNF-α). Reciprocal regulation among members of this "TNT triad" (TRPV1, NOX3, TNF-α) network occurs, such that ROS and TNF-α could potentiate TRPV1 activity.

Figure 18A:
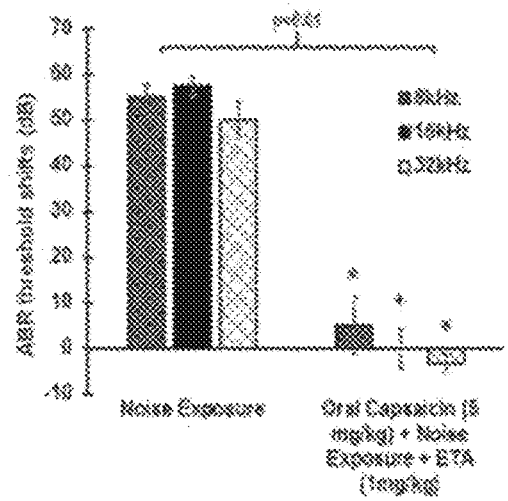
FIG. 18.A.
Figure 18B:
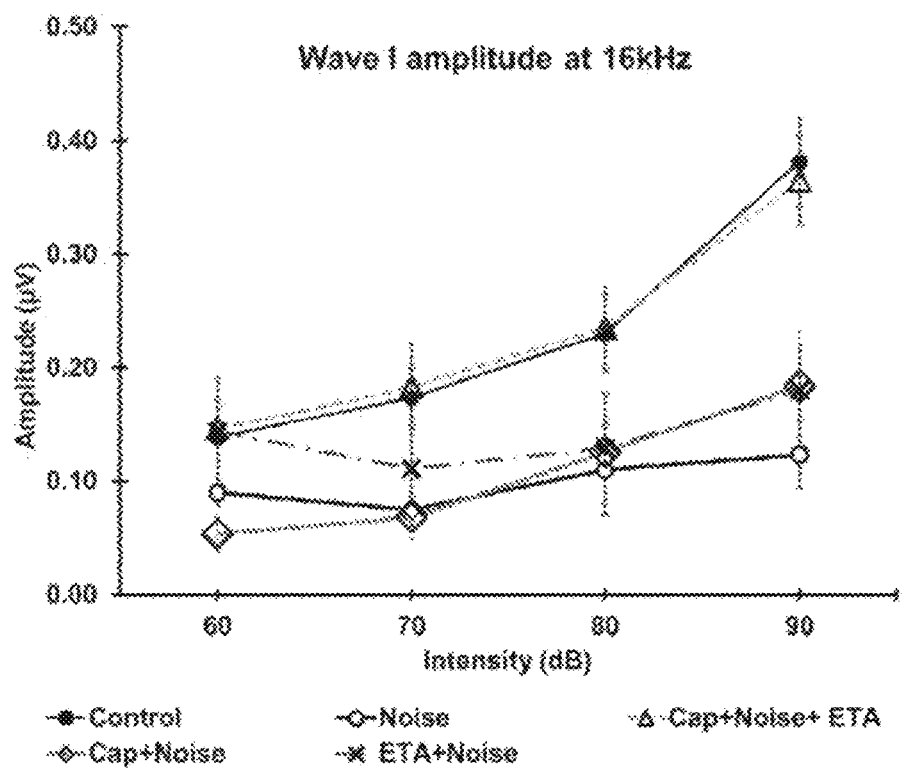

NIHL results from the synergistic actions among members of this TNT triad and that disruption of one or more members of this group could dismantle this synergy and reduce NIHL. The present data demonstrates that capsaicin or ETA added alone protects against NIHL. However, when administered to a subject at the same time, by different routes of administration, essentially complete protection of ABR thresholds is demonstrated, including restoration of wave I amplitude to pre-noise exposure levels (FIG. 18).

Current treatment for the restoration of wave I amplitude involves round window application of adeno-associated viral constructs of neurotrophin-3 (NT3), and does not provide complete restoration [Chen et al., 2018]. This magnitude of prevention/rescue of hearing loss (permanent threshold shift) and restoration of wave I is therefore preferably to be provided by the combined desensitization and inhibition of TRPV1 and TNF-α, respectively. Based on the present studies, the drug combination would allow for the use of considerably lower doses of ETA and capsaicin, thereby reducing the severity of potential side effect in humans.

Figure 19A:
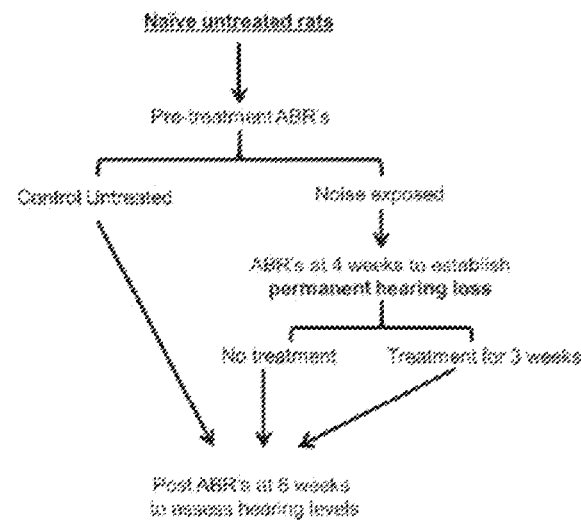
FIG. 19A. Schematic representation of treatments. Pretreatment ABRs were performed. Ten rats (with 2 ears/cochleae each) were noise exposed and ABR's were repeated at 4 weeks post noise exposure to establish permanent threshold shifts. The noise exposed rats with permanent hearing loss were then divided into two groups of 5 rats each. One group did not get any treatment and their post treatment ABR's were determined after 8 weeks. The other group of noise exposed rats with permanent hearing loss received the combination treatment with oral capsaicin (5 mg/kg) for 3 days+single ETA (1 mg/kg, s.c) on day 2, for 3 weeks. Post treatment ABR threshold values were evaluated at week 8 post NE in all the animals. Three control rats (total of 6 ears/cochlea) were untreated and unexposed to noise. Values are expressed as the mean±SEM of the indicated number of cochlea per group. * indicate statistically significant differences between the noise-exposed and the control groups. ** indicate statistically significant differences between noise exposed and the noise exposed+treated groups ($p<0.05$). Values are expressed as the mean±SEM.
Figure 19B:
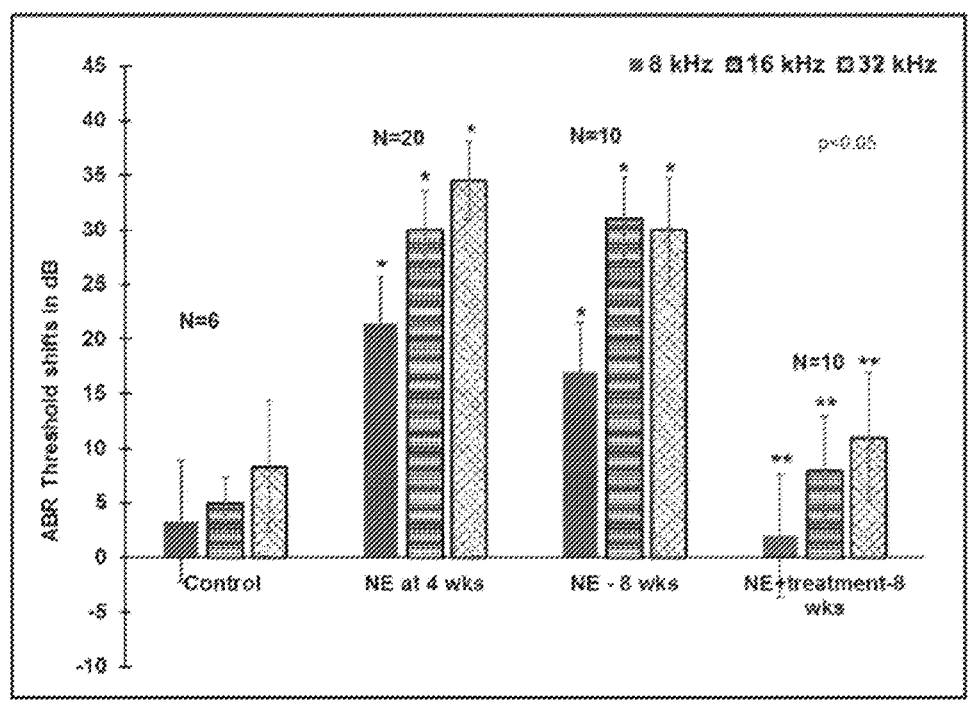
FIG. 19B. Graphical representation of ABR threshold shifts grouped according to treatments. The solid grey bar depicts threshold shifts observed at 8 kHz, the striped bar: 16 kHz and the checkered bar: 32 kHz. The data indicate that the control group show threshold shifts of ~0-10 dB at 8 weeks, while the noise exposed group measured at 4 weeks show 22-37 dB, the noise exposed group with no treatment when rechecked at 8 weeks showed no difference in hearing loss compared to the 4 week grouped according to frequency measured. In this figure the white solid bar represents the control untreated group, the dotted square bar represents the noise induced hearing loss group at 4 weeks, the solid grey bar represents hearing levels of rats that were treated after the establishment of noise induced hearing loss and the black solid bar represents the hearing loss levels of the noise induced hearing loss group that did not receive any treatment at week eight.
Figure 19C:
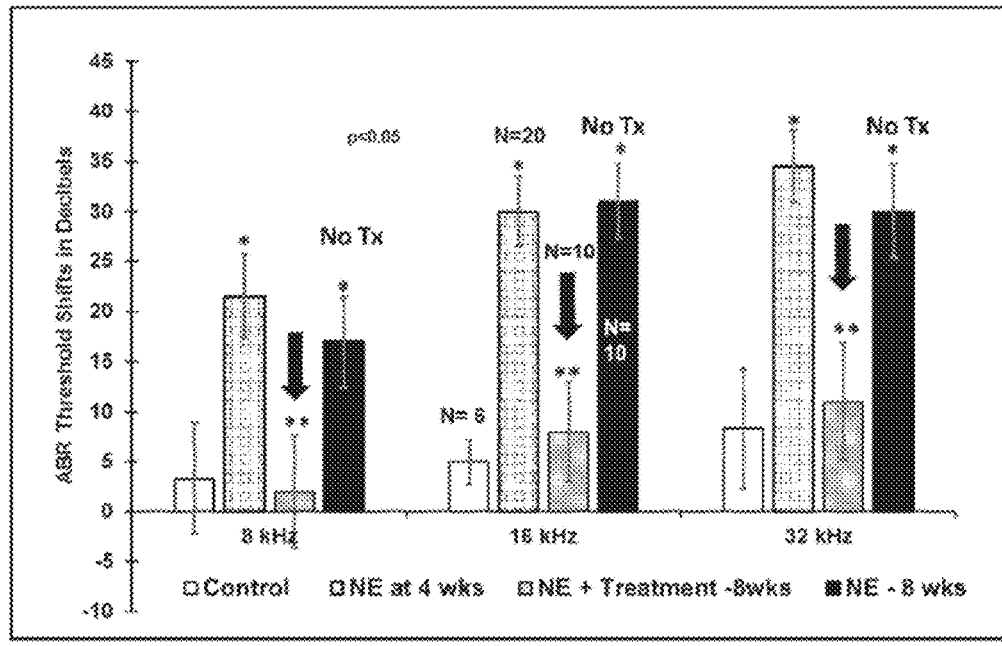
FIG. 19.A.
Figure 20A:
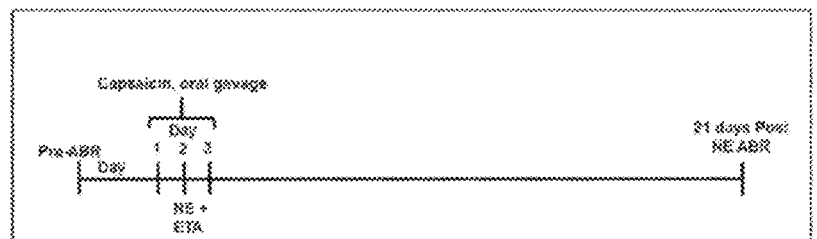
FIG. 20A. Preventive treatment: Rats were pretreated with oral vehicle or capsaicin (10 mg/kg or 5 mg/kg) 24 hours prior to NE, followed by oral vehicle or capsaicin again on the day of NE. ETA (1 mg/kg s.c.) was administered 2 hours following NE. Post-treatment ABRs were performed 21 days later (N=6).
Figure 20B:
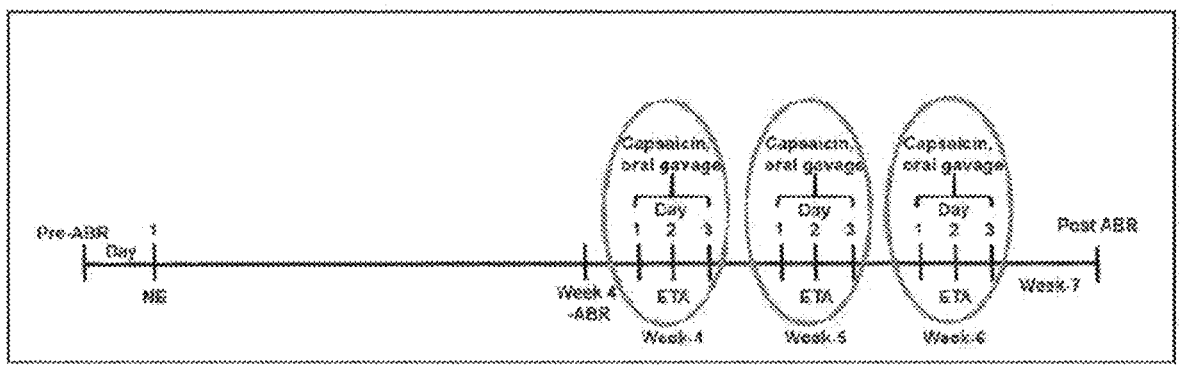
FIG. 20. A-FIG. 20.B. Combination treatment paradigms.
Figure 21:
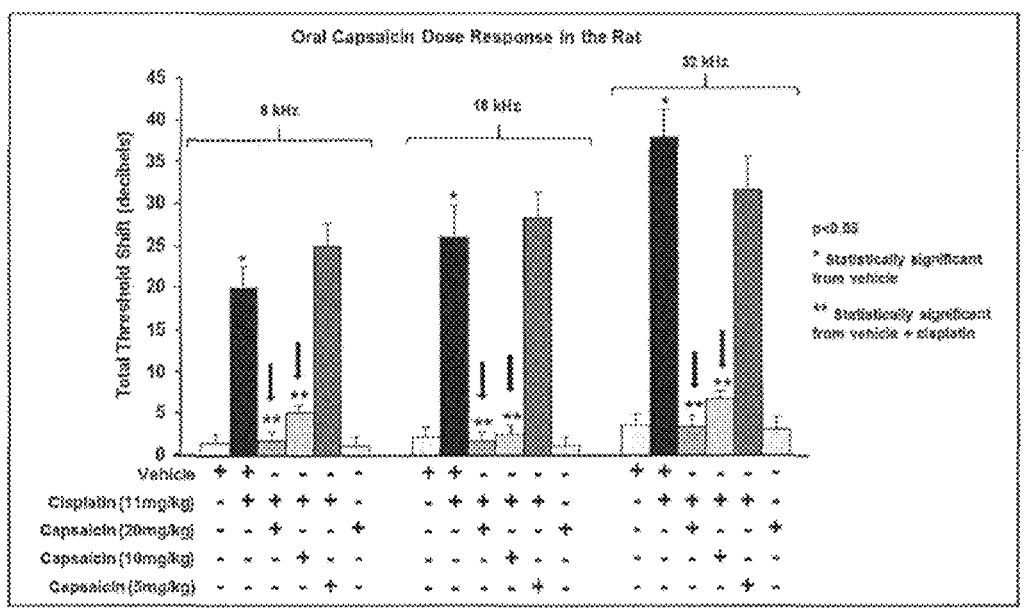
FIG. 21. Capsaicin inhibits cisplatin-induced hearing loss in a dose dependent manner. ABR threshold shifts were recorded in naïve Wistar rats, pre-treated with vehicle (oral PBS) or oral capsaicin (20, 10 or 5 mg/kg), 24 h prior to cisplatin (11 mg/kg, i.p). Post treatment ABR thresholds were measured at 72 h after cisplatin. Cisplatin treatment causes a significant increase of 15-40 dB threshold shifts at 8, 16 and 32 kHz compared to control. Capsaicin pre-treatment attenuated cisplatin induced hearing loss at all frequencies tested in a dose dependent manner with maximum protection seen at 20 mg/kg dose followed by 10 mg/kg dose while 5 mg/kg dose did not show any protection. Black arrows indicate significant decrease in threshold shifts when compared to cisplatin treatment. (*Indicates significant difference from control; **indicates significant difference from cisplatin treatment, $p<0.05$, n=9).

The present methods and treatments provide a superior treatment over other existing technologies, in that the administration of at least two drugs either as pre-treatment or as rescue, protects a subject from hearing damage and/or hearing loss. It is shown herein that hearing can be restored even when treatment is administered as late as 28 days post traumatic noise exposure (FIG. 19). The length of time between exposure and treatment indicates a possible regeneration event occurring in the auditory hair cells, synapses, spiral ganglion or auditory nerve fibers.

Example 10B. Capsaicin and Etanercept Treatment Regimen in Combination

FIG. 23A is a schematic showing the experimental paradigm used in Example 10B. Pre-treatment baseline ABRs were performed in naïve male Wistar rats. The rats were then used either as sham controls (no noise exposure) or exposed-noise (122 dB, OBN centered at 16 kHz for 1 hour). Post noise exposure ABRs were repeated at 4 weeks to establish permanent threshold shifts (PTS). All noise exposed rats showed PTS and were then divided into two groups, a control group (no treatment) and a treatment group which was administered a combination of oral capsaicin (5 mg/kg, once daily) for 3 days and a single ETA (1 mg/kg, s.c., weekly) on day 2, for three weeks, consistent with the treatment regimen schematically shown in FIG. 23C. Final ABR threshold values were evaluated at week 9 post noise exposure.

As shown in FIG. 23B, the sham control (labeled "Control" in FIG. 23B) showed threshold shifts of approximately 5-10 dB as measured at 9 weeks, while the noise-exposed group showed 20-40 dB PTS as measured at 4 weeks ("PTS-4 wks"). The noise-exposed group with no treatment when rechecked at 9 weeks ("PTS-9 wks") showed no significant difference in hearing loss compared to the 4 week ABR. Both the 4 week and the 9 week threshold shifts of noise alone groups were significantly higher than that of the control. The noise group that received the combination treatment after the establishment of PTS showed a significant restoration of hearing at 9 weeks, with average hearing threshold shifts of approximately 5-13 dB ("PTS+Cap+ETA—9 wks"). Noise-exposed groups treated with capsaicin alone and ETA alone did not show as significant a restoration of hearing at 9 weeks, with average hearing threshold shifts of approximately 15-25 dB and 25-38 dB, respectively.

Values shown in FIGS. 23A-23C and otherwise provided with respect to this Example 10B are expressed as the mean±SEM. Statistical significance was analyzed using the ANOVA and Tukey's host hoc analysis.

Prophetic Example 11. Regimen for Human Hearing Loss

Capsaicin has been shown to regenerate neuronal outgrowths (1) and re-innervation of cornea-lens (2). Thus capsaicin and TNF-alpha combination may be used to slow the progression of inflammation related sensorineural diseases like tinnitus, Meniere's disease, ophthalmic inflammatory progressive disorders, neuropathic pain, Alzheimer's progression and inflammatory disorders.

The present example is provided to disclose a regimen of capsaicin and a TNF-α inhibitor capable of affecting hearing sensitivity in an animal, particularly in a human. for improving the hearing in an animal, particularly in a human. The table below shows a common classification system used to assess hearing sensitivity level expressed as a range of decibels (dB).

| Degree of hearing loss | hearing threshold in Decibels (dB HL) |
|---|---|
| Normal | −10 to 15 |
| Slight | 16 to 25 |
| Mild | 26-40 |
| Moderate | 41-55 |
| Moderately severe | 56 to 70 |
| Severe | 71 to 90 |
| Profound | 91+ |

Clark, J.G. (1981). Asha, 23, 493-500.

The higher the decibel level number used to describe a subject's hearing level, the poorer that subject's hearing is considered to be. For example, when a person can only hear sounds that are about 30 dB, they are considered to have mild hearing loss.

The proposed human equivalent dose (HED) of ETA for recovery from NIHL is about 12 mg/70 kg person/week for 3 weeks. This is one-eighth the total dose of ETA currently used in the treatment of psoriasis/week.

Matteson et al., [2] show that 25 mg ETA twice a week for 24 weeks has no side effects. Thus, the present proposed model of one administration for three weeks is reasonable.

In further embodiments, however, the HED is converted from the animal dosage described and used herein with respect to naïve male Wistar rats using the known formula. For example, one known HED conversion is:

$$\frac{\left(\text{animal dosage in } \frac{mg}{kg}\right) \times (\text{average human weight})}{(\text{animal specific conversion factor})}$$

wherein the average human weight is generally 60-70 kg and the animal specific conversion factor is 6.2 for naïve male Wistar rats. For example, for a 1 mg/kg dosage used in a Wistar rat, the HED would be $$\frac{\left(1 \frac{mg}{kg}\right) \times (60 \text{ kg})}{6.2},$$

or 9.68 mg.

In a particular embodiment, in which the HED is calculated as set forth above, it is anticipated that the dosage of capsaicin provided to a human subject will be from about 5 mg, or 10 mg, or 15 mg, or 20 mg, or 25 mg, or 30 mg, or 35 mg, or 40 mg, or 45 mg to about 50 mg, or 55 mg, or 60 mg, or 65 mg, or 70 mg, or 75 mg, or 80 mg, or 85 mg, or 90 mg, or 95 mg, or 100 mg, or in some embodiments, from about 35 mg to 60 mg, or from about 45 mg to 50 mg. Further in some regimens, the capsaicin will be provided to a human subject for 3 days, or 6 days, or 9 days. In an embodiment, the capsaicin will be provided to a human subject for a single set of 3 consecutive days, or two sets of three consecutive days, or three sets of three consecutive days, each set is separated by at least 3 days, or at least 4 days, or at least 5 days, or at least 6 days, or at least 7 days. A dosage of a TNF-α inhibitor, for example etanercept, would be provided at a dosage amount from about 4 mg, or 4.5 mg, or 5 mg, or 5.5 mg, or 6 mg, or 6.6 mg, or 7 mg, or 7.5 mg, or 8 mg, or 8.5 mg, or 9 mg, or 9.5 mg, or 10 mg to 10.5 mg, or 11 mg, or 11.5 mg, or 12 mg, or 12.5 mg, or 13 mg, or 13.5 mg, or 14 mg, or 14.5 mg, or 15 mg on day 2 of the three consecutive days, or in some embodiments from about 4.5 mg, or 5 mg, or 5.5 mg, or 6 mg, or 6.5 mg, or 7 mg, or 7.5 mg, or 8 mg, or 8.5 mg, or 9 mg, or 9.5 mg to 10 mg, or 10.5 mg, or 11 mg, or 11.5 mg, or 12 mg, or 12.5 mg, or 13 mg, or 13.5 mg, or 14 mg, or in further embodiments, from amount 7 mg to 12 mg, and on day 2 for at least one set of the three consecutive days of the regimen, or at least two sets of the three consecutive days of the regimen, or all three sets of the three consecutive days of the regimen.

It is anticipated this regimen will, in some embodiments, be provided to a human subject for 3 weeks. In a specific embodiment, capsaicin is administered on days 1, 2 and 3 of a given week, for three consecutive weeks, with a dosage of etanercept administered on day 2 of each of the three consecutive weeks. In some embodiments, the capsaicin s formulated as an oral preparation and will be provided, for example, as a capsule. In some embodiments, the TNF-α inhibitor (e.g., etanercept) is formulated as a trans-tympanic injection, sub-cutaneous injections, or as an orally bioavailable formulation.

Auditory threshold shifts after 4 weeks post traumatic noise exposure are referred to in the literature as "permanent", since they do not revert back to baseline and remain elevated [4]. Thus, for the purpose of these proposed experiments threshold shifts at 4 weeks post noise trauma is essentially permanent threshold shift (PTS). Monoclonal antibodies—Rahman [5] and Van Wijk [6] indicate that monoclonal antibody against TNF-alpha may be effective in sensorineural hearing loss and accompanying tinnitus in humans. However, others dispute these findings. Thus, the status of the TNF-α antagonist alone for recovery of NIHL was not clear.

The use of a combination of capsaicin and the TNF-α inhibitor, for example, etanercept (ETA), an anti-TNF-α monoclonal antibody such as adalimubab, golimubab, infixamab, or a combination thereof, is disclosed herein as part of a method for improving the hearing acuity of a human subject. It is envisioned that the method for improving hearing acuity in a human subject may be provided by providing the subject with capsaicin as an oral formulation, such as in a capsule. A capsaicin capsule is envisioned to be administered to a subject so as to provide a dose of about 10 mg/kg or about 5 mg/kg to the subject. At approximately the same time, or simultaneously with the administration of capsaicin, the subject will be administered a low dose of etanercept. The delivery form of the etanercept may comprise a subcutaneous delivery form that provides for the low dose release of the etanercept for an about two week, three week, or even four week period. It is envisioned that the total amount of etanercept that will be delivered to the subject over the 3 week period will be about 10-20 mg, or about 15-25 mg, or 20-30 mg. The general range for the slow dose delivery of etanercept or other TNFα inhibitor, to a subject, may therefore be from about 10 mg to about 30 mg.

It is expected that this treatment will result in an improvement in the hearing acuity level of the subject that is improved over those baseline hearing acuity levels of the subject prior to treatment. Where an improvement in hearing acuity level in a subject remains above the subject's hearing acuity level as it existed prior to the treatment for at least 4 weeks, the improvement, is considered to be permanent. These improvements in hearing acuity in a subject are characterized in a calculated "threshold shift" in the subjects hearing. This "threshold shift" is reflected in the change in the decibel level at which a subject is able to hear, that occurs after an oto-changing event. For example, where a subject is exposed to noise trauma, it would be expected that the decibel level of sound that the subject is able to hear will be increased, reflecting a loss in the subject's ability to hear sounds are lower decibel level. The difference between the decibel level at which the subject could hear before the noise trauma, subtracted from the decibel level at which the subject can hear after the noise trauma, provides a measure of the "shift" that has occurred. In this example, where hearing acuity would have been expected to worsen, the "shift" will reflect a negative number.

In contrast, where a treatment is provided to a subject that improves the hearing acuity of a subject, the post treatment measure of decibel level hearing after treatment is expected to be a lower decibel (dB) level. Thus, the difference between the decibel level in the subject before treatment (a relatively higher dB number) and the decibel level of hearing in the subject after the treatment (a relatively lower dB number) will reflect a positive number. The difference between these two measurements reflects the "shift," and would be expected to be a positive number in this example. Therefore, it is not the absolute dB measurement level observed that reflects the "shift" being examined, but instead the difference between the pre- and post-treatment or traumatic event dB level in a subject.

When examined as a percent change (%) in a subject's hearing acuity level pre- and post-treatment, the "shift" in dB provided as a result of measuring dB hearing acuity level pre- and post-treatment, the presently described regimens and treatment methods may be described as a percentage change, or improvement, over pre-treatment levels. With this paradigm, it is envisioned that the present regiments and treatment methods will provide an about 10%, about 15%, about 20%, about 25%, or even an about 50% or greater improvement to a subject's hearing acuity level.

It is expected that the present treatment regimens and methods may provide even a complete rescue of a subject's hearing acuity where the treatment is provided within a short time of a oto-toxic event, such as exposure to a loud noise or toxic chemotherapeutic agent. For example, where the treatment of capsaicin and a TNFα inhibitor is provided to a subject within 24 to 48 hours, or even within up to 30 days, of a traumatic hearing acuity compromising event, an improvement of at least about 10%, 15%, 33%, or up to 50% may be achieved. Damage to hearing that affects the brain is not considered to reach the brain until 30 days after a hearing impairment, or even with common hearing impairing conditions including tinnitus, Menier's disease, sudden sensorineural hearing loss and age-related hearing loss. Therefore, a treatment according to the present regimen will provide opportunity to rescue and/or improve hearing acuity even these forms of hearing loss.

A subject that had not previously been measured for hearing acuity level prior to treatment, but that nonetheless is observe to have a reduced hearing capacity as compared to a population norm reference number, may also be treated according to the presently described methods. In this scenario, the subject's improvement in hearing acuity level may be gauged against the dB level of hearing the subject possesses at the time of treatment. It is expected that even in those situations, where hearing levels associated with a population norm for hearing (such as for example about 15 dB to about 30 dB) may not be achieved, an improvement of about 10% to about 15% over pre-treatment hearing levels will be achieved.

As part of these regimens, and in one embodiment, the subject will be provided about and about 50 mg capsaicin (such as in a capsule or aerosol form) per day for 3 days, and about 12 mg etanercept or other TNFα inhibitor, the etanercept, delivered over a 1 week or over a 3 week period of time (such as in a subcutaneous patch or other slow delivery form). The 12 mg etanercept dosing is significantly lower than those dosage regimens currently used of 100 mg a "loading" dose. As such, the etanercept dosing is described as a sub-optimal amount, at least as compared to previous work with this agent.

It is further proposed that the described treatment regimens and methods will prevent hearing loss and ear damage provided to a subject as a pretreatment.

The examples set forth above are provided to give those of ordinary skill in the art a complete disclosure and description of how to make and use the embodiments of the methods for prediction of the selected modifications that may be made to a biomolecule of interest, and are not intended to limit the scope of what the inventors regard as the scope of the disclosure. Modifications of the above-described modes for carrying out the disclosure can be used by persons of skill in the art, and are intended to be within the scope of the following claims.

It is to be understood that the disclosure is not limited to particular methods or systems, which can, of course, vary. It is also to be understood that the terminology used herein is for the purpose of describing particular embodiments only, and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

REFERENCES

The entire disclosure of each of the patent documents and scientific articles below and referred to herein is incorporated by reference for all purposes.

Acharya, N., et al. Proc Natl Acad Sci USA 114, 5005-5010 (2017).
Alas, S. & Bonavida, B. Cancer Res 61, 5137-5144 (2001).
Arpornchayanon, W., et al. Int J Audiol 52, 545-552 (2013).
Banfi, B., et al. J Biol Chem 279, 46065-46072 (2004).
Barsotti, A. et al. Atherosclerosis 155, 53-59 (2001).
Bas, E., et al. Acta Otolaryngol 129, 385-389 (2009).
Bauer, C. A., et al. Int Tinnitus J 13, 21-28 (2007).
Benco, A. et al. Reproduction 138, 553-560 (2009).
Benito, C. et al., J Neurosci 37, 4255-4269 (2017).
Bessler, H. & Djaldetti, M., Nutr Cancer, 1-7 (2016).

Bhutani, M. et al. Clinical Cancer Research, 13, 3024-3032 (2007).
Blackwell, D. L., Clarke, T. C., and National Center for Health Statistics (U.S.). Occupational differences among employed adults who met 2008 federal guidelines for both aerobic and muscle-strengthening activities: United States, 2008-2014. In National health statistics reports number 94.
Bley, K. R., Expert Opin Investig Drugs 13, 1445-1456 (2004).
Bohne, B. A., Ann Otol Rhinol Laryngol 85, 711-724 (1976).
Bohne, B. A., et al. Hear Res 223, 61-70 (2007).
Borse, V. et al., Cell Death Dis 8, e2921 (2017).
Bradford, M. M., Analytical Biochemistry 72, 248-254 (1976).
Canlon, B. & Fransson, A., Hearing Research 84, 112-124 (1995).
Caterina, M. J. & Julius, D., Annu Rev Neurosci 24, 487-517 (2001).
Chen, C. W. et al., Br J Pharmacol 140, 1077-1087 (2003).
Chen, H., et al. Gene Ther 25, 251-259 (2018).
Derry, S., et al. Cochrane Database Syst Rev, CD007393 (2009).
Di Marzo, V. & Piscitelli, F., Neurotherapeutics 12, 692-698 (2015).
Evans, P., and Halliwell, B. Ann N Y Acad Sci 884, 19-40 (1999).
Fridberger, A., et al., Proc Natl Acad Sci USA 95, 7127-7132 (1998).
Fujioka, M. et al., J Neurosci Res 83, 575-583 (2006).
Fujioka, M., Okano, H. & Ogawa, K., Front Pharmacol 5, 287 (2014).
Han, D. et al., Oncotarget 8, 64853-64866 (2017).
Hirose, K., et al. J Comp Neurol 489, 180-194 (2005).
Ho, H. H. & Ivashkiv, L. B., The Journal of Biological Chemistry 281, 14111-14118 (2006).
Hoffman, H. J., et al., JAMA Otolaryngol Head Neck Surg 143, 274-285 (2017).
Holzer, P., Neuroscience 24, 739-768 (1988).
Holzer, P. Adv Exp Med Biol 298, 3-16 (1991).
Hu, B. H., et al., Hear Res 166, 62-71 (2002).
Hughes, G. J., et al. J Agric Food Chem 59, 12707-12712 (2011).
Hwang, J. H. & Chan, Y. C., ORL J Otorhinolaryngol Relat Spec 78, 268-275 (2016).
Ikeda, K. & Morizono, T. Hear Res 34, 307-311 (1988).
Jajoo, S., et al. Neoplasia 11, 1132-1145 (2009).
Jeong, H. J., et al. J Neurosci Res 85, 896-905 (2007).
Jung, S. H. et al. Mol Cells 37, 234-240 (2014).
Kamimura, T., et al. Hearing Research 131, 117-127 (1999).
Kanzaki, J. & Ouchi, T. Arch Otorhinolaryngol 230, 5-9 (1981).
Kaur, T. et al. Cell Death Dis 2, e180 (2011).
Kim, H.-J. et al. Head Neck 30, 1445-1456 (2008).
Kozela, E. et al. The Journal of Biological Chemistry 285 (2010).
Laemmli, U. K. Nature 227, 680-685 (1970).
Levy, D. E. & Lee, C. K. J Clin Invest 109, 1143-1148 (2002).
Li, W., Zhao, et al., Chinese Medical Journal 110, 883-886 (1997).
Liedtke, W. et al. Cell 103, 525-535 (2000).
Lin, S. et al. Alternat Med 2013, 629750 (2013).
Maeda, Y., et al., PloS one 8, e58775 (2013).
Martin-Saldana, S. et al. PLoS One 11, e0161954 (2016).
Meltser, I., Tahera, Y. & Canlon, B. Neuroscience 165, 1439-1446 (2010).
Min, T. J., et al., Clinical and Experimental Otorhinolaryngology 7, 275-280 (2014).
Modur, V. et al. PLoS One 11, e0156651 (2016).
Mukherjea, D. et al. Neuroscience 139, 733-740 (2006).
Mukherjea, D. et al. J Neurosci 28, 13056-13065 (2008).
Mukherjea, D. et al. Antioxidants & Redox Signaling 13, 589-598 (2010).
Mukherjea, D. et al. Antioxidants & Redox Signaling 14, 999-1010 (2011).
Mukhopadhyay, P. et al. Free Radic Biol Med 48, 457-467 (2010).
Murai, N., Kirkegaard, et al. J Neurotrauma 25, 72-77 (2008).
Nicotera, P. & Orrenius, S. Ann N Y Acad Sci 648, 17-27 (1992).
Ohlemiller, K. K., et al., Audiol Neurootol 4, 229-236 (1999).
Orrenius, S., et al. Ann Neurol 32 Suppl, S33-42 (1992a).
Orrenius, S., et al., Toxicol Lett 64-65 Spec No, 357-364 (1992b).
Pomonis, J. D. et al. J Pharmacol Exp Ther 306, 387-393 (2003).
Pouyatos, B., et al. J Rehabil Res Dev 45, 1053-1064 (2008).
Puntambekar, P., et al. J Neurochem 95, 1689-1703 (2005).
Qing, Y. & Stark, G. R., The J. of Biol. Chemistry 279, 41679-41685 (2004).
Ramkumar, V., et al. Hear Res 188, 47-56 (2004).
Roy, S., et al. J Clin Invest 123, 4945-4949 (2013).
Sanchez, A. J. & Garcia-Merino, A. Clinical Immunology 142, 57-67 (2012).
Satoh, H., et al. J Assoc Res Otolaryngol 4, 139-147 (2003).
Shen, Y., et al., Proc Natl Acad Sci USA 98, 1543-1548 (2001).
Shimeda, Y. et al. Biol Pharm Bull 28, 1635-1638 (2005).
Sinha, K., et al., Archives of Toxicology 87, 1157-1180 (2013).
So, H. et al. J Assoc Res Otolaryngol 8, 338-355 (2007).
Stephanou, A. et al. The J. of Biol. Chemistry, 275, 10002-10008 (2000).
Suresh, D. & Srinivasan, K., Indian J. Med. Res. 131, 682-691 (2010).
Ta, L. E. et al., Mol Pain 6, 15 (2010).
Takumida, M., et al., Oto-Laryngologica 125, 929-934 (2005).
Tan, W. J., et al., Histochemistry and Cell Biology 146, 219-230 (2016).
Tanaka, C., et al., Laryngoscope 119, 1374-1379 (2009).
Theneshkumar, S. et al. Med Sci Monit 15, Br173-177 (2009).
Tornabene, S. V., et al. Hearing Research 222, 115-124 (2006).
Turner, J. G., et al., J Am Assoc Lab Anim Sci 46, 10-13 (2007).
Valenzano, K. J. et al. J Pharmacol Exp Ther 306, 377-386 (2003).
Vass, Z., et al., Acta Otolaryngol 114, 156-161 (1994).
Vass, Z., et al., Hear Res 89, 86-92 (1995a).
Vass, Z., et al., Acta Otolaryngol 115, 754-758 (1995b).
Waissbluth, S., et al. J. Otology & Neurotology, 3, 302-310 (2012).
Wu, T., et al. Hear Res 272, 117-124 (2011).
Yamane, H. et al. Eur Arch Otorhinolaryngol 252, 504-508 (1995).
Yamashita, D., et al. Neuroscience 134, 633-642 (2005).
Yang, J. et al. Neoplasma 60, 364-372 (2013).

Yoshida, N. & Liberman, M. C. Hearing Research 148, 213-219 (2000).

Zheng, J. et al. Journal of Neurophysiology 90, 444-455 (2003).

Zou, J., Pyykko, I., Sutinen, P. & Toppila, E. Hear Res 202, 13-20 (2005).

Zygmunt, P. M. et al. Nature 400, 452-457 (1999).

Noise-Induced Hearing Loss web page. National Institute on Deafness and Other Communication Disorders (NIDCD), National Institutes of Health. Available at https://www.nidcd.nih.gov/health/noise-induced-hearing-loss.

Wang et al., 2003. Otology & Neurotology 24(1): 52-57.

SIU Today: Research Looks at Chili Pepper in Hearing Loss. https://news.siu.edu/2014/08/082514SIUToday-Chili-PepperResearch.php. (Aug. 25, 2014).

Savel et al. U.S. patent application Ser. No. 16/637,767.

Lichter et al. U.S. Pat. No. 10,092,580.

Brockhuas et al. U.S. Pat. No. 8,063,182.

Brockhuas et al. U.S. Pat. No. 8,163,522.

Frey E, ET AL. eNeuro. 2018 May 30; 5 (3). pii: ENEURO.0095-18.2018. doi: 10.1523/ENEURO.0095-18.2018. eCollection 2018 May-June PubMed PMID: 29854941; PubMed Central PMCID: PMC5975717.

Perry K J, Hamilton P W, Sonam S, Singh R, Henry J J. Dev Dyn. 2019 July; 248(7):530-544. doi: 10.1002/dvdy.42. Epub 2019 May 1. PubMed PMID: 30993812.

The invention claimed is:

1. A regimen comprising:
an amount of a TRPV1 agonist; and
an amount of a TNF-α inhibitor,
said regimen being capable of physiologically restoring hearing by repairing at least one damaged auditory hair cell, synapse, or ganglion.

2. The regimen of claim 1 wherein the TNF-α inhibitor comprises etanercept, an anti-TNF-α monoclonal antibody, or a combination thereof.

3. The regimen of claim 2, wherein the TRPV1 agonist comprises capsaicin and the anti-TNF-α monoclonal antibody comprises adalimumab, golimumab, infliximab or a combination thereof.

4. The regimen of claim 3 wherein the amount of capsaicin is about 1 mg to about 1000 mg and the amount of the anti-TNF-α monoclonal antibody is about 1 mg to about 100 mg.

5. The regimen of claim 3 wherein the capsaicin is formulated as an oral formulation or an injectable formulation.

6. The regimen of claim 2 wherein the TNF-α inhibitor comprises etanercept.

7. The regimen of claim 6 wherein the etanercept comprises an injectable formulation.

8. The regimen of claim 1, wherein the TNF-α inhibitor is formulated as a trans-tympanic injection, subcutaneous injection or as an orally bioavailable formulation.

9. A method of restoring hearing in a subject comprising providing a regimen to a subject having the steps of:
(1) providing a TRPV1 agonist, a CB2 agonist, or a dual TRPV1/CB2 agonist to the subject; and
(2) providing a TNF-α inhibitor to the subject; and
restoring hearing damage in the subject after exposure to an ototoxic agent.

10. The method of claim 9, wherein the dual TRPV1/CB2 agonist is capsaicin and the subject is provided capsaicin at a dosage amount of about 1 mg/day to about 100 mg/day.

11. The method of claim 9 wherein the TNF-α inhibitor comprises ETA or an anti-TNF-α monoclonal antibody comprising adalimumab, golimumab, infliximab or a combination thereof.

12. The method of claim 9 wherein the regimen is provided after exposure to the ototoxic agent.

13. The method of claim 9, wherein the regimen is provided to the subject after exposure to a damaging decibel level of noise, administration of cisplatin, or an aminoglycoside antibiotic, or after hearing loss has been detected.

14. A regimen for restoring hearing sensitivity level in a subject having a reduced hearing sensitivity level comprising:
providing a regimen comprising an amount of a TNF-α inhibitor and an amount of a TRPV1 agonist to treat the subject; and
improving hearing sensitivity level in the treated subject, wherein hearing in the treated subject is improved by at least 10% compared to the subject's hearing level before treatment.

15. The regimen of claim 14, wherein the TNF-α inhibitor is etanercept and the TRPV1 agonist is capsaicin.

16. The regimen of claim 15 wherein the TNF-α inhibitor is provided in an injection delivery form and the capsaicin is provided in an oral, injectable, or inhalable delivery form.

17. The regimen of claim 16, wherein the amount of the TNF-α inhibitor or the amount of the capsaicin alone does not improve hearing level in the subject.

18. The regimen of claim 14, wherein the treated subject has an enhanced hearing sensitivity level of about 15% to about 25% compared to the subject's hearing sensitivity level before treatment.

19. A method for restoring hearing in a subject, comprising providing a treatment regimen to the subject after exposure to an ototoxic agent, comprising:
   providing an amount of capsaicin and an amount of a TNF-α inhibitor to the subject; and
   restoring hearing in the subject after exposure to an insult comprising administration of cisplatin, ototoxic drugs, or exposure to a damaging decibel level of noise.

20. The method of claim 19 wherein the subject is administered an amount of a TNF-α inhibitor comprising etanercept or an anti-TNF monoclonal antibody, the anti-TNF monoclonal antibody comprising adalimumab, golimumab, infliximab or a combination thereof.

\* \* \* \* \*

SEQUENCE LISTING

```
<160> NUMBER OF SEQ ID NOS: 26

<210> SEQ ID NO 1
<211> LENGTH: 20
<212> TYPE: DNA
<213> ORGANISM: Rattus norvegicus

<400> SEQUENCE: 1
atggctgggg agacacctga                                                     20

<210> SEQ ID NO 2
<211> LENGTH: 21
<212> TYPE: DNA
<213> ORGANISM: Rattus norvegicus

<400> SEQUENCE: 2
gcaaagtaga agagggcaac c                                                   21

<210> SEQ ID NO 3
<211> LENGTH: 18
<212> TYPE: DNA
<213> ORGANISM: Rattus norvegicus

<400> SEQUENCE: 3
ccttctttga gttcggtg                                                       18

<210> SEQ ID NO 4
<211> LENGTH: 18
<212> TYPE: DNA
<213> ORGANISM: Rattus norvegicus

<400> SEQUENCE: 4
gagacagcca ggagaaat                                                       18

<210> SEQ ID NO 5
<211> LENGTH: 20
<212> TYPE: DNA
<213> ORGANISM: Rattus norvegicus

<400> SEQUENCE: 5
cattctacta ctaccagatc                                                     20

<210> SEQ ID NO 6
<211> LENGTH: 19
<212> TYPE: DNA
<213> ORGANISM: Rattus norvegicus

<400> SEQUENCE: 6
atgtgcttgt caccaccag                                                      19
```

<210> SEQ ID NO 7
<211> LENGTH: 21
<212> TYPE: DNA
<213> ORGANISM: Rattus norvegicus

<400> SEQUENCE: 7
atggtgaagg tcggtgtgaa c                                    21

<210> SEQ ID NO 8
<211> LENGTH: 21
<212> TYPE: DNA
<213> ORGANISM: Rattus norvegicus

<400> SEQUENCE: 8
tgtagttgag gtcaatgaag g                                    21

<210> SEQ ID NO 9
<211> LENGTH: 20
<212> TYPE: DNA
<213> ORGANISM: Rattus norvegicus

<400> SEQUENCE: 9
gtgaacaagg gaaggctcat                                      20

<210> SEQ ID NO 10
<211> LENGTH: 19
<212> TYPE: DNA
<213> ORGANISM: Rattus norvegicus

<400> SEQUENCE: 10
gacccacaga agaacacgc                                       19

<210> SEQ ID NO 11
<211> LENGTH: 22
<212> TYPE: DNA
<213> ORGANISM: Rattus norvegicus

<400> SEQUENCE: 11
ctcgtacctg ttcatcagca gc                                   22

<210> SEQ ID NO 12
<211> LENGTH: 22
<212> TYPE: DNA
<213> ORGANISM: Rattus norvegicus

<400> SEQUENCE: 12
cagcaggaag atagcgttgg ag                                   22

<210> SEQ ID NO 13
<211> LENGTH: 20
<212> TYPE: DNA
<213> ORGANISM: Rattus norvegicus

<400> SEQUENCE: 13
ggtggacgag gtaaactgga                                      20

<210> SEQ ID NO 14
<211> LENGTH: 20
<212> TYPE: DNA
<213> ORGANISM: Rattus norvegicus

<400> SEQUENCE: 14

```
gctgggtggc atgtctatct                                           20

<210> SEQ ID NO 15
<211> LENGTH: 21
<212> TYPE: DNA
<213> ORGANISM: Rattus norvegicus

<400> SEQUENCE: 15
atggtgaagg tcggtgtgaa c                                         21

<210> SEQ ID NO 16
<211> LENGTH: 21
<212> TYPE: DNA
<213> ORGANISM: Rattus norvegicus

<400> SEQUENCE: 16
tgtagttgag gtcaatgaag g                                         21

<210> SEQ ID NO 17
<211> LENGTH: 20
<212> TYPE: DNA
<213> ORGANISM: Rattus norvegicus

<400> SEQUENCE: 17
caaggctgtc ttcatcatcc                                           20

<210> SEQ ID NO 18
<211> LENGTH: 20
<212> TYPE: DNA
<213> ORGANISM: Rattus norvegicus

<400> SEQUENCE: 18
agtccagttt acctcgtcca                                           20

<210> SEQ ID NO 19
<211> LENGTH: 20
<212> TYPE: DNA
<213> ORGANISM: Rattus norvegicus

<400> SEQUENCE: 19
gtgaacaagg gaaggctcat                                           20

<210> SEQ ID NO 20
<211> LENGTH: 19
<212> TYPE: DNA
<213> ORGANISM: Rattus norvegicus

<400> SEQUENCE: 20
gacccacaga agaacacgc                                            19

<210> SEQ ID NO 21
<211> LENGTH: 21
<212> TYPE: DNA
<213> ORGANISM: Rattus norvegicus

<400> SEQUENCE: 21
cagaccctca cactcagatc a                                         21

<210> SEQ ID NO 22
<211> LENGTH: 21
<212> TYPE: DNA
<213> ORGANISM: Rattus norvegicus

<400> SEQUENCE: 22
```

```
tgaagagaac ctgggagtag a                                               21

<210> SEQ ID NO 23
<211> LENGTH: 21
<212> TYPE: DNA
<213> ORGANISM: Rattus norvegicus

<400> SEQUENCE: 23
tgatcgaaga ctacgtgcaa c                                               21

<210> SEQ ID NO 24
<211> LENGTH: 21
<212> TYPE: DNA
<213> ORGANISM: Rattus norvegicus

<400> SEQUENCE: 24
gtactcctgg tcttcaatgt t                                               21

<210> SEQ ID NO 25
<211> LENGTH: 20
<212> TYPE: DNA
<213> ORGANISM: Rattus norvegicus

<400> SEQUENCE: 25
aagtacgagt ggttccagga                                                 20

<210> SEQ ID NO 26
<211> LENGTH: 20
<212> TYPE: DNA
<213> ORGANISM: Rattus norvegicus

<400> SEQUENCE: 26
gcacagctgc attgatctcg                                                 20
```